(12) United States Patent
Uchida et al.

(10) Patent No.: US 7,589,109 B2
(45) Date of Patent: Sep. 15, 2009

(54) OXYINDOLE DERIVATIVES

(75) Inventors: Chikara Uchida, Chita-gun (JP); Hiroki Sone, Chita-gun (JP); Kiyoshi Kawamura, Chita-gun (JP)

(73) Assignee: Pfizer Inc, New York, NY (US)

( * ) Notice: Subject to any disclaimer, the term of this patent is extended or adjusted under 35 U.S.C. 154(b) by 561 days.

(21) Appl. No.: 11/360,095

(22) Filed: Feb. 22, 2006

(65) Prior Publication Data

US 2006/0194842 A1 Aug. 31, 2006

Related U.S. Application Data

(60) Provisional application No. 60/655,276, filed on Feb. 22, 2005.

(51) Int. Cl.
 *A61K 31/454* (2006.01)
 *C07D 403/14* (2006.01)
(52) U.S. Cl. ................................ 514/323; 546/201
(58) Field of Classification Search ........... 514/323; 546/201
 See application file for complete search history.

(56) References Cited

U.S. PATENT DOCUMENTS

| | | | | |
|---|---|---|---|---|
| 5,223,511 A | 6/1993 | Turconi et al. | | 514/304 |
| 5,280,028 A | 1/1994 | Flynn et al. | | 514/294 |
| 5,300,512 A | 4/1994 | Flynn et al. | | 514/304 |
| 5,358,954 A | 10/1994 | Turconi et al. | | 514/304 |
| 5,399,562 A | 3/1995 | Becker et al. | | 514/278 |
| 5,521,193 A | 5/1996 | Flynn et al. | | 514/290 |
| 5,534,521 A | 7/1996 | Flynn et al. | | 514/290 |
| 5,552,408 A | 9/1996 | Turconi et al. | | 514/304 |
| 5,576,318 A | 11/1996 | Bietti et al. | | 514/253 |
| 5,705,498 A | 1/1998 | Gaster et al. | | 514/214 |
| 5,922,733 A | 7/1999 | Forbes et al. | | 514/310 |
| 5,955,470 A | 9/1999 | Gittos | | 514/294 |
| 6,002,009 A | 12/1999 | Cereda et al. | | 546/199 |
| 6,069,152 A | 5/2000 | Schaus et al. | | 514/322 |
| 6,117,882 A | 9/2000 | Schaus et al. | | 514/304 |
| 6,207,697 B1 | 3/2001 | Han et al. | | 514/409 |
| 6,310,059 B1 | 10/2001 | Snutch | | 514/222.2 |
| 6,492,375 B2 | 12/2002 | Snutch | | 514/255 |
| 6,548,548 B2 | 4/2003 | Campbell et al. | | 514/617 |
| 6,552,042 B2 | 4/2003 | Han et al. | | 514/322 |
| 6,624,184 B1 | 9/2003 | Gu et al. | | 514/374 |
| 6,713,650 B2 | 3/2004 | Ibrahim et al. | | 564/188 |
| 7,012,080 B2 * | 3/2006 | Iguchi et al. | | 514/300 |
| 2005/0148573 A1 | 7/2005 | Katsu et al. | | 514/210.16 |
| 2005/0277671 A1 * | 12/2005 | Ando et al. | | 514/322 |
| 2005/0277672 A1 | 12/2005 | Ando et al. | | 514/322 |
| 2005/0277673 A1 | 12/2005 | Ando et al. | | 514/322 |

FOREIGN PATENT DOCUMENTS

| | | |
|---|---|---|
| EP | 0377967 | 7/1990 |
| EP | 0623621 | 9/1994 |
| EP | 0655439 | 5/1995 |
| FR | 2694292 | 2/1994 |
| WO | WO 9205174 | 4/1992 |
| WO | WO 9212149 | 7/1992 |
| WO | WO 9307147 | 4/1993 |
| WO | WO 9318027 | 9/1993 |
| WO | WO 9429298 | 12/1994 |
| WO | WO 9615166 | 5/1996 |
| WO | WO 9964055 | 12/1999 |
| WO | WO 0026197 | 5/2000 |
| WO | WO 0146166 | 6/2001 |
| WO | WO 0230886 | 4/2002 |
| WO | WO 0246141 | 6/2002 |
| WO | WO 2004113300 | 12/2004 |
| WO | WO 2005021539 | 3/2005 |
| WO | WO 2005123718 | 12/2005 |

OTHER PUBLICATIONS

Howard, H. R., et al., 3-Benzisothiazolylpiperazine Derivatives as Potential Atypical Antipsychotic Agents, *J. Med. Chem.*, vol. 39, pp. 143-148, (1996).

Jonsson, N. A., et al., 3,3-dialkylindoin-2-ones and 3,3-dialkylisoindolin-1-ones. 1. Hofman Hypohalite Degradation of 4,4-dialkyl-1,3-dioxo-1,2,3,4-tetrahydroisoquinolines (4,4-dialkylhomophthalimidies), *Acta Chemica Scandinavica*, B 28, pp. 225-232, (1974).

(Continued)

*Primary Examiner*—Celia Chang
(74) *Attorney, Agent, or Firm*—Gregg C. Benson; Garth Butterfield; Patricia K. Fitzsimmons

(57) ABSTRACT

This invention relates to compounds of the formula (I):

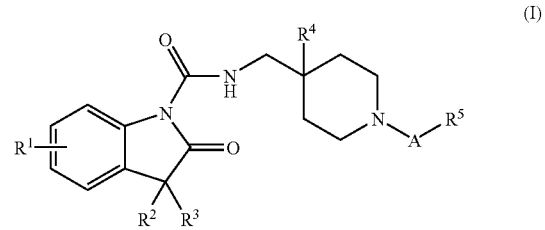

(I)

or a pharmaceutically acceptable salt thereof, wherein:
A, $R^1$, $R^2$, $R^3$, $R^4$ and $R^5$ are each as described herein or a pharmaceutically acceptable salt, and compositions containing such compounds and the use of such compounds in the treatment of a condition mediated by 5-$HT_4$ agonistic activity such as, but not limited to, as gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageal disease, nausea, central nervous system disease, Alzheimer's disease, cognitive disorder, emesis, migraine, neurological disease, pain, cardiovascular disorders, cardiac failure, heart arrhythmia, diabetes or apnea syndrome.

5 Claims, No Drawings

OTHER PUBLICATIONS

Quallich, G. J., et al., A General Oxindole Synthesis, *Synthesis*, pp. 51-53, (1993).

Roberson, D. W., et al., Dihydropyridazinone Cardiotonics: The Discovery and Inotropic Activity of 1,3-Dihydro-3,3-dimethyl-5-(1,4,5,6-tetrahydro-6-oxo-3-pyridazinyl)-2H-indol-2-one, *J. Med. Chem.*, vol. 29, pp. 1832-1840, (1986).

International Search Report for Application No. PCT/IB2006/000519.

Written Opinion for Application No. PCT/IB2006/000519.

English language translation of FR 2,694,292.

English language translation of WO 96/05166.

\* cited by examiner

OXINDOLE DERIVATIVES

This application is filed claiming priority under 35 USC 119(e) from U. S. provisional application 60/655,276 filed on Feb. 22, 2005.

BACKGROUND OF THE INVENTION

This invention relates to Oxyindole Derivatives. These compounds have selective 5-$HT_4$ receptor agonistic activity. The present invention also relates to a pharmaceutical composition, method of treatment and use, comprising the above derivatives for the treatment of disease conditions mediated by 5-$HT_4$ receptor activity; in particular 5-$HT_4$ receptor agonistic activity.

In general, 5-$HT_4$ receptor agonists are found to be useful for the treatment of a variety of diseases such as gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageal disease, nausea, central nervous system disease, Alzheimer's disease, cognitive disorder, emesis, migraine, neurological disease, pain, cardiovascular disorders, cardiac failure, heart arrhythmia, diabetes and apnea syndrome (See *TiPs*, 1992, 13, 141; Ford A. P. D. W. et al., *Med. Res. Rev.*, 1993, 13, 633; Gullikson G. W. et al., *Drug Dev. Res.*, 1992, 26, 405; Richard M. Eglen et al, *TIPS*, 1995, 16, 391; Bockaert J. Et al., *CNS Drugs*, 1, 6; Romanelli M. N. et al., *Arzheim Forsch./Drug Res.*, 1993, 43, 913; Kaumann A. et al., *Naunyn-Schmiedeberg's*. 1991, 344, 150; and Romanelli M. N. et al., *Arzheim Forsch./Drug Res.*, 1993, 43, 913).

U.S. Pat. No. 5,399,562A discloses indolone compounds as 5-$HT_4$ agonists or antagonists and/or 5-$HT_3$ antagonists. Especially, compounds represented by the following formula is disclosed as Example 5:

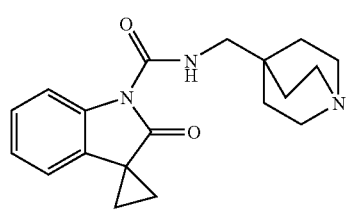

Compound A

There is a need to provide new 5-$HT_4$ agonists that are good drug candidates. In particular, preferred compounds should bind potently to the 5-$HT_4$ receptor whilst showing little affinity for other receptors and show functional activity as agonists. They should be well absorbed from the gastrointestinal tract, be metabolically stable and possess favorable pharmacokinetic properties. When targeted against receptors in the central nervous system, they should cross the blood brain barrier freely and when targeted selectively against receptors in the peripheral nervous system, they should not cross the blood brain barrier. They should be non-toxic and demonstrate few side-effects. Furthermore, the ideal drug candidate will exist in a physical form that is stable, non-hygroscopic and easily formulated.

SUMMARY OF THE INVENTION

In this invention, it has now been found out that replacing the quinuclidine ring with a piperidine ring significantly improves 5-$HT_4$ agonistic activity.

Therefore, it has now surprisingly been found that compounds of this invention have stronger selective 5-$HT_4$ agonistic compared with the prior art, and thus are useful for the treatment of disease conditions mediated by 5-$HT_4$ activity such as gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageal disease, nausea, central nervous system disease, Alzheimer's disease, cognitive disorder, emesis, migraine, neurological disease, pain, cardiovascular disorders, cardiac failure, heart arrhythmia, diabetes and apnea syndrome (hereinafter these diseases are referred to as '5-$HT_4$ Diseases').

The present invention provides a compound of the following formula (I):

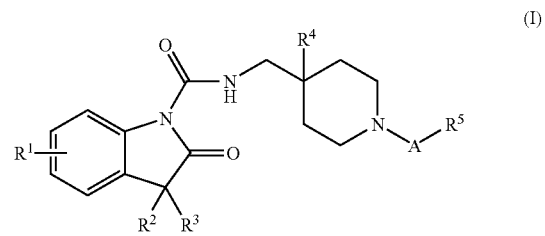

(I)

or a pharmaceutically acceptable salt thereof, wherein:

A represents a $C_1$-$C_4$ alkylene group, said alkylene group being unsubstituted or substituted with 1 to 4 substituents independently selected from the group consisting of a $C_1$-$C_4$ alkyl group, a hydroxy-$C_1$-$C_4$ alkyl group and a $C_1$-$C_2$ alkoxy-$C_1$-$C_4$ alkyl group, wherein 2 of said substituents may optionally form a bridge to yield a 3 to 6 membered ring being unsubstituted or substituted with a hydroxy group or a carboxy group;

$R^1$ represents a hydrogen atom, a halogen atom or a $C_1$-$C_4$ alkyl group;

$R^2$ and $R^3$ independently represent a methyl or ethyl group, or $R^2$ and $R^3$ may together form a $C_2$-$C_4$ alkylene bridge to yield 3 to 5 membered ring;

$R^4$ represents a hydrogen atom, a halogen atom or a hydroxy group; and $R^5$ represents a hydroxy group, a carboxy group, a tetrazolyl group, a 5-oxo-1,2,4-oxadiazole-3-yl group or a 5-oxo-1,2,4-thiadiazole-3-yl group.

Also, the present invention provides the use of a compound of formula (I) or a pharmaceutically acceptable salt thereof, each as described herein, for the manufacture of a medicament for the treatment of a condition mediated by 5-$HT_4$ modulating activity; in particular, 5-$HT_4$ agonistic activity.

Preferably, the present invention also provides the use of a compound of formula (I) or a pharmaceutically acceptable salt thereof, each as described herein, for the manufacture of a medicament for the treatment of diseases selected from 5-$HT_4$ Diseases.

Also, the present invention provides a pharmaceutical composition comprising a compound of formula (I) or a pharmaceutically acceptable salt thereof, each as described herein, together with a pharmaceutically acceptable carrier for said compound.

Also, the present invention provides a pharmaceutical composition comprising a compound of formula (I) or a pharmaceutically acceptable salt thereof, each as described herein, together with a pharmaceutically acceptable carrier for said compound and another pharmacologically active agent.

Further, the present invention provides a method of treatment of a condition mediated by $5\text{-}HT_4$ modulating activity, in a mammalian subject, which comprises administering to a mammal in need of such treatment a therapeutically effective amount of a compound of formula (I) or a pharmaceutically acceptable salt thereof, each as described herein.

Examples of conditions mediated by $5\text{-}HT_4$ modulating activity include, but are not limited to, $5\text{-}HT_4$ Diseases.

The compounds of the present invention may show less toxicity, good absorption, distribution, good solubility, less protein binding affinity other than acid pump, less drug-drug interaction, and good metabolic stability.

DETAILED DESCRIPTION OF THE INVENTION

In the compounds of the present invention:

Where A is the $C_1$-$C_4$ alkylene group, this $C_1$-$C_4$ alkylene group may be a straight chain group having one to four carbon atoms, and examples include, but are not limited to, a methylene, ethylene, trimethylene and tetramethylene. Of these, methylene or ethylene is preferred; ethylene is more preferred.

Where $R^2$ and $R^3$ form the $C_2$-$C_4$ alkylene bridge to yield the 3 to 5 membered ring, this 3 to 5 membered ring may be a cycloalkyl group having three to five carbon atoms, and examples include, but are not limited to, cyclopropyl, cyclobutyl and cyclopentyl. Of these, cyclopentyl is preferred.

Where $R^1$ and $R^4$ are the halogen atom, this may be a fluorine, chlorine, bromine or iodine atom. Of these, a fluorine atom and a chlorine atom are preferred; a fluorine atom is more preferred.

Where $R^1$ and the substituent of A are the $C_1$-$C_4$ alkyl group, this $C_1$-$C_4$ alkyl group may be a straight or branched chain group having one to four carbon atoms, and examples include, but are not limited to, a methyl, ethyl, propyl, isopropyl, butyl, isobutyl, sec-butyl and tert-butyl. Of these, methyl or ethyl is preferred; methyl is more preferred for $R^1$.

Where the substituent of A is the hydroxy-$C_1$-$C_4$ alkyl group, this represents the said $C_1$-$C_4$ alkyl group substituted with hydroxy, and examples include, but are not limited to, a hydroxymethyl, 2-hydroxyethyl, 1-hydroxyethyl, 3-hydroxypropyl, 2-hydroxypropyl, 2-hydroxy-1-methylethyl, 4-hydroxybutyl, 3-hydroxybutyl, 2-hydroxybutyl, 3-hydroxy-2-methylpropyl and 3-hydroxy-1-methylpropyl. Of these, hydroxy-alkyl groups having from 1 to 3 carbon atoms are preferred; hydroxymethyl, 2-hydroxyethyl, and 2-hydroxypropyl are more preferred.

Where the substituent of A is the $C_1$-$C_2$ alkoxy-$C_1$-$C_4$ alkyl group this represents the said $C_1$-$C_4$ alkyl group substituted with methoxy or ethoxy, and examples include, but are not limited to, a methoxymethyl, ethoxymethyl, 2-methoxyethyl, 2-ethoxyethyl, 1-methoxyethyl, 3-methoxypropyl, 3-ethoxypropyl, 2-methoxypropyl, 2-methoxy-1-methylethyl, 4-methoxybutyl, 4-ethoxybutyl, 3-methoxybutyl, 2-methoxybutyl, 3-methoxy-2-methylpropyl and 3-methoxy-1-methylpropyl. Of these, alkyloxy-alkyl groups having from 2 to 4 carbon atoms are preferred; methoxymethyl, 2-methoxyethyl and 3-methoxypropyl are more preferred.

Where 2 of the substituent of A form the bridge to yield the 3 to 6 membered ring, this may be a cycloalkyl or heterocyclyl group and examples include a cyclopropyl, cyclopentyl, cyclobutyl, cyclohexyl, methylcyclopropyl, ethylcyclopropyl, methylcyclobutyl, methylcyclopentyl, methylcyclohexyl, ethylcyclohexyl, hydroxycyclopropyl, hydroxycyclobutyl, hydroxycyclopentyl, hydroxycyclohexyl, methoxycyclopropyl, methoxycyclobutyl, methoxycyclopentyl, methoxycyclohexyl, tetrahydrofuryl and tetrahydropyranyl, preferably cyclopropyl, cyclobutyl, cyclopentyl, cyclohexyl, methoxycyclohexyl and tetrahydropyranyl, and most preferably cyclobutyl, cyclopentyl, cyclohexyl and tetrahydropyranyl.

The term "treating" and "treatment", as used herein, refers to curative, palliative and prophylactic treatment, including reversing, alleviating, inhibiting the progress of, or preventing the disorder or condition to which such term applies, or one or more symptoms of such disorder or condition.

Preferred compounds of the present invention are those compounds of formula (I) or a pharmaceutically acceptable salt thereof, each as described herein, in which:

(A) A is a $C_1$-$C_2$ alkylene group, said alkylene group being unsubstituted or substituted with 1 to 4 substituents independently selected from the group consisting of a $C_1$-$C_4$ alkyl group, a hydroxy-$C_1$-$C_4$ alkyl group and a $C_1$-$C_2$ alkoxy-$C_1$-$C_4$ alkyl group, wherein 2 of said substituents may optionally form a bridge to yield a 3 to 6 membered ring; $R^1$ is a hydrogen atom, a halogen atom or a $C_1$-$C_4$ alkyl group; $R^2$ and $R^3$ is a methyl group, or $R^2$ and $R^3$ may together form a tetramethylene bridge to yield 5 membered ring; $R^4$ is a hydrogen atom, a halogen atom or a hydroxy group; and $R^5$ is a hydroxy group, a carboxy group, a tetrazolyl group, a 5-oxo-1,2,4-oxadiazole-3-yl group or a 5-oxo-1,2,4-thiadiazole-3-yl group;

(B) A is a $C_1$-$C_2$ alkylene group, said alkylene group being unsubstituted or substituted with 1 to 2 substituents independently selected from the group consisting of a $C_1$-$C_4$ alkyl group, a hydroxy-$C_1$-$C_4$ alkyl group and a $C_1$-$C_2$ alkoxy-$C_1$-$C_4$ alkyl group, wherein 2 of said substituents may optionally form a bridge to yield a 3 to 6 membered ring; $R^1$ is a hydrogen atom or a halogen atom; $R^2$ and $R^3$ is a methyl group, or $R^2$ and $R^3$ may together form a tetramethylene bridge to yield a 5 membered ring; $R^4$ is a hydrogen atom; and $R^5$ is a carboxy group, a tetrazolyl group, a 5-oxo-1,2,4-oxadiazole-3-yl group or a 5-oxo-1,2,4-thiadiazole-3-yl group;

(C) A is a $C_1$-$C_2$ alkylene group, said alkylene group being unsubstituted or substituted with 2 substituents independently selected from the group consisting of a $C_1$-$C_4$ alkyl group and a hydroxy-$C_1$-$C_4$ alkyl group, wherein 2 of said substituents may optionally form a bridge to yield a 3 to 6 membered ring; $R^1$ is a hydrogen atom or a fluorine atom; $R^2$ and $R^3$ is a methyl group, or $R^2$ and $R^3$ may together form a tetramethylene bridge to yield a 5 membered ring; $R^4$ is a hydrogen atom; and $R^5$ is a carboxy group or a tetrazolyl group;

(D) A is

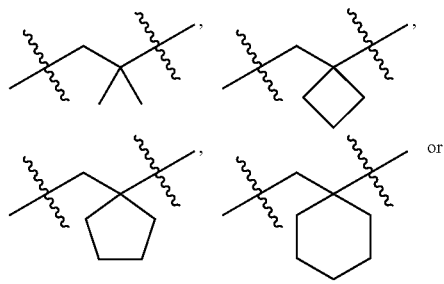

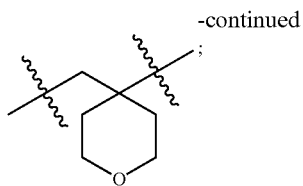

R¹ is a hydrogen atom or a fluorine atom; R² and R³ is a methyl group; R⁴ is a hydrogen atom; and R⁵ is a carboxy group or a tetrazolyl group (E) A is a $C_1$-$C_2$ alkylene group, said alkylene group being unsubstituted or substituted with 2 substituents independently selected from the group consisting of a $C_1$-$C_2$ alkyl group and a hydroxy-$C_1$-$C_2$ alkyl group, wherein 2 of said substituents may optionally form a bridge to yield a 4 to 6 membered ring; R¹ is a hydrogen atom or a fluorine atom; R² and R³ is a methyl group, or R² and R³ may together form a tetramethylene bridge to yield 5 membered ring; R⁴ is a hydrogen atom; and R⁵ is a carboxy group or a tetrazolyl group;

(F) A is

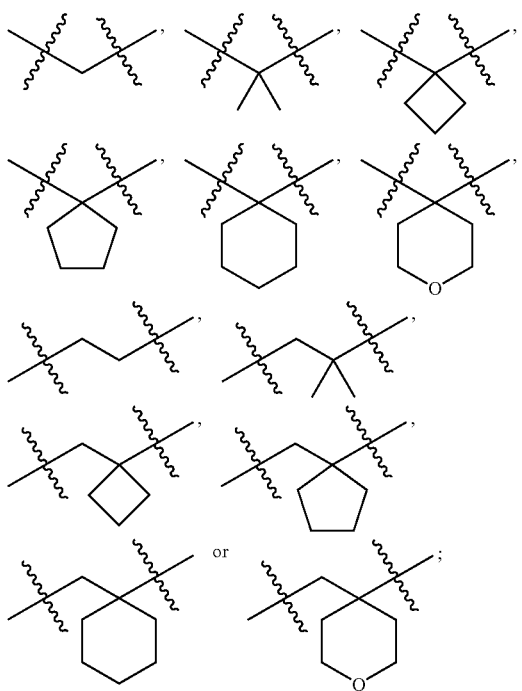

R¹ is a hydrogen atom or a fluorine atom; R² and R³ is a methyl group; R⁴ is a hydrogen atom; and R⁵ is a carboxy group or a tetrazolyl group (G) A is a $C_1$-$C_4$ alkylene group, said alkylene group being unsubstituted or substituted with 1 to 4 substituents independently selected from the group consisting of a $C_1$-$C_4$ alkyl group, a hydroxy-$C_1$-$C_4$ alkyl group and a $C_1$-$C_2$ alkoxy-$C_1$-$C_4$ alkyl group, wherein 2 of said substituents may optionally form a bridge to yield a 3 to 6 membered ring being unsubstituted or substituted with a hydroxy group or a carboxy group; R¹ is a hydrogen atom, a halogen atom or a $C_1$-$C_4$ alkyl group; R² and R³ is a methyl group, or R² and R³ may together form a tetramethylene bridge to yield 5 membered ring; R⁴ is a hydrogen atom, a halogen atom or a hydroxy group; and R⁵ is a hydroxy group, a carboxy group, a tetrazolyl group, a 5-oxo-1,2,4-oxadiazole-3-yl group or a 5-oxo-1,2,4-thiadiazole-3-yl group;

(H) A is a $C_1$-$C_2$ alkylene group, said alkylene group being unsubstituted or substituted with 1 to 4 substituents independently selected from the group consisting of a $C_1$-$C_4$ alkyl group, a hydroxy-$C_1$-$C_4$ alkyl group and a $C_1$-$C_2$ alkoxy-$C_1$-$C_4$ alkyl group, wherein 2 of said substituents may optionally form a bridge to yield a 3 to 6 membered ring; R¹ is a hydrogen atom, or a halogen atom; R² and R³ is a methyl group, or R² and R³ may together form a tetramethylene bridge to yield 5 membered ring; R⁴ is a hydrogen atom, a halogen atom or a hydroxy group; and R⁵ is a hydroxy group, a carboxy group, a tetrazolyl group, a 5-oxo-1,2,4-oxadiazole-3-yl group or a 5-oxo-1,2,4-thiadiazole-3-yl group;

(I) A is a $C_1$-$C_2$ alkylene group, said alkylene group being unsubstituted or substituted with 1 to 4 substituents independently selected from the group consisting of a $C_1$-$C_4$ alkyl group, a hydroxy-$C_1$-$C_4$ alkyl group and a $C_1$-$C_2$ alkoxy-$C_1$-$C_4$ alkyl group, wherein 2 of said substituents may optionally form a bridge to yield a 3 to 6 membered ring; R¹ is a hydrogen atom, or a halogen atom; R² and R³ is a methyl group, or R² and R³ may together form a tetramethylene bridge to yield 5 membered ring; R⁴ is a hydrogen atom, a fluorine atom or a hydroxy group; and R⁵ is a hydroxy group, a carboxy group, a tetrazolyl group, a 5-oxo-1,2,4-oxadiazole-3-yl group or a 5-oxo-1,2,4-thiadiazole-3-yl group;

(J) A is a $C_1$-$C_2$ alkylene group, said alkylene group being unsubstituted or substituted with 1 to 2 substituents independently selected from the group consisting of a $C_1$-$C_4$ alkyl group, a hydroxy-$C_1$-$C_4$ alkyl group and a $C_1$-$C_2$ alkoxy-$C_1$-$C_4$ alkyl group, wherein 2 of said substituents may optionally form a bridge to yield a 3 to 6 membered ring; R¹ is a hydrogen atom or a halogen atom; R² and R³ is a methyl group; R⁴ is a hydrogen atom; and R⁵ is a carboxy group, a tetrazolyl group, a 5-oxo-1,2,4-oxadiazole-3-yl group or a 5-oxo-1,2,4-thiadiazole-3-yl group;

(K) A is a $C_1$-$C_2$ alkylene group, said alkylene group being unsubstituted or substituted with 2 substituents independently selected from the group consisting of a $C_1$-$C_4$ alkyl group and a hydroxy-$C_1$-$C_4$ alkyl group, wherein 2 of said substituents may optionally form a bridge to yield a 3 to 6 membered ring; R¹ is a hydrogen atom or a fluorine atom; R² and R³ is a methyl group; R⁴ is a hydrogen atom; and R⁵ is a carboxy group or a tetrazolyl group.

Preferred classes of compounds of the present invention are those compounds of formula (I) or a pharmaceutically acceptable salt thereof, each as described herein, in which:

(a) A is a $C_1$-$C_2$ alkylene group, said alkylene group being unsubstituted or substituted with 1 to 4 substituents independently selected from the group consisting of a $C_1$-$C_4$ alkyl group, a hydroxy-$C_1$-$C_4$ alkyl group and a $C_1$-$C_2$ alkoxy-$C_1$-$C_4$ alkyl group, wherein 2 of said substituents may optionally form a bridge to yield a 3 to 6 membered ring; R¹ is a hydrogen atom, a halogen atom or a $C_1$-$C_4$ alkyl group;

(b) A is a $C_1$-$C_2$ alkylene group, said alkylene group being unsubstituted or substituted with 1 to 2 substituents independently selected from the group consisting of a $C_1$-$C_4$ alkyl group, a hydroxy-$C_1$-$C_4$ alkyl group and a $C_1$-$C_2$ alkoxy-$C_1$-$C_4$ alkyl group, wherein 2 of said substituents may optionally form a bridge to yield a 3 to 6 membered ring;

(c) A is a $C_1$-$C_2$ alkylene group, said alkylene group being unsubstituted or substituted with 2 substituents independently selected from the group consisting of a $C_1$-$C_4$ alkyl group and a hydroxy-$C_1$-$C_4$ alkyl group, wherein 2 of said substituents may optionally form a bridge to yield a 3 to 6 membered ring;

(d) A is a $C_1$-$C_2$ alkylene group, said alkylene group being unsubstituted or substituted with 2 substituents independently selected from the group consisting of a $C_1$-$C_2$ alkyl group and a hydroxy-$C_1$-$C_2$ alkyl group, wherein 2 of said substituents may optionally form a bridge to yield a 4 to 6 membered ring; $R^1$ is a hydrogen atom or a fluorine atom;

(e) A is

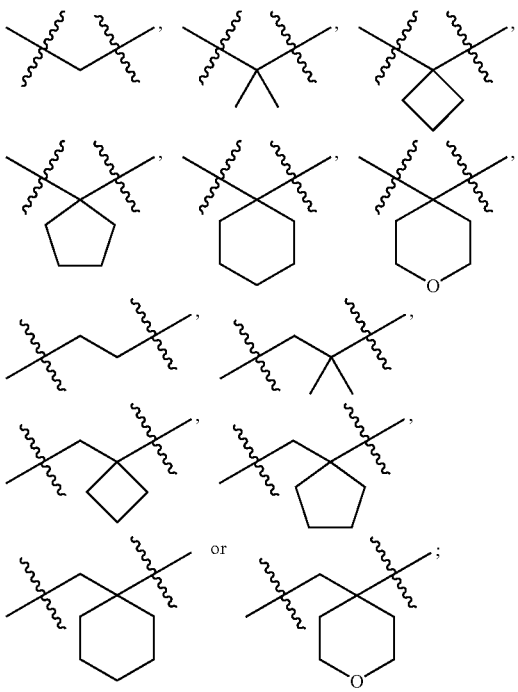

(f) A is

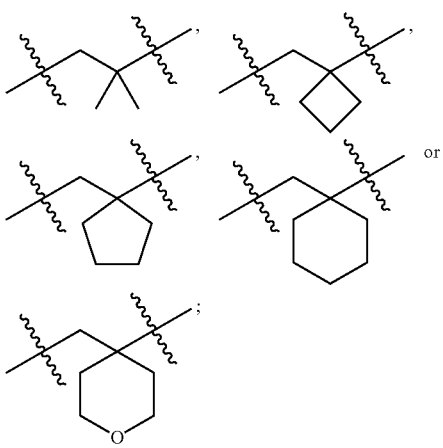

(g) $R^1$ is a hydrogen atom or a halogen atom;
(h) $R^1$ is a hydrogen atom or a fluorine atom;
(i) $R^2$ and $R^3$ is a methyl group, or $R^2$ and $R^3$ may together form a tetramethylene bridge to yield 5 membered ring;
(j) $R^2$ and $R^3$ is a methyl group;
(k) $R^4$ is a hydrogen atom;
(l) $R^5$ is a carboxy group, a tetrazolyl group, a 5-oxo-1,2,4-oxadiazole-3-yl group or a 5-oxo-1,2,4-thiadiazole-3-yl group;
(m) $R^5$ is a carboxy group or a tetrazolyl group.

Of these classes of compounds, any combination among (a) to (m) is also preferred.

One embodiment of the invention provides a compound selected from the group consisting of:
1-{[4-({[(3,3-dimethyl-2-oxo-2,3-dihydro-1H-indol-1-yl) carbonyl]amino}methyl)piperidin-1-yl] methyl}cyclobutanecarboxylic acid;
1-{[4-({[(6-fluoro-3,3-dimethyl-2-oxo-2,3-dihydro-1H-indol-1-yl)carbonyl]amino}methyl)piperidin-1-yl] methyl}cyclobutanecarboxylic acid;
3-[4-({[(6-fluoro-3,3-dimethyl-2-oxo-2,3-dihydro-1H-indol-1-yl)carbonyl]amino}methyl)piperidin-1-yl]-2,2-di methylpropanoic acid;

and a pharmaceutically acceptable salt thereof.

Pharmaceutically acceptable salts of a compound of formula (I) include the acid addition salts and base salts (including disalts) thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002). A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionization in the salt may vary from completely ionized to almost non-ionized.

The compounds of the invention may exist in both unsolvated and solvated forms. The term "solvate" is used herein to describe a molecular complex comprising a compound of the invention and one or more pharmaceutically acceptable solvent molecules, for example, ethanol. The term 'hydrate' is employed when said solvent is water.

Pharmaceutically acceptable solvates in accordance with the invention include hydrates and solvates wherein the solvent of crystallization may be isotopically substituted, e.g. $D_2O$, $d_6$-acetone, $d_6$-DMSO.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see *J Pharm Sci*, 64 (8), 1269-1288 by Haleblian (August 1975).

Hereinafter all references to a compound of formula (I) include references to salts and complexes thereof and to solvates and complexes of salts thereof.

The term "compound of the invention" or "compounds of the invention" refers to, unless indicated otherwise, a compound of formula (I) as hereinbefore defined, polymorphs, prodrugs, and isomers thereof (including optical, geometric and tautomeric isomers) as hereinafter defined and isotopically-labeled compounds of formula (I).

Also within the scope of the invention are so-called 'prodrugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as "prodrugs". Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985). Some examples of prodrugs in accordance with the invention include:

(i) where the compound of formula (I) contains a carboxylic acid functionality, (—COOH), an ester thereof, for example, replacement of the hydrogen with ($C_1$-$C_8$) alkyl;

(ii) where the compound of formula (I) contains an alcohol functionality (—OH), an ether thereof, for example, replacement of the hydrogen with ($C_1$-$C_6$)alkanoyloxymethyl.

Further examples of replacement groups in accordance with the foregoing examples and examples of other prodrug types may be found in the aforementioned references.

Finally, certain compounds of formula (I) may themselves act as prodrugs of other compounds of formula (I).

Compounds of formula (I) containing one or more asymmetric carbon atoms can exist as two or more stereoisomers. Where the compound contains, for example, a keto or oxime group or an aromatic moiety, tautomeric isomerism ("tautomerism") can occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

The present invention includes all pharmaceutically acceptable isotopically-labeled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus such as $^{32}P$, and sulphur, such as $^{35}S$.

Certain isotopically-labeled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

All of the compounds of the formula (I) can be prepared by the procedures described in the general methods presented below or by the specific methods described in the Examples section and the Preparations section, or by routine modifications thereof. The present invention also encompasses any one or more of these processes for preparing the compounds of formula (I), in addition to any novel intermediates used therein.

General Synthesis

The compounds of the present invention may be prepared by a variety of processes well known for the preparation of compounds of this type, for example as shown in the following Methods A to I.

The following Methods A and B illustrate the preparation of compounds of formula (I). Methods C through I illustrate the preparation of various intermediates.

Unless otherwise indicated, $R^1$, $R^2$, $R^3$, $R^4$, $R^5$ and A in the following Methods are as defined above. The term "protecting group", as used hereinafter, means a hydroxy, carboxy or amino-protecting group which is selected from typical hydroxy, carboxy or amino-protecting groups described in *Protective Groups in Organic Synthesis* edited by T. W. Greene et al. (John Wiley & Sons, 1999). All starting materials in the following general syntheses may be commercially available or obtained by conventional methods known to those skilled in the art, such as Howard, Harry R. et al., *J. Med. Chem.*, 1996, 39, 143; Joensson, N et al., *Acta Chem. Scand. Ser. B*, 1974, 28, 225; Robertson, David W et al., *J. Med. Chem.*, 1986, 29, 1832; Quallich, George J et al., *Synthesis*, 1993, 351 and the disclosures of which are incorporated herein by references.

Method A

This illustrates the preparation of compounds of formula (I).

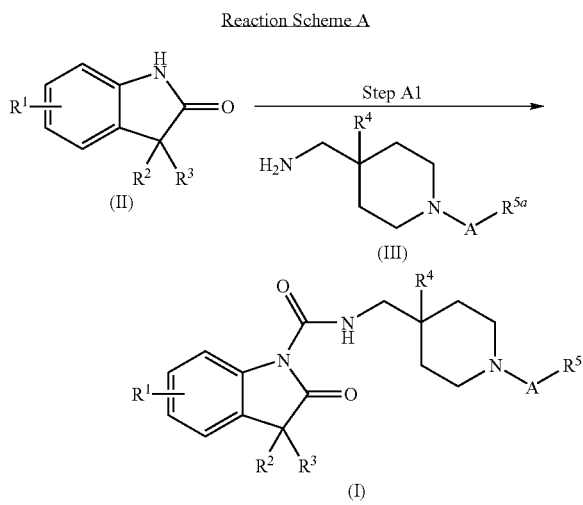

Reaction Scheme A

In Reaction Scheme A, $R^{5a}$ is $R^5$ as defined above or a group of formula —$COOR^6$, wherein $R^6$ is a carboxy-protecting group.

The term "carboxy-protecting group", as used herein, signifies a protecting group capable of being cleaved by chemical means, such as hydrogenolysis, hydrolysis, electrolysis or photolysis, and such carboxy-protecting groups are described in *Protective Groups in Organic Synthesis* edited by T. W. Greene et al. (John Wiley & Sons, 1999). Typical carboxy-protecting groups include, but are not limited to: methyl, ethyl, t-butyl, methoxymethyl, 2,2,2-trichloroethyl, benzyl, diphenylmethyl, trimethylsilyl, t-butyldimethylsilyl and allyl. Of these groups, t-butyl, ethyl or methyl is preferred.

Step A1

In this step, the desired compound of formula (I) of the present invention is prepared by carbonylation of the compound of formula (II) with the compound of formula (III). The compound of formula (II) is commercially available or can be prepared according to the Methods C and D set forth below. The compound of formula (III) can be prepared according to Methods E to G set forth below.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; aromatic hydrocarbons, such as benzene, toluene and nitrobenzene; ethers, such as diethyl ether, diisopropyl ether, tetrahydrofuran and dioxane; and amides, such as N,N-dimethylformamide and N,N-dimethylacetamide. Of these solvents, dichloromethane is preferred.

There is likewise no particular restriction on the nature of the carbonylating agents used, and any carbonylating agent commonly used in reactions of this type may equally be used here. Examples of such carbonylating agents include, but are not limited to: an imidazole derivative such as N,N'-carbonyldiimidazole (CDI); a chloroformate such as trichloromethyl chloroformate and 4-nitrophenyl chloroformate; urea; and triphosgene. Of these, 4-nitrophenyl chloroformate is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

In the case where $R^{5a}$ is a group of formula —$COOR^6$, the deprotection reaction will follow to yield a carboxy group. This reaction is described in detail by T. W. Greene et al., *Protective Groups in Organic Synthesis*, 369-453, (1999), the disclosures of which are incorporated herein by reference. The following exemplifies a typical reaction involving the protecting group t-butyl.

The deprotection reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; and aromatic hydrocarbons, such as benzene, toluene and nitrobenzene. Of these solvents, halogenated hydrocarbons are preferred.

The deprotection reaction is carried out in the presence of an acid. There is likewise no particular restriction on the nature of the acids used, and any acid commonly used in reactions of this type may equally be used here. Examples of such acids include, but are not limited to: acids, such as hydrochloric acid, acetic acid p-toluenesulfonic acid or trifluoroacetic acid. Of these, trifluoroacetic acid is preferred.

The deprotection reaction may be carried out in the presence of a radical scavenger. There is likewise no particular restriction on the nature of the radical scavenger used, and any radical scavenger commonly used in reactions of this type may equally be used here. Examples of such radical scavengers include, but are not limited to: HBr, dimethylsulfoxide or $(CH_3CH_2)_3SiH$. Of these, $(CH_3CH_2)_3SiH$ is preferred.

The deprotection reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

Method B

This illustrates the preparation of compounds of formula (I).

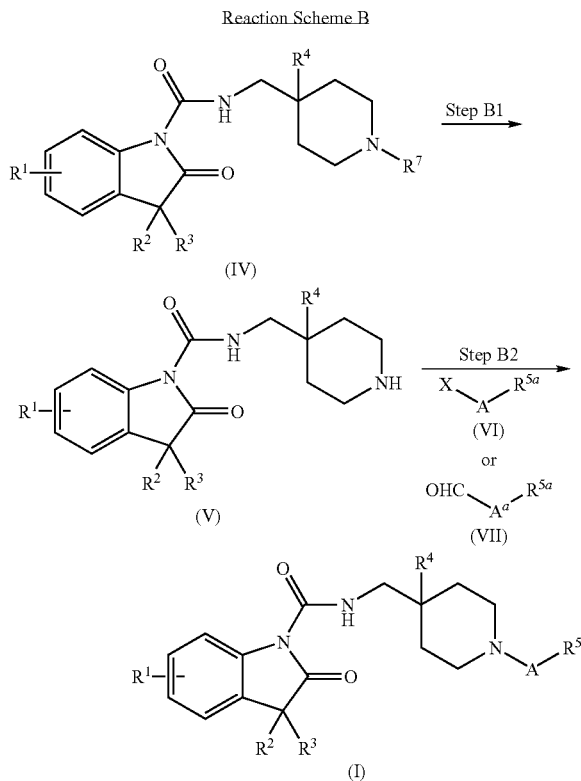

Reaction Scheme B

In Reaction Scheme B, $R^{5a}$ is as defined above; $R^7$ is an amino-protecting group; $A^a$ is A as defined above or a $C_1$-$C_3$ alkylene group, said alkylene group being unsubstituted or substituted with 1 to 4 substituents independently selected from the group consisting of a halogen atom, a $C_1$-$C_4$ alkyl group, a hydroxy-$C_1$-$C_4$ alkyl group and a $C_1$-$C_2$ alkoxy-$C_1$-$C_4$ alkyl group, wherein 2 of said substituents may optionally be taken together with the carbon atom(s) to form a 3 to 6 membered ring; and X is a halogen atom such as an iodine atom, a chlorine atom or a bromine atom.

The term "amino-protecting group", as used herein, signifies a protecting group capable of being cleaved by chemical means, such as hydrogenolysis, hydrolysis, electrolysis or photolysis, and such amino-protecting groups are described in *Protective Groups in Organic Synthesis* edited by T. W. Greene et al. (John Wiley & Sons, 1999). Typical amino-protecting groups include, but are not limited to, benzyl, $C_2H_5O(C=O)$—, $CH_3(C=O)$—, t-butyidimethylsilyl, t-butyldiphenylsilyl, benzyloxycarbonyl and t-butoxycarbonyl. Of these groups, t-butoxycarbonyl is preferred.

Step B1

In this step, the compound of formula (V) is prepared by the deprotection of the compound of formula (IV), which may be prepared, for example, by a method similar to that described in Method A for the preparation of the compound of formula (I) from a compound of formula (II). This deprotection method is described in detail by T. W. Greene et al. [*Protective Groups in Organic Synthesis*, 494-653, (1999)], the disclosures of which are incorporated herein by reference. The following exemplifies a typical method involving the protecting group t-butoxycarbonyl.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; and alcohols, such as methanol, ethanol, propanol, 2-propanol and butanol. Of these solvents, alcohols are preferred.

The reaction is carried out in the presence of excess amount of an acid. There is likewise no particular restriction on the nature of the acids used, and any acid commonly used in reactions of this type may equally be used here. Examples of such acids include, but are not limited to: acids, such as hydrochloric acid, or trifluoroacetic acid. Of these, hydrochloric acid is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

Step B2

In this step, the desired compound of formula (I) is prepared by the coupling (B2-a) of the compound of formula (V) prepared as described in Step B1 with the compound of formula (VI) or by the reductive amination (B2-b) of the compound of formula (V) with the compound of formula (VII).

(B2-a) Coupling with the Compound of Formula (VI):

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; ethers, such as diethyl ether, diisopropyl ether, tetrahydrofuran and dioxane; amines, such as N-methylmorpholine, triethylamine, tripropylamine, tributylamine, diisopropylethylamine, dicyclohexylamine, N-methylpiperidine, N-methylpyrrolidine, pyridine, 4-pyrrolidinopyridine, N,N-dimethylaniline and N,N-diethylaniline; and amides, such as N,N-dimethylformamide and N,N-dimethylacetamide. Of these, N,N-dimethylformamide or N-methylpyrrolidine is preferred.

The reaction is carried out in the presence of a base. There is likewise no particular restriction on the nature of the base used, and any base commonly used in reactions of this type may equally be used here. Examples of such bases include, but are not limited to: amines, such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU); alkali metal hydrides, such as lithium hydride, sodium hydride and potassium hydride; and alkali metal alkoxides, such as sodium methoxide, sodium ethoxide, potassium t-butoxide. Of these, diisopropylethylamine is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 48 hours will usually suffice.

(B2-b) Reductive Amination:

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; ethers, such as diethyl ether, diisopropyl ether, dimethoxyethane, tetrahydrofuran and dioxane; alcohols, such as methanol, ethanol, propanol, 2-propanol and butanol; acetic acid; and water. Of these solvents, halogenated hydrocarbons are preferred.

The reaction is carried out in the presence of a reducing reagent. There is likewise no particular restriction on the nature of the reducing reagents used, and any reducing reagent commonly used in reactions of this type may equally be used here. Examples of such reducing reagent include, but are not limited to: sodium borohydride, sodium cyanoborohydride and sodium triacetoxyborohydride. Of these, sodium triacetoxyborohydride is preferred. The quantity of the reducing reagent required for the reaction may also vary widely, depending on many factors, notably the reaction temperature and the nature of the starting materials and solvent employed. However, that the reaction is effected under preferred conditions, a chemical equivalent ratio of 1 to 3 of the reducing reagent to the starting material will usually suffice.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −20° C. to about 60° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

In the case where $R^{5a}$ is a group of formula —$COOR^6$, the deprotection reaction will follow to yield a carboxy group. The reaction may be carried out under the same conditions as described in Step A1 of Method A.

Method C

This illustrates the preparation of compounds of formula (II).

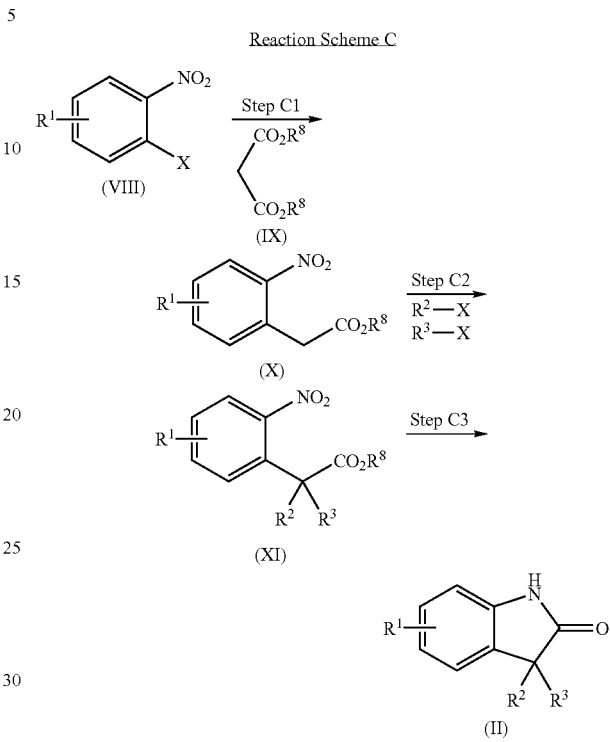

Reaction Scheme C

In Reaction Scheme C, $R^8$ is a $C_1$-$C_4$ alkyl group, preferably methyl or ethyl; and X is as defined above.

Step C1

In this step, the compound of formula (X) is prepared by coupling (C1-a) of the compound of formula (VIII) and the compound of formula (IX) followed by decarboxylation (C1-b) of the resulting compound. The compound of formula (VIII) and the compound of formula (IX) are commercially available.

(C1-a) Coupling with the Compound of Formula (VIII)

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; amides, such as formamide, N,N-dimethylformamide, N,N-dimethylacetamide and hexamethylphosphoric triamide; and sulfoxides, such as dimethyl sulfoxide and sulfolane. Of these solvents, N,N-dimethylsulfoxide is preferred.

The reaction is carried out in the presence of a base. There is likewise no particular restriction on the nature of the bases used, and any base commonly used in reactions of this type may equally be used here. Examples of such bases include: alkali metal hydrides, such as lithium hydride, sodium hydride and potassium hydride; alkali metal alkoxides, such as sodium methoxide, sodium ethoxide and potassium t-butoxide; alkali metal carbonates, such as lithium carbonate, sodium carbonate and potassium carbonate; and alkali metal amides, such as lithium amide, sodium amide, potassium amide, lithium diisopropyl amide, potassium diisopropyl amide, sodium diisopropyl amide, lithium bis(trimethylsilyl) amide and potassium bis(trimethylsilyl)amide. Of these, sodium hydride is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 20° C. to about 200° C. The time required for the reaction may also vary widely, depending on many factors, notably the reaction temperature and the nature of the starting materials and solvent employed. However, provided that the reaction is effected under the preferred conditions outlined above, a period of from about 10 minutes to about 24 hours, will usually suffice.

(C1-b)decarboxylation

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; amides, such as formamide, N,N-dimethylformamide, N,N-dimethylacetamide and hexamethylphosphoric triamide; and sulfoxides, such as dimethyl sulfoxide and sulfolane. Of these solvents, N,N-dimethylsulfoxide is preferred.

The reaction is effected in the presence of metal halide and water. There is no particular restriction on the nature of the metal halide to be employed, provided that it has no adverse effect on the reaction at least to some extent. Examples of metal halide include: lithium chloride, potassium chloride, sodium chloride and sodium iodide. Of these lithium chloride is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 50° C. to about 200° C. The time required for the reaction may also vary widely, depending on many factors, notably the reaction temperature and the nature of the starting materials and solvent employed. However, provided that the reaction is effected under the preferred conditions outlined above, a period of from about 10 minutes to about 24 hours, will usually suffice.

Step C2

In this step, the compound of formula (XI) is prepared by alkylation of the compound of formula (X) with the compounds of formula $R^2$—X and $R^3$—X.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; amides, such as formamide, N,N-dimethylformamide, N,N-dimethylacetamide and hexamethylphosphoric triamide; and sulfoxides, such as dimethyl sulfoxide and sulfolane. Of these solvents, N,N-dimethylformamide is preferred.

The reaction is carried out in the presence of a base. There is likewise no particular restriction on the nature of the bases used, and any base commonly used in reactions of this type may equally be used here. Examples of such bases include: alkali metal hydrides, such as lithium hydride, sodium hydride and potassium hydride; alkali metal alkoxides, such as sodium methoxide, sodium ethoxide and potassium t-butoxide; alkali metal carbonates, such as lithium carbonate, sodium carbonate and potassium carbonate; alkali metal amides, such as lithium amide, sodium amide, potassium amide, lithium diisopropyl amide, potassium diisopropyl amide, sodium diisopropyl amide, lithium bis(trimethylsilyl) amide and potassium bis(trimethylsilyl)amide; and organic lithiums, such as n-butyl lithium, sec-butyl lithium, t-butyl lithium and phenyl lithium. Of these, sodium hydride or n-butyl lithium is preferred.

The reaction may be conducted in the presence or absence of additives such as 16-crown-6, N,N,N',N'-tetramethylethylene diamine (TMEDA) and hexamethylphosphoric triamide (HMPA). Of these additives, 16-crown-6 or TMEDA is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 50° C. to about 200° C. The time required for the reaction may also vary widely, depending on many factors, notably the reaction temperature and the nature of the starting materials and solvent employed. However, provided that the reaction is effected under the preferred conditions outlined above, a period of from about 10 minutes to about 24 hours, will usually suffice.

Step C3

In this step, the compound of formula (II) is prepared by annealing of the compound of formula (XI) under the reductive condition.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: alcohols, such as methanol, ethanol, propanol, 2-propanol and butanol; and esters, such as ethyl acetate and propyl acetate. Of these solvents, methanol is preferred.

The reaction is carried out in the presence of a reducing agent. There is likewise no particular restriction on the nature of the reducing agents used, and any reducing agent commonly used in reactions of this type may equally be used here. Examples of such reducing agents include: combinations of a hydrogen supplier, such as hydrogen gas and ammonium formate, and a catalyst, such as palladium-carbon, platinum and Raney nickel; and a combination of metals, such as zinc and iron, and acids, such as hydrochloric acid, acetic acid and acetic acid-ammonium chloride complex. Of these the combination of iron and acetic acid is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 10° C. to about 50° C. in the case employing the combination of the hydrogen supplier and the catalyst as the reducing agent, or from about 50° C. to about 200° C. in the case employing the combination of the metals and acids as the reducing agent. The time required for the reaction may also vary widely, depending on many factors, notably the reaction temperature and the nature of the starting materials and solvent employed. However, provided that the reaction is effected under the preferred conditions outlined above, a period of from about 10 minutes to about 24 hours, will usually suffice.

Method D

This illustrates the preparation of compounds of formula (II).

Reaction Scheme D

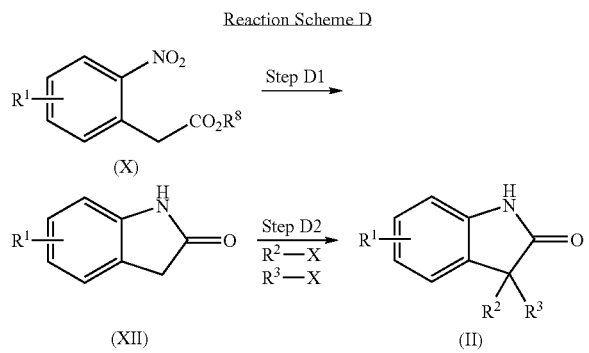

In Reaction Scheme D, $R^8$ and X are each as defined above.

Step D1

In this step, the compound of formula (XII) is prepared by annealing of the compound of formula (X) which is commercially available or prepared according to Step C1 of Method C. The reaction may be carried out under the same conditions as described in Step C3 of Method C.

Step D2

In this step, the compound of formula (II) is prepared by alkylation of the compound of formula (XII) with the compounds of formula $R^2$—X and $R^3$—X. The reaction may be carried out under the same conditions as described in Step C2 of Method C.

Method E

This illustrates the preparation of the compound of formula (III).

Reaction Scheme E

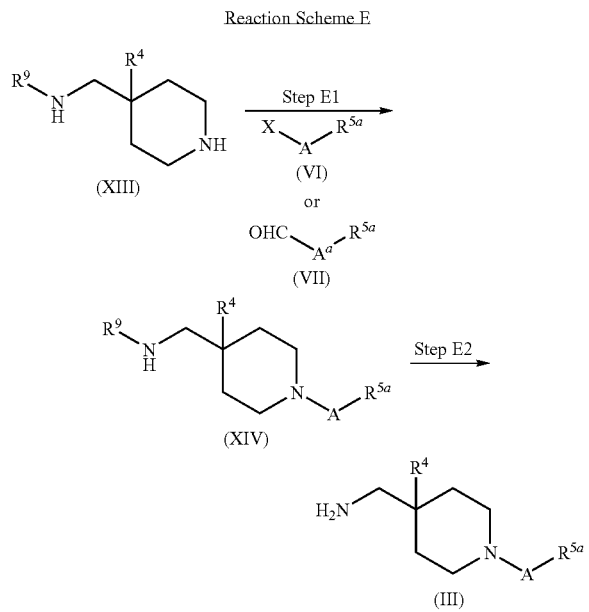

In Reaction Scheme E, X, $A^a$, and $R^{3a}$ are each as defined above; and $R^9$ is an amino-protecting group.

Step E1

In this step, the compound of formula (XIV) is prepared by the coupling of the compound of formula (XIII) with a compound of formula (VI) or by the reductive amination of the compound of formula (XIII) with the compound of formula (VII). The compound of formula (XIII) can be prepared according to Methods H and I set forth below or is commercially available.

Step E2

In this step, the compound of formula (III) is prepared by the deprotection of the compound of formula (XIV) prepared as described in Step E1. The reaction may be carried out under the same conditions as described in Step B1 of Method B.

Method F

This illustrates the preparation of the compound of formula (III) wherein A is $A^b$.

Reaction Scheme F

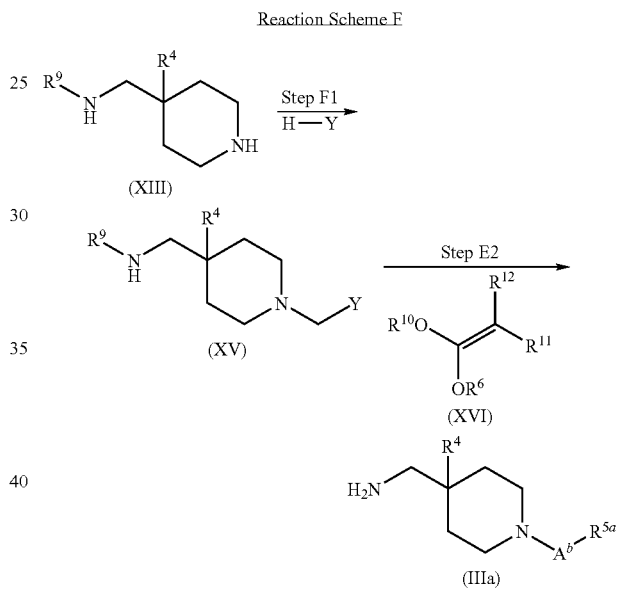

In Reaction Scheme F, $R^{5a}$, $R^6$ and $R^9$ are each as defined above; $R^{10}$ is a silyl group such as t-butyldimethylsilyl, t-butyldiphenylsilyl, triethylsilyl or trimethylsilyl, preferably trimethylsilyl; $R^{11}$ and $R^{12}$ independently represent a halogen atom, a $C_1$-$C_4$ alkyl group, a hydroxy-$C_1$-$C_4$-alkyl group and an $C_1$-$C_2$ alkoxy-$C_1$-$C_4$ alkyl group, wherein $R^{11}$ and $R^{12}$ may optionally be taken together with the carbon atom to which they are attached to form a 3 to 6 membered ring; $A^b$ is A as defined above with proviso a methylene group and a substituted methylene group are excluded; and Y is an alkoxy group having 1 to 4 carbon atoms, an imidazolyl group or a pthalimidyl group.

Step F1

In this step, the compound of formula (XV) is prepared by condensation of the compound of formula (XIII) with the compound of formula H—Y in the presence of paraformaldehyde. A compound of formula (XIII) can be prepared according to Method H and I or is commercially available.

In the case that Y is not an alkoxy group, the reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; and alcohols, such as methanol, ethanol, propanol, 2-propanol and butanol. Of these, dichloromethane or ethanol is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 48 hours, will usually suffice.

Step F2

In this step, the compound of formula (IIIa) is prepared by Mannich reaction of the compound of formula (XV) with the compound of formula (XVI).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; ethers, such as diethyl ether, diisopropyl ether, tetrahydrofuran and dioxane; nitriles, such as acetonitrile and benzonitrile; and amides, such as formamide, N,N-dimethylformamide, N,N-dimethylacetamide and hexamethylphosphoric triamide. Of these solvents, dichloromethane is preferred.

The reaction is carried out in the presence of a Lewis acid. There is likewise no particular restriction on the nature of the Lewis acids used, and any Lewis acid commonly used in reactions of this type may equally be used here. Examples of such Lewis acid include, but are not limited to: $BF_3$, $AlCl_3$, $FeCl_3$, $MgCl_2$, $AgCl$, $Fe(NO_3)_3$, $CF_3SO_3Si(CH_3)_3$, $Yb(CF_3SO_3)_3$ and $SnCl_4$. Of these, $Yb(CF_3SO_3)_3$, $CF_3SO_3Si(CH_3)_3$ or $MgCl_2$ is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

Method G

This illustrates the preparation of the compound of formula (III) wherein $R^4$ is a hydrogen atom and A is $A^b$.

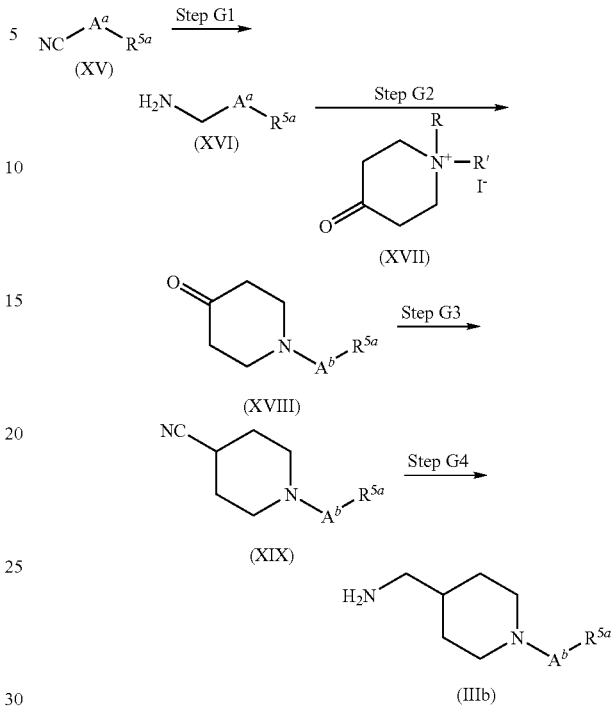

In Reaction Scheme G, $A^a$, $A^b$ and $R^{5a}$ are each as defined above; each of R and R' is a $C_1$-$C_4$ alkyl group, preferably a methyl group, or an aralkyl group such as a benzyl or phenethyl group, preferably a benzyl group.

Step G1

In this step, the compound of formula (XVI) is prepared by reduction of the cyano group of the compound of formula (XV), which is commercially available.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: ethers, such as diethyl ether, diisopropyl ether, tetrahydrofuran and dioxane; aromatic hydrocarbons, such as benzene, toluene and nitrobenzene; and alcohols, such as methanol, ethanol, propanol, 2-propanol and butanol. Of these, methanol is preferred.

The reaction is carried out in the presence of a reducing agent. There is likewise no particular restriction on the nature of the reducing agents used, and any reducing agent commonly used in reactions of this type may equally be used here. Examples of such reducing agents include, but are not limited to: metal borohydrides such as sodium borohydride and sodium cyanoborohydride; combinations of hydrogen gas and a catalyst such as palladium-carbon, platinum and Raney nickel; and hydride compounds such as lithium aluminum hydride, and diisobutyl aluminum hydride. Of these, Raney nickel is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

Step G2

In this step, the compound of formula (XVIII) is prepared by reacting a compound of formula (XVII), which is commercially available, with a compound of formula (XVI).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: water; and alcohols, such as methanol, ethanol, propanol, 2-propanol and butanol. Of these, a mixture of water and ethanol is preferred.

The reaction is carried out in the presence of a base. There is likewise no particular restriction on the nature of the base used, and any base commonly used in reactions of this type may equally be used here. Examples of such bases include, but are not limited to: alkali metal hydroxides, such as lithium hydroxide, sodium hydroxide and potassium hydroxide; alkali metal alkoxides, such as sodium methoxide, sodium ethoxide, potassium t-butoxide; and alkali metal carbonates, such as lithium carbonate, sodium carbonate and potassium carbonate. Of these, potassium carbonate is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

Step G3

In this step, the compound of formula (XIX) is prepared by converting the oxo group of the compound of formula (XVIII) to a cyano group in the presence of p-toluenesulfonylmethyl isocyanide.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: ethers, such as diethyl ether, diisopropyl ether, ethylene glycol dimethyl ether, tetrahydrofuran and dioxane; and alcohols, such as methanol, ethanol, propanol, 2-propanol and butanol. Of these, a mixture of ethylene glycol dimethyl ether and ethanol is preferred.

The reaction is carried out in the presence of a base. There is likewise no particular restriction on the nature of the base used, and any base commonly used in reactions of this type may equally be used here. Examples of such bases include, but are not limited to: alkali metal alkoxides, such as sodium methoxide, sodium ethoxide and potassium t-butoxide. Of these, potassium t-butoxide is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

Step G4

In this step, the compound of formula (IIIb) is prepared by reduction of the cyano group of the compound of formula (XIX). The reaction may be carried out under the same conditions as described in Step G1 of Method G.

Method H

This illustrates the preparation of compounds of formula (XIII) wherein $R^4$ is a halogen atom.

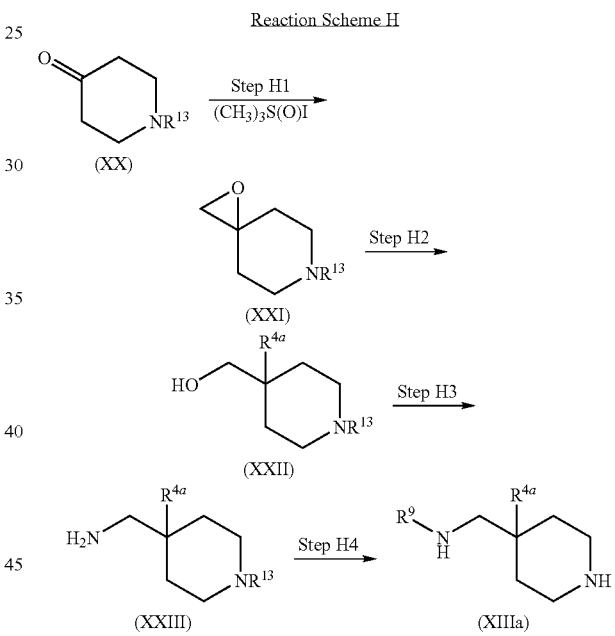

Reaction Scheme H

In Reaction Scheme H, $R^{4a}$ is a halogen atom; $R^9$ is as defined above; and $R^{13}$ is an amino-protecting group, preferably a benzoyl group.

Step H1

In this step, the compound of formula (XXI) is prepared by converting the carbonyl group of the compound of formula (XX) into the epoxide group.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: amides, such as formamide, N,N-dimethylformamide, N,N-dimethylacetamide and hexamethylphosphoric triamide; sulfoxide such as dimethyl sulfoxide or sulfolane. Of these solvents, dimethyl sulfoxide is preferred.

The reaction is carried out in the presence of a base. There is likewise no particular restriction on the nature of the base used, and any base commonly used in reactions of this type may equally be used here. Examples of such bases include, but are not limited to: alkali metal alkoxides, such as sodium methoxide, sodium ethoxide and potassium t-butoxide; and alkali metal carbonates, such as lithium carbonate, sodium carbonate and potassium carbonate. Of these, potassium t-butoxide is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Step H2

In this step, the compound of formula (XXII) is prepared by reacting a hydrogen halide with the compound of formula (XXI).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: ethers, such as diethyl ether, diisopropyl ether, tetrahydrofuran and dioxane; amides, such as formamide, N,N-dimethylformamide, N,N-dimethylacetamide and hexamethylphosphoric triamide. Of these solvents, tetrahydrofuran is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Step H3

In this step, the compound of formula (XXIII) is prepared by reaction of the compound of formula (XXII) with sodium azide (H3-a) followed by the reduction of the azide group (H3-b).

(H3-a) Reaction with Sodium Azide:

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; ethers, such as diethyl ether, diisopropyl ether, tetrahydrofuran and dioxane; amides, such as formamide, N,N-dimethylformamide, N,N-dimethylacetamide and hexamethylphosphoric triamide; and sulfoxide such as dimethyl sulfoxide and sulfolane. Of these solvents, N,N-dimethylformamide is preferred.

Before adding sodium azide, the hydroxy group is converted to a leaving group, such as a methylsulfonyl group, a trifluoromethylsulfonyl group and 4-methyl phenylsulfonyl group by adding reagents, such as trifluoromethanelsulfonylchloride, mesyl chloride and tosyl chloride. Of these reagents, mesyl chloride is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

(H3-b) Reduction:

The reaction may be carried out under the same conditions as described in Step G1 of Method G.

Step H4

In this step, the compound of formula (XIIIa) is prepared by introducing the amino-protecting group $R^9$ to the primary amino group (H4-a) and selectively deprotecting the amino-protecting group $R^{13}$ of the secondary amino group (H4-b).

(H4-a) Introduction of the Amino-Protecting Group:

This reaction is described in detail by T. W. Greene et al. [*Protective Groups in Organic Synthesis*, 494-653, (1999)], the disclosures of which are incorporated herein by reference. The following exemplifies a typical reaction involving the protecting group t-butoxycarbonyl.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: water; ethers, such as diethyl ether, diisopropyl ether, tetrahydrofuran and dioxane; and sulfoxide such as dimethyl sulfoxide and sulfolane. Of these solvents, tetrahydrofuran is preferred.

The reaction is carried out in the presence of reagent. There is likewise no particular restriction on the nature of the reagents used, and any reagent commonly used in reactions of this type may equally be used here. Examples of such reagents include, but are not limited to: di-t-butyl carbonate and 1-(t-butoxycarbonyl)benztriazole. Of these, di-t-butyl carbonate is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120°. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

(H4-b) Deprotection:

This method is described in detail by T. W. Greene et al., *Protective Groups in Organic Synthesis*, 494-653, (1999), the disclosures of which are incorporated herein by reference. The following exemplifies a typical method involving the benzoyl protecting group in the presence of combinations of hydrogen gas and a catalyst such as palladium-carbon or platinum.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; alcohols, such as methanol, ethanol, propanol, 2-propanol and butanol; and ethers, such as diethyl ether, diisopropyl ether, tetrahydrofuran and dioxane. Of these solvents, methanol is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

Method I

This illustrates the preparation of compounds of formula (XIII) wherein $R^4$ is a hydroxy group.

Reaction Scheme I

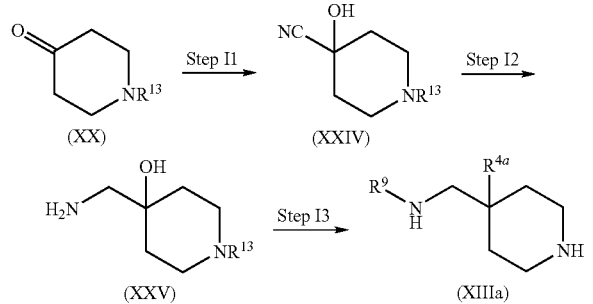

In Reaction Scheme I, $R^9$ and R13 are each as defined above.

Step I1

In this step, the compound of formula (XXIV) is prepared by reacting the carbonyl group of the compound of formula (XX), which is commercially available, with trimethylsilyl cyanide.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: aromatic hydrocarbons, such as benzene, toluene and nitrobenzene; halogenated hydrocarbons, such as dichloromethane, chloroform, carbon tetrachloride and 1,2-dichloroethane; ethers, such as diethyl ether, diisopropyl ether, ethylene glycol dimethyl ether, tetrahydrofuran and dioxane; nitriles, such as acetonitrile and benzonitrile; and alcohols, such as methanol, ethanol, propanol, 2-propanol and butanol. Of these, toluene is preferred.

The reaction is carried out in the presence of a reagent. There is likewise no particular restriction on the nature of the reagents used, and any reagent commonly used in reactions of this type may equally be used here. Examples of such reagent include, but are not limited to: Lewis acids, such as $BF_3$, $AlCl_3$, $FeCl_3$, $AgCl$, $ZnI_2$, $Fe(NO_3)_3$, $CF_3SO_3Si(CH_3)_3$, $Yb(CF_3SO_3)_3$ and $SnCl_4$; bases, such as CaO; ethers, such as 18-crown-6; acids, such as Amberlite XAD-4 resin. Of these, $ZnI_2$ is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

Step I2

In this step, the compound of formula (XXV) is prepared by converting the cyano group of the compound of formula (XXII) to an amino group. The reaction may be carried out under the same conditions as described in Step G1 of Method.

Step I3

In this step, the compound of formula (XIIIa) is prepared by protecting and deprotecting the amino groups of the compound of formula (XXV). The reaction may be carried out under the same conditions as described in Step H4 of Method H.

The compounds of formula (I), and the intermediates above-mentioned preparation methods can be isolated and purified by conventional procedures, such as distillation, recrystallization or chromatographic purification.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, a method of optical resolution of a racemate (or a racemic precursor) can be appropriately selected from conventional procedures, for example, preferential crystallization, or resolution of diastereomeric salts between a basic moiety of the compound of formula (I) and a suitable optically active acid such as tartaric acid.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a pharmaceutical composition or formulation in association with one or more pharmaceutically acceptable carriers or excipients. The term "carrier" or "excipient" is used herein to describe any ingredient other than the compound(s) of the invention. The choice of carrier or excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as, for example, tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include, for example, suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in *Expert Opinion in Therapeutic Patents*, 11 (6), 981-986 by Liang and Chen (2001).

For tablet dosage forms, depending on dose, the drug may make up from about 1 wt % to about 80 wt % of the dosage form, more typically from about 5 wt % to about 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from about 1 wt % to about 25 wt %, preferably from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from about 0.25 wt % to about 10 wt %, preferably from about 0.5 wt % to about 3 wt % of the tablet.

Other possible ingredients include anti-oxidants, colorants, flavoring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "*Pharmaceutical Dosage Forms: Tablets, Vol. 1*", by H. Lieberman and L. Lachman, Marcel Dekker, N.Y., N.Y., 1980 (ISBN 0-8247-6918-X).

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, *Pharmaceutical Technology On-line*, 25(2), 1-14 (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from about 3 to about 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, *J Pharm Sci,* 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from about 1 µg to about 20 mg of the compound of the invention per actuation and the actuation volume may vary from about 1 µl to about 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration. Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from about 1 to about 100 µg of the compound of formula (I). The overall daily dose will typically be in the range about 50 µg to about 20 mg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

The compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in. WO 91/11172, WO 94/02518 and WO 98/55148.

Kit-of-Parts

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

For administration to human patients, the total daily dose of the compounds of the invention is typically in the range of about 0.05 mg to about 100 mg depending, of course, on the mode of administration, preferred in the range of about 0.1 mg to about 50 mg and more preferred in the range of about 0.5 mg to about 20 mg. For example, oral administration may require a total daily dose of from about 1 mg to about 20 mg, while an intravenous dose may only require from about 0.5 mg to about 10 mg. The total daily dose may be administered in single or divided doses.

These dosages are based on an average human subject having a weight of about 65 kg to about 70 kg. The physician will readily be able to determine doses for subjects whose weight falls outside this range, such as infants and the elderly.

As discussed above, a compound of the invention exhibits $5-HT_4$ agonist activity. A $5-HT_4$ agonist of the present invention may be usefully combined with at least one other pharmacologically active agent or compound, particularly in the treatment of gastroesophageal reflux disease. For example, a $5-HT_4$ agonist, particularly a compound of the formula (I), or a pharmaceutically acceptable salt or solvate thereof, as defined above, may be administered simultaneously, sequentially or separately in combination with one or more pharmacologically active agents selected from:

(i) histamine $H_2$ receptor antagonists, e.g. ranitidine, lafutidine, nizatidine, cimetidine, famotidine and roxatidine;

(ii) proton pump inhibitors, e.g. omeprazole, esomeprazole, pantoprazole, rabeprazole, tenatoprazole, ilaprazole and lansoprazole;

(iii) Acid pump antagonists, e.g. soraprazan, revaprazan (YH-1885), AZD-0865, CS-526, AU-2064 and YJA-20379-8;

(iv) oral antacid mixtures, e.g. Maalox®, Aludrox® and Gaviscon®;

(v) mucosal protective agents, e.g. polaprezinc, ecabet sodium, rebamipide, teprenone, cetraxate, sucralfate, chloropylline-copper and plaunotol;

(vi) $GABA_B$ agonists, e.g. baclofen and AZD-3355;

(vii) α2 agonists, e.g. clonidine, medetomidine, lofexidine, moxonidine, tizanidine, guanfacine, guanabenz, talipexole and dexmedetomidine;

(viii) Xanthin derivatives, e.g. Theophylline, aminophylline and doxofylline;

(ix) calcium channel blockers, e.g. aranidipine, lacidipine, falodipine, azelnidipine, clinidipine, lomerizine, diltiazem, gallopamil, efonidipine, nisoldipine, amlodipine, lercanidipine, bevantolol, nicardipine, isradipine, benidipine, verapamil, nitrendipine, barnidipine, propafenone, manidipine, bepridil, nifedipine, nilvadipine, nimodipine, and fasudil;

(x) benzodiazepine agonists, e.g. diazepam, zaleplon, zolpidem, haloxazolam, clonazepam, prazepam, quazepam, flutazolam, triazolam, lormetazepam, midazolam, tofisopam, clobazam, flunitrazepam and flutoprazepam;

(xi) prostaglandin analogues, e.g. Prostaglandin, misoprostol, treprostinil, esoprostenol, latanoprost, iloprost, beraprost, enprostil, ibudilast and ozagrel;

(xii) histamine $H_3$ agonists, e.g. R-alpha-methylhistamine and BP-294;

(xiii) anti-gastric agents, e.g. Anti-gastrin vaccine, itriglumide and Z-360;

(xiv) $5-HT_3$ antagonists, e.g. dolasetron, palonosetron, alosetron, azasetron, ramosetron, mitrazapine, granisetron, tropisetron, E-3620, ondansetron and indisetron;

(xv) tricyclic antidepressants, e.g. imipramine, amitriptyline, clomipramine, amoxapine and lofepramine;

(xvi) GABA agonists, e.g. gabapentin, topiramate, cinolazepam, clonazepam, progabide, brotizolam, zopiclone, pregabalin and eszopiclone;

(xvii) opioid analgesics, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine and pentazocine;

(xviii) somatostatin analogues, e.g. octreotide, AN-238 and PTR-3173;

(xix) Cl Channel activator: e.g. lubiprostone;

(xx) selective serotonin reuptake inhibitors, e.g. sertraline, escitalopram, fluoxetine, nefazodone, fluvoxamine, citalopram, milnacipran, paroxetine, venlafaxine, tramadol, sibutramine, duloxetine, desvenlafaxine and dapoxetine;

(xxi) anticholinergics, e.g. dicyclomine and hyoscyamine;

(xxii) laxatives, e.g. Trifyba®, Fybogel®, Konsyl®, Isogel®, Regulan®, Celevac® and Normacol®;

(xxiii) fiber products, e.g. Metamucil®;

(xxiv) antispasmodics, e.g.: mebeverine;

(xxv) dopamine antagonists, e.g. metoclopramide, domperidone and levosulpiride;

(xxvi) cholinergics, e.g. neostigmine (xxvii) AChE inhibitors, e.g. galantamine, metrifonate, rivastigmine, itopride and donepezil;

(xxviii) Tachykinin (NK) antagonists, particularly NK-3, NK-2 and NK-1 antagonists e.g. nepadutant, saredutant, talnetant, (αR,9R)-7-[3,5-bis(trifluoromethyl)benzyl]-8,9,10,11-tetrahydro-9-methyl-5-(4-methylphenyl)-7H-[1,4]d iazocino[2,1-g][1,7]naphthridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl]methylamino]-2-phenyl-piperidine (2S,3S).

Method for Assessing Biological Activities:

The 5-HT$_4$ receptor binding affinities of the compounds of this invention are determined by the following procedures.

Human 5-HT$_4$ Binding(1)

Human 5-HT$_{4(d)}$ transfected HEK293 cells were prepared and grown in-house. The collected cells were suspended in 50 mM HEPES (pH 7.4 at 4° C.) supplemented with protease inhibitor cocktail (Boehringer, 1:1000 dilution) and homogenized using a hand held Polytron PT 1200 disruptor set at full power for 30 sec on ice. The homogenates were centrifuged at 40,000×g at 4° C. for 30 min. The pellets were then resuspended in 50 mM HEPES (pH 7.4 at 4° C.) and centrifuged once more in the same manner. The final pellets were resuspended in an appropriate volume of 50 mM HEPES (pH 7.4 at 25° C.), homogenized, aliquoted and stored at −80° C. until use. An aliquot of membrane fractions was used for protein concentration determination using BCA protein assay kit (PIERCE) and ARVOsx plate reader (Wallac).

For the binding experiments, 25 µl of test compounds were incubated with 25 µl of [$^3$H]-GR113808 (Amersham, final 0.2 nM) and 150 µl of membrane homogenate and WGA-SPA beads (Amersham) suspension solutions (10 µg protein and 1 mg SPA beads/well) for 60 minutes at room temperature. Nonspecific binding was determined by 1 µM GR113808 (Tocris) at the final concentration. Incubation was terminated by centrifugation at 1000 rpm.

Receptor-bound radioactivity was quantified by counting with MicroBeta plate counter (Wallac).

All compounds of Examples showed 5HT$_4$ receptor affinity.

Human 5-HT$_4$ Binding(2)

Human 5-HT$_{4(d)}$ transfected HEK293 cells were prepared and grown in-house. The collected cells were suspended in 50 mM Tris buffer (pH 7.4 at 4° C.) supplemented with protease inhibitor cocktail (Boehringer, 1:1000 dilution) and homogenized using a hand held Polytron PT 1200 disruptor set at full power for 30 sec on ice. The homogenates were centrifuged at 40,000×g at 4° C. for 10 min. The pellets were then resuspended in 50 mM Tris buffer (pH 7.4 at 4° C.) and centrifuged once more in the same manner. The final pellets were resuspended in an appropriate volume of 50 mM Tris buffer (pH 7.4 at 25° C.) containing 10 mM MgCl$_2$, homogenized, aliquoted and stored at −80° C. until use. An aliquot of membrane fractions was used for protein concentration determination using BCA protein assay kit (PIERCE) and ARVOsx plate reader (Wallac).

For the binding experiments, 50 µl of test compounds were incubated with 50 µl of [$^3$H] 5-HT (Amersham, final 8.0 nM) and 400 µl of membrane homogenate (300 µg protein/tube) for 60 minutes at room temperature. Nonspecific binding was determined by 50 µM GR113808 (Tocris) at the final concentration. All incubations were terminated by rapid vacuum filtration over 0.2% PEI soaked glass fiber filter papers using BRANDEL harvester followed by three washes with 50 mM Tris buffer (pH 7.4 at 25° C.). Receptor-bound radioactivity was quantified by liquid scintillation counting using Packard LS counter.

All compounds of Examples showed 5HT$_4$ receptor affinity.

Agonist-Induced cAMP Elevation in Human 5-HT$_{4(d)}$ Transfected HEK293 Cells

Human 5-HT$_{4(d)}$ transfected HEK293 cells were established in-house. The cells were grown at 37° C. and 5% CO$_2$ in DMEM supplemented with 10% FCS, 20 mM HEPES (pH 7.4), 200 µg/ml hygromycin B (Gibco), 100 units/ml penicillin and 100 µg/ml streptomycin.

The cells were grown to 60-80% confluence. On the previous day before treatment with compounds dialyzed FCS (Gibco) was substituted for normal and the cells were incubated overnight.

Compounds were prepared in 96-well plates (12.5 µl/well). The cells were harvested with PBS/1 mM EDTA, centrifuged and washed with PBS. At the beginning of the assay, cell pellet was resuspended in DMEM supplemented with 20 mM HEPES, 10 µM pargyline (Sigma) and 1 mM 3-isobutyl-1-methylxanthine (Sigma) at the concentration of 1.6×10$^5$ cells/ml and left for 15 minutes at room temperature. The reaction was initiated by addition of the cells into plates (12.5 µl/well). After incubation for 15 minutes at room temperature, 1% Triton X-100 was added to stop the reaction (25 µl/well) and the plates were left for 30 minutes at room temperature. Homogenous time-resolved fluorescence-based cAMP (Schering) detection was made according to the manufacturer's instruction. ARVOsx multilabel counter (Wallac) was used to measure HTRF (excitation 320 nm, emission 665 nm/620 nm, delay time 50 µs, window time 400 µs). Data was analyzed based on the ratio of fluorescence intensity of each well at 620 nm and 665 nm followed by cAMP quantification using cAMP standard curve. Enhancement of cAMP production elicited by each compound was normalized to the amount of cAMP produced by 1000 nM serotonin (Sigma).

All compounds of Examples showed 5HT$_4$ receptor agonistic activity.

TMM Functional Assay

The presence of 5-HT$_4$ receptors in the rat esophagus and the ability to demonstrate partial agonism in the TMM preparation are reported in the literature (See G. S. Baxter et al. Naunyn-Schmiedeberg's Arch Pharmacol (1991) 343: 439-446; M. Yukiko et al. JPET (1997) 283: 1000-1008; and J. J. Reeves et al. Br. J. Pharmacol. (1991) 103: 1067-1072). More specifically, partial agonist activity can be measured according to the following procedures.

Male SD rats (Charles River) weighing 250-350 g were stunned and then killed by cervical dislocation. The esophagus was dissected from immediately proximal to the stomach (including piece of stomach to mark distal end) up to the level of the trachea and then placed in fresh Krebs' solution.

The outer skeletal muscle layer was removed in one go by peeling it away from the underlying smooth muscle layer using forceps (stomach to tracheal direction). The remaining inner tube of smooth muscle was known as the TMM. This was trimmed to 2 cm from the original 'stomach-end' and the rest discarded.

The TMMs were mounted as whole 'open' tubes in longitudinal orientation in 5 ml organ baths filled with warm (32° C.) aerated Krebs. Tissues were placed under an initial tension of 750 mg and allowed to equilibrate for 60 minutes. The tissues were re-tensioned twice at 15 minute intervals during the equilibration period. The pump flow rate was set to 2 ml/min during this time.

Following equilibration, the pump was switched off. The tissues were exposed to 1 µM carbachol and contracted and reached a steady contractile plateau within 15 minutes. Tissues were then subject to 1 µM 5-HT (this was to prime the tissues). The tissues relaxed in response to 5-HT fairly rapidly—within 1 minute. As soon as maximal relaxation has occurred and a measurement taken, the tissues were washed at maximum rate (66 ml/min) for at least 1 minute and until the original baseline (pre-carbachol and 5-HT) has returned (usually, the baseline drops below the original one following initial equilibration). The pump flow rate was reduced to 2 ml/min and the tissues left for 60 minutes.

A cumulative concentration-effect-curve (CEC) to 5-HT was constructed across the range 0.1 nM to 1 µM, in half-log unit increments (5-HT curve 1 for data analysis). Contact time between doses was 3 minutes or until plateau established. Tissues responded quicker as concentration of 5-HT in the bath increases. At the end of the curve, the tissues were washed (at maximum rate) as soon as possible to avoid desensitization of receptors. Pump rate was reduced to 2 ml/min and the tissues left for 60 minutes.

A second CEC was carried out—either to 5-HT (for time control tissues), another 5-HT$_4$ agonist (standard) or a test compound (curve 2 for data analysis). Contact time varied for other 5-HT$_4$ agonists and test compounds and was tailored according to the tissues' individual responses to each particular agent. In tissues exposed to a test compound, a high concentration (1 µM) of a 5-HT$_4$ antagonist (SB 203, 186: 1H-Indole-3-carboxylic acid, 2-(1-piperidinyl)ethyl ester, Tocris) was added to the bath following the last concentration of test compound. This was to see if any agonist-induced relaxation (if present) could be reversed. SB 203,186 reversed 5-HT induced relaxation, restoring the tissue's original degree of carbachol-induced tone.

Agonist activity of test compounds was confirmed by pre-incubating tissues with 100 nM standard 5HT$_4$ antagonist such as SB 203,186. SB 203,186 was added to the bath 5 minutes before the addition of carbachol prior to curve 2. Tissues must be 'paired' for data analysis i.e. the test compound in the absence of SB 203,186 in one tissue was compared with the test compound in the presence of SB 203,186 in a separate tissue. It was not possible to carry out a curve 3 i.e. 5-HT curve 1, followed by the test compound curve 2 (−SB 203,186), followed by the test compound curve 3 (+SB 203,186).

All compounds of Examples showed 5HT$_4$ receptor agonistic activity.

Human Dofetilide Binding

Human HERG transfected HEK293S cells were prepared and grown in-house. The collected cells were suspended in 50 mM Tris-HCl (pH 7.4 at 4° C.) and homogenized using a hand held Polytron PT 1200 disruptor set at full power for 20 sec on ice. The homogenates were centrifuged at 48,000×g at 4° C. for 20 min. The pellets were then resuspended, homogenized, and centrifuged once more in the same manner. The final pellets were resuspended in an appropriate volume of 50 mM Tris-HCl, 10 mM KCl, 1 mM MgCl$_2$ (pH 7.4 at 4° C.), homogenized, aliquoted and stored at −80° C. until use. An aliquot of membrane fractions was used for protein concentration determination using BCA protein assay kit (PIERCE) and ARVOsx plate reader (Wallac).

Binding assays were conducted in a total volume of 200 µl in 96-well plates. Twenty µl of test compounds were incubated with 20 µl of [$^3$H]-dofetilide (Amersham, final 5 nM) and 160 µl of membrane homogenate (25 µg protein) for 60 minutes at room temperature. Nonspecific binding was determined by 10 µM dofetilide at the final concentration. Incubation was terminated by rapid vacuum filtration over 0.5% presoaked GF/B Betaplate filter using Skatron cell harvester with 50 mM Tris-HCl, 10 mM KCl, 1 mM MgCl$_2$, pH 7.4 at 4° C. The filters were dried, put into sample bags and filled with Betaplate Scint. Radioactivity bound to filter was counted with Wallac Betaplate counter.

Caco-2 Permeability

Caco-2 permeability was measured according to the method described in Shiyin Yee, *Pharmaceutical Research*, 763 (1997).

Caco-2 cells were grown on filter supports (Falcon HTS multiwell insert system) for 14 days. Culture medium was removed from both the apical and basolateral compartments and the monolayers were preincubated with pre-warmed 0.3 ml apical buffer and 1.0 ml basolateral buffer for 0.5 hour at 37° C. in a shaker water bath at 50 cycles/min. The apical buffer consisted of Hanks Balanced Salt Solution, 25 mM D-glucose monohydrate, 20 mM MES Biological Buffer, 1.25 mM CaCl$_2$ and 0.5 mM MgCl$_2$ (pH 6.5). The basolateral buffer consisted of Hanks Balanced Salt Solution, 25 mM D-glucose monohydrate, 20 mM HEPES Biological Buffer, 1.25 mM CaCl$_2$ and 0.5 mM MgCl$_2$ (pH 7.4). At the end of the preincubation, the media was removed and test compound solution (10 µM) in buffer was added to the apical compartment. The inserts were moved to wells containing fresh basolateral buffer at 1 hr. Drug concentration in the buffer was measured by LC/MS analysis.

Flux rate (F, mass/time) was calculated from the slope of cumulative appearance of substrate on the receiver side and apparent permeability coefficient ($P_{app}$) was calculated from the following equation.

$$P_{app}(\text{cm/sec}) = (F^*VD)/(SA^*MD)$$

where SA is surface area for transport (0.3 cm$^2$), VD is the donor volume (0.3 ml), MD is the total amount of drug on the donor side at t=0. All data represent the mean of 2 inserts. Monolayer integrity was determined by Lucifer Yellow transport.

Half-Life in Human Liver Microsomes (HLM)

Test compounds (1 µM) were incubated with 3.3 mM MgCl$_2$ and 0.78 mg/mL HLM (HL101) in 100 mM potassium phosphate buffer (pH 7.4) at 37° C. on the 96-deep well plate. The reaction mixture was split into two groups, a non-P450 and a P450 group. NADPH was only added to the reaction mixture of the P450 group. An aliquot of samples of P450 group was collected at 0, 10, 30, and 60 min time point, where 0 min time point indicated the time when NADPH was added into the reaction mixture of P450 group. An aliquot of samples of non-P450 group was collected at −10 and 65 min time point. Collected aliquots were extracted with acetonitrile solution containing an internal standard. The precipitated protein was spun down in centrifuge (2000 rpm, 15 min). The compound concentration in supernatant was measured by LC/MS/MS system.

The half-life value was obtained by plotting the natural logarithm of the peak area ratio of compounds/internal standard versus time. The slope of the line of best fit through the points yields the rate of metabolism (k). This was converted to a half-life value using following equations:

Half-life=ln2/k

EXAMPLES

The invention is illustrated in the following non-limiting examples in which, unless stated otherwise: all operations were carried out at room or ambient temperature, that is, in the range of 18-25° C.; evaporation of solvent was carried out using a rotary evaporator under reduced pressure with a bath temperature of up to 60° C.; reactions were monitored by thin layer chromatography (TLC) and reaction times are given for illustration only; melting points (mp) given are uncorrected (polymorphism may result in different melting points); the structure and purity of all isolated compounds were assured by at least one of the following techniques: TLC (Merck silica gel 60 $F_{254}$ precoated TLC plates or Merck $NH_2$ gel (an amine coated silica gel) $F_{254s}$ precoated TLC plates), mass spectrometry, nuclear magnetic resonance spectra (NMR), infrared absorption spectra (IR) or microanalysis. Yields are given for illustrative purposes only. Workup with a cation-exchange column was carried out using SCX cartridge (Varian Bond-Elute), which was preconditioned with methanol. Flash column chromatography was carried out using Merck silica gel 60 (63-200 μm), Wako silica gel 300HG (40-60 μm), Fuji Silysia NH gel (an amine coated silica gel) (30-50 μm), Biotage KP-SIL (32-63 μm) or Biotage AMINOSILICA (an amine coated silica gel) (40-75 μm). Preparative TLC was carried out using Merck silica gel 60 $F_{254}$ precoated TLC plates (0.5 or 1.0 mm thickness). Low-resolution mass spectral data (EI) were obtained on an Integrity (Waters) mass spectrometer. Low-resolution mass spectral data (ESI) were obtained on ZMD™ or ZQ™ (Waters) and mass spectrometer. NMR data were determined at 270 MHz (JEOL JNM-LA 270 spectrometer), 300 MHz (JEOL JNM-LA300 spectrometer) or 600 MHz (Bruker AVANCE 600 spectrometer) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, quint=quintet, m=multiplet, br.=broad, etc. IR spectra were measured by a Fourier transform infrared spectrophotometer (Shimazu FTIR-8300). The powder X-ray diffraction (PXRD) pattern was determined using a Rigaku RINT-TTR powder X-ray diffractometer fitted with an automatic sample changer, a 2 theta-theta goniometer, beam divergence slits, a secondary monochromator and a scintillation counter. The sample was prepared for analysis by packing the powder on to an aluminum sample holder. The specimen was rotated by 60.00 rpm and scanned by 4°/min at room temperature with Cu-ka radiation. Chemical symbols have their usual meanings; bp (boiling point), mp (melting point), L (liter(s)), mL (milliliter(s)), g (gram(s)), mg (milligram(s)), mol (moles), mmol (millimoles), eq. (equivalent(s)), quant. (quantitative yield).

Example 1

4-{[4-({[(2'-OXOSPIRO[CYCLOPENTANE-1,3'-INDOL]-1'(2'H)-YL)CARBONYL]AMINO}METHYL)PIPERIDIN-1-YL]METHYL}TETRAHYDRO-2H-PYRAN-4-CARBOXYLIC ACID

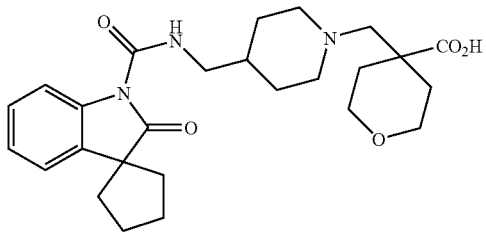

Step 1. tert-Butyl 4-cyanotetrahydro-2H-pyran-4-carboxylate

To a stirred suspension of NaH (17.7 g, 0.443 mol) in N,N-dimethylformamide (200 mL) was added dropwise a solution of tert-butyl cyanoacetate (25.0 g, 0.177 mol) in N,N-dimethylformamide (100 mL) at 0° C. under $N_2$. The mixture was allowed to warm up to ambient temperature, and stirred for 1 h. Then, bis(2-bromoethyl)ether (49.3 g, 0.177 mol) was added to the mixture, and the resulting mixture was stirred at 90° C. for 24 h. After cooling to 0° C., the mixture was washed with water (100 mL). The volatile components were removed by evaporation and the residue was precipitated with a mixture of ethyl acetate-toluene (1:2, 500 mL) and water (500 mL). The organic phase was washed with water (500 mL) three times, dried over $Na_2SO_4$, filtered and evaporated. The solid was washed with hexane, collected by filtration and dried in vacuo to give 19.0 g (57%) of the title compound as white crystal.

$^1$H-NMR (CDCl$_3$) δ: 3.96 (2H, dt, J=3.9 Hz, 12.3 Hz), 3.73 (2H, dt, J=2.6 Hz, 12.3 Hz), 2.20-1.94 (4H, m), 1.52 (9H, s).

Step 2. tert-Butyl 4-(aminomethyl)tetrahydro-2H-pyran-4-carboxylate

A mixture of tert-butyl 4-cyanotetrahydro-2H-pyran-4-carboxylate (18.95 g, 0.0897 mol, step 1 of Example 1) and Raney Ni (1.00 g) in methanol (200 mL) was hydrogenated (3 atm) at room temperature for 12 h. Then, the mixture was filtered through a pad of Celite, and the filtrate was concentrated in vacuo to give 16.01 g (83%) of the title compound as yellow syrup.

$^1$H-NMR (CDCl$_3$) δ: 3.86 (2H, dt, J=4.1 Hz, 11.4 Hz), 3.48 (2H, dt, J=2.5 Hz, 11.5 Hz), 2.75 (2H, s), 2.03 (2H, br d, J=10.7 Hz), 1.55-1.35 (13H, m, including 9H, s, 1.49 ppm).

Step 3. tert-Butyl 4-[(4-oxopiperidin-1-yl)methyl]tetrahydro-2H-Pyran-4-carboxylate To a refluxing mixture of tert-butyl 4-(aminomethyl)tetrahydro-2H-pyran-4-carboxylate (8.00 g, 0.0372 mol, step 2 of Example 1) and $K_2CO_3$ (0.51 g, 0.0372 mol) in ethanol-$H_2O$ (2:1, 240 mL) was added dropwise 1-ethyl-1-methyl-4-oxopiperidinium iodide (12.0 g, 0.0445 mol, J. Org. Chem. 1995, 60, 4324) in ethanol-$H_2O$ (2:1, 150 mL), and the resulting mixture was stirred at the same temperature for 1 h. After cooling to room temperature, the solvent was removed in vacuo. The residue was poured into sat. NaHCO$_3$ aq. (200 mL), and the mixture was extracted with $CH_2Cl_2$ (200 mL×3). The extracts were dried over $Na_2SO_4$, filtered and concentrated. The residue was chromatographed on a column of silica gel eluting with hexane/ethyl acetate (3:1 to 2:1) to give 10.77 g (98%) of the title compound as colorless syrup.

MS (ESI) m/z: 298 (M+H)$^+$.

$^1$H NMR (CDCl$_3$) δ 3.84 (2H, br d, J=11.4 Hz), 3.50 (2H, dt, J=2.0 Hz, 11.7 Hz), 2.85 (4H, t, J=5.9 Hz), 2.61 (2H, s), 2.39 (4H, t, J=6.1 Hz), 2.05 (2H, d, J=11.5 Hz), 1.75-1.45 (1H, m, including 9H, s, 1.49 ppm).

Step 4. tert-Butyl 4-[(4-cyanopiperidin-1-yl)methyl]tetrahydro-2H-pyran-4-carboxylate To a stirred solution of tert-butyl-4-[(4-oxopiperidin-1-yl)methyl]tetra hydro-2H-pyran-4-carboxylate (8.77 g, 0.0295 mol, step 3 of Example 3) in 1,2-dimethoxyethane (250 mL) was added p-toluenesulfonylmethylisocyanide (11.51 g, 0.0590 mol), ethanol (3.96 mL, 0.0678 mol) and potassium t-butoxide (11.58 g, 0.1032 mol) at 0° C. The resulting mixture was stirred at 50° C. for 16 h. After cooling, the reaction mixture was poured into sat. NaHCO$_3$ aq. (200 mL), and the mixture was extracted with CH$_2$Cl$_2$ (200 mL×3). The extracts were dried over Na$_2$SO$_4$, filtered and concentrated. The residue was chromatographed on a column of silica gel eluting with hexane/ethyl acetate (2:1) to give 5.76 g (63%) of the title compound as yellow syrup.

MS (ESI) m/z: 309 (M+H)$^+$.

$^1$H-NMR (CDCl$_3$) δ: 3.81 (2H, dt, J=3.1 Hz, 11.0 Hz), 3.48 (2H, dt, J=2.1 Hz, 11.7 Hz), 2.76-2.64 (2H, m), 2.64-2.52 (1H, m), 2.50-2.35 (4H, m, including 2H, s, 2.46 ppm), 1.98 (2H, br d, J=11.9 Hz), 1.92-1.70 (4H, m), 1.65-1.40 (1H, m, including 9H, s, 1.47 ppm).

Step 5. tert-Butyl-4-{[4-(aminomethyl)piperidin-1-yl]methyl}tetrahydro-2H-pyran-4-carboxylate A mixture of tert-butyl 4-[(4-cyanopiperidin-1-yl)methyl]tetra hydro-2H-pyran-4-carboxylate (5.76 g, 0.0187 mol, step 4 of Example 1) and Raney Ni (3.00 g) in methanol (100 mL) was hydrogenated (3 atm) at room temperature for 12 h. Then, the mixture was filtered through a pad of Celite, and the filtrate was concentrated in vacuo to give 5.72 g (98%) of the title compound as yellow syrup.

MS (ESI) m/z: 313 (M+H)$^+$.

$^1$H-NMR (CDCl$_3$) δ: 3.80 (2H, dt, J=3.1 Hz, 11.5 Hz), 3.49 (2H, dt, J=2.1 Hz, 12.2 Hz), 2.80 (2H, br d, J=11.5 Hz), 2.58-2.40 (4H, m, including 2H, s, 2.43 ppm), 2.15 (2H, br t, J=7.3 Hz), 1.98 (2H, br d, J=13.7 Hz), 1.70-1.40 (16H, m, including 9H, s, 1.47 ppm), 1.30-1.10 (2H, m).

Step 6. tert-Butyl 4-{[4-({[(2'-oxospiro[cyclopentane-1,3'-indol]-1'(2'H)-yl)carbonyl]amino}methyl)piperidin-1-yl]methyl}tetrahydro-2H-pyran-4-carboxylate To a stirred solution of spiro[cyclopentane-1,3'-indol]-2'(1'H)-one (600 mg, 3.2 mmol, Howard, Harry R. et al., J. Med. Chem., 1996, 39, 143) and triethylamine (972 mg, 9.6 mmol) in CH$_2$Cl$_2$ (20 mL) was added 4-nitrochloroformate (677 mg, 3.4 mmol) at room temperature, and stirred at ambient temperature for 3 h. Then, a solution of tert-butyl 4-{[4-(aminomethyl)piperidin-1-yl]methyl}tetrahydro-2H-pyran-4-carboxylate (1.0 g, 3.2 mmol, step 5 of Example 1) in CH$_2$Cl$_2$ (5 mL) was added at room temperature, and stirred for 18 h. Then, sat. NaHCO$_3$ aq. (20 mL) was added, extracted with CH$_2$Cl$_2$ (30 mL×3), dried over MgSO$_4$, filtered and concentrated gave yellow brown oil. The residue was chromatographed on a column of aminopropyl-silica gel eluting with hexane/ethyl acetate (11:1) to give 1.3 g (75%) of the title compound as clear yellow oil.

MS (ESI) m/z: 526 (M+H)$^+$.

$^1$H-NMR (CDCl$_3$) δ: 8.70 (1H, br s), 8.23 (1H, d, J=8.1 Hz), 7.41-7.10 (3H, m), 3.83-3.75 (2H, m), 3.52-3.47 (2H, m), 3.29-3.20 (2H, m), 2.83-2.75 (2H, m), 2.44 (2H, s), 2.25-1.20 (28H, m).

Step 7. 4-{[4-({[(2'-Oxospiro[cyclopentane-1,3'-indol]-1'(2'H)-yl)carbonyl]amino}methyl)piperidin-1-yl]methyl}tetrahydro-2H-pyran-4-carboxylic Acid To a solution of tert-butyl 4-{[4-({[(2'-oxospiro[cyclopentane-1,3'-indol]-1'(2'H)-yl)carbonyl]amino}methyl)piperidin-1-yl]methyl}tetrahydro-2H-pyran-4-carboxylate (2.3 g, 4.38 mmol, step 6 of Example 1) in CH$_2$Cl$_2$ (14 mL), trifluoroacetic acid (18 mL) was added at room temperature, and the mixture was stirred overnight at room temperature. The mixture was concentrated to give yellow oil, CH$_2$Cl$_2$ (200 mL) was added and washed with sat. NaHCO$_3$ aq. (80 mL), dried over MgSO$_4$, filtered and concentrated gave a syrup, which was chromatographed on a column of silica gel eluting with CH$_2$Cl$_2$/methanol (15:1) to give 2.1 g (quant.) of the title compound as white solid. Recrystallization from ethyl acetate/n-heptane gave white powder.

MS (ESI) m/z: 470 (M+H)$^+$.

m.p.: 146.3° C.

IR (KBr) ν: 2943, 2864, 1733, 1558, 1465, 1352, 1151, 1109, 759 cm$^{-1}$ $^1$H-NMR (CDCl$_3$) δ: 8.85 (1H, br s), 8.21 (1H, d, J=8.1 Hz), 7.30-7.15 (3H, m), 3.95-3.72 (4H, m), 3.40-3.25 (2H, m), 3.20-3.06 (2H, m), 2.65-2.45 (4H, m), 2.25-1.85 (13H, m), 1.60-1.40 (4H, m). Signal due to CO$_2$H was not observed.

Anal. Calcd. for C$_{26}$H$_{35}$N$_3$O$_5$.0.25H$_2$O: C, 65.87; H, 7.55; N, 8.86. Found: C, 65.58; H, 7.39; N, 8.86.

Example 2

2,2-DIMETHYL-3-[4-({[(2'-OXOSPIRO[CYCLOPENTANE-1,3'-INDOL]-1'(2'H)-YL)CARBONYL]AMINO}METHYL)PIPERIDIN-1-YL]PROPANOIC ACID

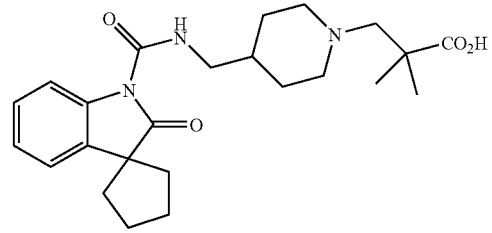

Step 1. tert-Butyl 4-({[(2'-oxospiro[cyclopentane-1,3'-indol]-1'(2'H)-yl)carbonyl]amino}methyl)piperidine-1-carboxylate The title compound was prepared according to the procedure described in step 6 of Example 1 from tert-butyl 4-(aminomethyl)piperidine-1-carboxylate.

Rf=0.2 (hexane/ethyl acetate (8/1))

$^1$H-NMR (CDCl$_3$) δ: 8.78 (1H, br s), 8.23 (1H, d, J=9 Hz), 7.31-7.10 (3H, m), 4.20-4.05 (2H, m), 3.35-3.25 (2H, m), 2.80-2.60 (2H, m), 2.25-1.80 (9H, m), 1.80-1.65 (2H, m), 1.46 (9H, s), 1.30-1.10 (2H, m).

Step 2. 2'-Oxo-N-(piperidin-4-ylmethyl)spiro[cyclopentane-1,3'-indole]-1'(2'H)-carboxamide tert-Butyl 4-({[(2'-oxospiro[cyclopentane-1,3'-indol]-1'(2'H)-yl)carbonyl]amino}methyl)piperidine-1-carboxylate (750 mg, 1.8 mmol, step 1 of Example 2) was dissolved in 10% HCl in methanol (20 mL) and the mixture was stirred for 7 h at room temperature. Concentrated gave a colorless oil, which was chromatographed on a column of silica gel eluting with CH₂Cl₂/methanol/NH₄OH (12/11/0.1) to give 570 mg (quant.) of the title compound as colorless oil.

MS (ESI) m/z: 328 (M+H)⁺.

¹H-NMR (CDCl₃) δ: 8.76 (1H, br s), 8.24 (1H, d, J=9.0 Hz), 7.31-7.10 (3H, m), 3.32-3.25 (2H, m), 3.15-3.09 (2H, m), 2.67-2.60 (2H, m), 2.30-1.60 (12H, m), 1.32-1.10 (2H, m).

Step 3. Methyl 2,2-dimethyl-3-[4-({[(2'-oxospiro [cyclopentane-1,3'-indol]-1'(2'H)-yl)carbonyl] amino}methyl)piperidin-1-yl]propanoate To a stirred solution of 2'-oxo-N-(piperidin-4-ylmethyl) spiro[cyclopentane-1,3'-indole]-1'(2'H)-carboxamide (480 mg, 1.5 mmol, step 2 of Example 2) and methyl 2,2-dimethyl-3-oxopropanoate (248 mg, 1.7 mmol, Kim, Hwa-Ok et al., *Synth. Commun.*, 1997, 27, 2505) in CH₂Cl₂ (40 mL) was added sodium triacetoxyborohydride (623 mg, 2.9 mmol) in one portion at room temperature. The mixture was stirred for 20 h at ambient temperature. To the mixture was added sat. NaHCO₃ aq. (10 mL), extracted with CH₂Cl₂ (30 mL×2), dried over MgSO₄, filtered and concentrated gave yellow oil. The residue was chromatographed on a column of aminopropyl-silica gel eluting with hexane/ethyl acetate (9:1) to give 150 mg (23%) of the title compound as clear colorless oil.

MS (ESI) m/z: 442 (M+H)⁺.

¹H-NMR (CDCl₃) δ: 8.72 (1H, br s), 8.24 (1H, d, J=8.1 Hz), 7.31-7.10 (3H, m), 3.65 (3H, s), 3.27-3.20 (2H, m), 2.85-2.75 (2H, m), 2.46 (2H, s), 2.23-1.90 (1H, m), 1.70-1.60 (2H, m), 1.35-1.28 (2H, m), 1.15 (6H, s).

Step 4. 2,2-Dimethyl-3-[4-({[(2'-oxospiro[cyclopentane-1,3'-indol]-1'(2'H)-yl)carbonyl]amino}methyl) piperidin-1-yl]propanoic Acid To a stirred solution of methyl 2,2-dimethyl-3-[4-({[(2'-oxospiro[cyclopentane-1,3'-indol]-1'(2'H)-yl)carbonyl] amino}methyl)piperidin-1-yl]propanoate (170 mg, 0.38 mmol, step 3 of Example 2) in acetic acid (2 mL), H₂SO₄ (113 mg) in water (2 mL) was added, and the mixture was refluxed for 36 h. The mixture was cooled to room temperature and solid NaHCO₃ (500 mg) was added slowly. The resulting mixture was concentrated to give white solid. To the solid, CH₂Cl₂ (40 mL) was added and stirred for 10 min, dried over MgSO₄. The solution was filtered and concentrated and then resulted yellow oil. The oil was chromatographed on a column of silica gel eluting with CH₂Cl₂/methanol (14:1) to give 130 mg (80%) of the title compound as white solid. Recrystallization from ethyl acetate/diethyl ether gave white powder.

MS (ESI) m/z: 427 (M+H)⁺.

m.p.: 189.1° C.

IR (KBr) ν: 2950, 1732, 1600, 1537, 1475, 1348, 1321, 1280, 1153, 964, 873, 758 cm⁻¹

¹H-NMR (CDCl₃) δ: 8.80 (1H, br s), 8.21 (1H, d, J=8.1 Hz), 7.35-7.10 (3H, m), 3.36-3.20 (2H, m), 3.20-3.10 (2H, m), 2.56 (2H, s), 2.54-2.40 (2H, m), 2.30-1.60 (1H, m), 1.58-1.35 (2H, m), 1.24 (6H, s). A signal due to CO₂H was not observed Anal. Calcd. for C₂₄H₃₃N₃O₄.0.3H₂O: C, 66.58; H, 7.82; N, 9.71. Found: C, 66.33; H, 7.72; N, 9.51.

Example 3

1-{[4-({[(2'-OXOSPIRO[CYCLOPENTANE-1,3'-INDOL]-1'(2'H)-YL)CARBONYL] AMINO}METHYL)PIPERIDIN-1-YL] METHYL}CYCLOPROPANECARBOXYLIC ACID

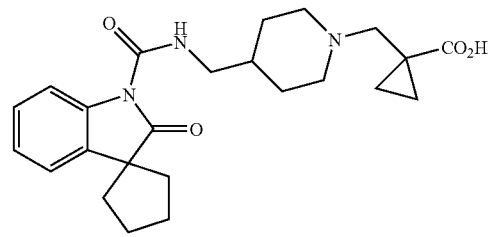

Step 1. tert-Butyl 1-(iodomethyl)cyclopropanecarboxylate

To a stirred solution of diisopropylamine (7.7 mL, 0.055 mol) in tetrahydrofuran (80 mL), n-butyl lithium (1.59 M in cyclohexane, 34 mL, 0.055 mol) was added slowly at −70° C. and the mixture was stirred for 20 min at 0° C. The mixture was cooled to −78° C. and tert-butyl cyclopropanecarboxylate (6.5 g, 0.046 mol, Kohlrausch et al., *Z. Elektrochem. Angew. Phys. Chem.*, 1937, 70, 392) in tetrahydrofuran (10 mL) was added dropwise, and the mixture was stirred for 3 h. Then, diiodomethane (4.0 mL, 0.050 mol) in tetrahydrofuran (10 mL) was added dropwise, and the mixture was allowed to warm up to room temperature overnight. Saturated aqueous NH₄Cl (80 mL) was added to the solution and it was extracted with diethyl ether (50 mL), washed with brine (20 mL), dried over MgSO₄, filtered and concentrated to give brown oil. The oil was chromatographed on a column of silica gel eluting with hexane/diethyl ether (40:1) to give 1.9 g of the title compound as a crude product. The crude product was used without further purification. Rf: 0.3 (hexane/diethyl ether (40:1))

Step 2. tert-Butyl 1-[(4-{[(tert-butoxycarbonyl) amino]methyl}piperidin-1-yl)methyl]cyclopropanecarboxylate A mixture of tert-butyl 1-(iodomethyl)cyclopropanecarboxylate (1.9 g 6.7 mmol, step 1 of Example 3), tert-butyl (piperidin-4-ylmethyl)carbamate (3.0 g, 14 mmol), N,N-diisopropylethylamine (5.8 mL, 34 mmol) in N,N-dimethylformamide (25 mL) was heated at 120° C. for 20 h. After cooled to room temperature, water (50 mL) was added, extracted with ethyl acetate/toluene (1:2, 60 mL×2), washed with water (50 mL×2), brine (50 mL), dried over MgSO₄, filtered and concentrated to give brown oil. The oil was chromatographed on a column of silica gel eluting with CH₂Cl₂/methanol (10:1) to give 560 mg (1%) of the title compound as clear brown oil. MS (ESI) m/z: 369 (M+H)⁺. ¹H-NMR (CDCl₃) δ: 4.60 (1H, br), 3.08-2.82 (4H, m), 2.59 (2H, s), 2.10-1.90 (2H, m), 1.75-1.55 (4H, m), 1.50-1.05 (23H, m).

Step 3. 1-{[4-(Aminomethyl)piperidin-1-yl] methyl}cyclopropanecarboxylic Acid tert-Butyl 1-[(4-{[(tert-butoxycarbonyl)amino] methyl}piperidin-1-yl)methyl]cyclopropanecarboxylate (211 mg, 0.57 mmol, step 2 of Example 3) was dissolved in 10% HCl in dioxane (5 mL) and the mixture was stirred for 4 h at room temperature. Resultant brown suspension was concentrated to give 150 mg (quant.) of the title compound as a pale brown solid. This was used without further purification.

MS (ESI) m/z: 211 (M−H)⁻.

Step 4. 1-{[4-({[(2'-Oxospiro[cyclopentane-1,3'-indol]-1'(2'H)-yl)carbonyl]amino}methyl)piperidin-1-yl]methyl}cyclopropanecarboxylic Acid The title compound was prepared according to the procedure described in step 6 of Example 1 from 1-{[4-(aminomethyl)piperidin-1-yl]methyl}cyclopropanecarboxylic acid (step 3 of Example 3). Purification was performed by silica gel column eluting with $CH_2Cl_2$/methanol (18:1~10:1) to give 130 mg (53%) of the title compound as white solid. The solid was triturated with hexane/diethyl ether, and collected by filtration to give the title compound as white solid.

MS (ESI) m/z: 426 (M+H)⁺. m.p.: 186.5° C.

IR (KBr) v: 3300, 2960, 2908, 1743, 1697, 1542, 1463, 1348, 1267, 1161, 1143, 1105, 779 cm⁻¹

¹H-NMR (CDCl₃) δ: 8.81 (1H, br s), 8.21 (1H, d, J=8.1 Hz), 7.32-7.14 (3H, m), 3.43-3.15 (4H, m), 2.59 (2H, s), 2.30-1.60 (17H, m), 0.65-0.56 (2H, m). A signal due to $CO_2\underline{H}$ was not observed.

Anal. Calcd. for $C_{24}H_{31}N_3O_4$: C, 67.74; H, 7.34; N, 9.88. Found: C, 67.45; H, 7.36; N, 9.80.

Example 4

1-{[4-({[(2'-OXOSPIRO[CYCLOPENTANE-1,3'-INDOL]-1'(2'H)-YL)CARBONYL]AMINO}METHYL)PIPERIDIN-1-YL]METHYL}CYCLOPENTANECARBOXYLIC ACID

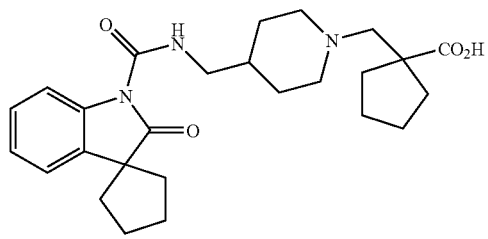

Step 1. Methyl 1-(iodomethyl)cyclopentanecarboxylate

The title compound was prepared according to the procedure described in step 1 of Example 3 from methyl cyclopentanecarboxylate.

¹H-NMR (CDCl₃) δ 3.73 (3H, s), 3.42 (2H, s), 2.30-2.15 (2H, m), 1.80-1.55 (6H, m).

Step 2. Methyl 1-[(4-{[(tert-butoxycarbonyl)amino]methyl}piperidine-1-yl)methyl]cyclopentanecarboxylate The title compound was prepared according to the procedure described in step 2 of Example 3 from methyl 1-(iodomethyl)cyclopentanecarboxylate.

MS (ESI) m/z: 355 (M+H)⁺.

¹H-NMR (CDCl₃) δ 4.58 (1H, br s), 3.66 (3H, s), 2.97 (2H, t, J=6.3 Hz), 2.77 (2H, br d, J=11.5 Hz), 2.55 (2H, s), 1.70-1.50 (9H, m), 1.44 (9H, s), 1.25-1.08 (2H, m).

Step 3. Methyl 1-{[4-(aminomethyl)piperidin-1-yl]methyl}cyclolentanecarboxylate A solution of methyl 1-[(4-{[(tert-butoxycarbonyl)amino]methyl}piperidine-1-yl)methyl]cyclopentanecarboxylate (1.16 g, 3.27 mmol, step 2 of Example 4) in $CH_2Cl_2$ (25 mL) and trifluoroacetic acid (5 mL) was stirred at room temperature for 1.5 h. The reaction mixture was then concentrated, basified with sat. $NaHCO_3$ aq. (100 mL) and extracted with $CHCl_3$ (100 mL) five times. The combined extracts were dried over $MgSO_4$, filtered and concentrated to give 0.831 g (100%) of title compound as yellow syrup.

MS (ESI) m/z: 255 (M+H)⁺.

¹H-NMR (CDCl₃) δ 3.66 (3H, s), 2.78 (2H, d, J=11.5 Hz), 2.62-2.50 (4H, m), (9H, m), 1.30-1.05 (2H, m).

Step 4. Methyl 1-{[4-({[(2'-oxospiro[cyclopentane-1,3'-indol]-1'(2'H)-yl)carbonyl]amino}methyl)piperidin-1-yl]methyl}cyclopentanecarboxylate The title compound was prepared according to the procedure described in step 6 of Example 1 from methyl 1-{[4-(aminomethyl)piperidin-1-yl]methyl}cyclopentane carboxylate (step 3 of Example 4).

MS (ESI) m/z: 468 (M+H)⁺.

¹H-NMR (CDCl₃) δ: 8.71 (1H, br s), 8.23 (1H, d, J=8.1 Hz), 7.34-7.10 (3H, m), 3.28-3.20 (2 H, m), 2.82-2.75 (2H, m), 2.56 (2H, s), 2.25-1.40 (21H, m), 1.38-1.12 (2H, m).

Step 5. 1-{[4-({[(2'-Oxospiro[cyclopentane-1,3'-indol]-1'(2'H)-yl)carbonyl]amino}methyl)piperidin-1-yl]methyl}cyclopentanecarboxylic Acid The title compound was prepared according to the procedure described in step 4 of Example 2 from methyl 1-{[4-({[(2'-oxospiro[cyclopentane-1,3'-indol]-1'(2'H)-yl) carbonyl]amino}methyl)piperidin-1-yl]methyl}cyclopentanecarboxylate (step 4 of Example 4).

MS (ESI) m/z: 454 (M+H)⁺.

m.p.: 188.1° C.

IR (KBr) v: 3301, 2935, 2869, 1730, 1602, 1531, 1469, 1278, 1147, 758 cm⁻¹

¹H-NMR (CDCl₃) δ: 8.80 (1H, br s), 8.21 (1H, d, J=8.1 Hz), 7.32-7.14 (3H, m), 3.31 (2H, t, J=5.4 Hz), 3.23-3.12 (2H, m), 2.67 (2H, s), 2.50-2.32 (2H, m), 2.31-1.56 (17H, m), 1.55-1.32 (4H, m). A signal due to $CO_2\underline{H}$ was not observed.

Anal. Calcd. for $C_{26}H_{35}N_3O_4 \cdot 0.5H_2O$: C, 67.51; H, 7.84; N, 9.08. Found: C, 67.17; H, 7.83; N, 8.85.

Example 5

1-{[4-({[(2'-OXOSPIRO[CYCLOPENTANE-1,3'-INDOL]-1'(2'H)-YL)CARBONYL]AMINO}METHYL)PIPERIDIN-1-YL]METHYL}CYCLOBUTANECARBOXYLIC ACID

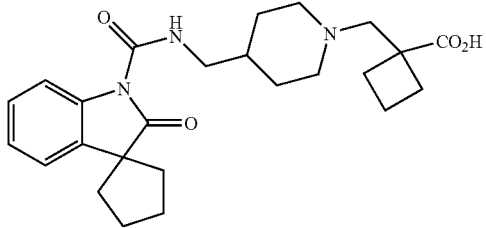

Step 1. Methyl 1-[(4-{[(tert-butoxycarbonyl)amino]methyl}piperidin-1-yl)methyl]cyclobutanecarboxylate To a stirred mixture of tert-butyl(piperidin-4-ylmethyl)carbamate (12.8 g, 60 mmol) and methyl 1-formylcyclobutanecarboxylate (2.13 g, 15 mmol, Davis, Charles R.; Swenson, Dale C.; Burton, Donald J., *J. Org. Chem.*, 1993, 58, 6843) in tetrahydrofuran (50 mL) was added acetic acid (8.6 mL, 150 mmol) at ambient temperature. After 30 min, sodium triacetoxyborohydride (12.7 g, 60 mmol) was added to the mixture. Then, the mixture was heated to 60° C. for 2 h. After cooling, the reaction mixture was poured into sat. NaHCO$_3$ aq. The aqueous layer was extracted with CH$_2$Cl$_2$ for 3 times. The combined organic phase were washed with brine, dried over MgSO$_4$, filtered and concentrated. The residue was chromatographed on a column of silica gel eluting with hexane/ethyl acetate (1:1) to give 4.25 g (83%) of the title compound as white solid.

MS (ESI) m/z: 341 (M+H)$^+$.

$^1$H-NMR (CDCl$_3$) δ: 3.69 (3H, s), 2.96 (2H, t, J=6.2 Hz), 2.75 (2H, d, J=11.4 Hz), 2.67 (2H, s), 2.37-2.46 (2H, m), 1.78-2.05 (6H, m), 1.45-1.65 (2H, m), 1.43 (9H, s), 1.09-1.21 (2H, m),

Step 2. Methyl 1-{[4-(aminomethyl)piperidin-1-yl]methyl}cyclobutanecarboxylate The title compound was prepared according to the procedure described in step 3 of Example 4 from methyl 1-[(4-{[(tert-butoxycarbonyl)amino]methyl}piperidin-1-yl)methyl]cyclobutanecarboxylate (step 1 of Example 5).

MS (ESI) m/z: 241 (M+H)$^+$.

$^1$H-NMR (CDCl$_3$) δ: 3.67 (3H, s), 2.72-2.78 (2H, m), 2.66 (2H, s), 2.54 (2H, d, J=6.2 Hz), 2.34-2.47 (2H, m), 1.79-2.04 (8H, m), 1.54-1.64 (2H, m), 1.05-1.35 (3H, m).

Step 3. Methyl 1-{[4-({[(2'-oxospiro[cyclopentane-1,3'-indol]-1'(2'H)-yl)carbonyl]amino}methyl)piperidin-1-yl]methyl}cyclobutanecarboxylate The title compound was prepared according to the procedure described in step 6 of Example 1 from methyl 1-{[4-(aminomethyl)piperidin-1-yl]methyl}cyclobutane carboxylate (step 2 of Example 5).

MS (ESI) m/z: 454 (M+H)$^+$.

$^1$H-NMR (CDCl$_3$) δ: 8.71 (1H, br s), 8.23 (1H, d, J=8.1 Hz), 7.35-7.10 (3H, m), 3.70 (3H, s), 3.27-3.21 (2H, m), 2.88-2.70 (2H, m), 2.68 (2H, s), 2.49-2.35 (2H, m), 2.28-2.15 (2H, m), 2.14-1.75 (13H, m), 1.70-1.62 (2H, m), 1.34-1.15 (2H, m).

Step 4. 1-{[4-({[(2'-Oxospiro[cyclopentane-1,3'-indol]-1'(2'H)-yl)carbonyl]amino}methyl)piperidin-1-yl]methyl}cyclobutanecarboxylic Acid The title compound was prepared according to the procedure described in step 4 of Example 2 from methyl 1-{[4-({[(2'-oxospiro[cyclopentane-1,3'-indol]-1'(2'H)-yl)carbonyl]amino}methyl)piperidin-1-yl]methyl}cyclobutanecarboxylate (step 3 of Example 5).

MS (ESI) m/z: 440 (M+H)$^+$.

m.p.: 171.0° C.

IR (KBr) v: 3303, 2937, 2868, 1728, 1537, 1461, 1280, 1226, 1145, 765, 750 cm$^{-1}$ $^1$H-NMR (CDCl$_3$) δ: 8.80 (1H, br s), 8.20 (1H, d, J=8.0 Hz), 7.32-7.12 (3H, m), 3.30 (2H, t, J=6.1 Hz), 3.14-3.00 (2H, m), 2.77 (2H, s), 2.60-2.46 (2H, m), 2.45-1.70 (17H, m), 1.54-1.35 (2H, m). A signal due to CO$_2$H was not observed.

Anal. Calcd. for C$_{25}$H$_{33}$N$_3$O$_4$·0.5H$_2$O: C, 66.94; H, 7.64; N, 9.37. Found: C, 66.95; H, 7.75; N, 9.32.

Example 6

2-ETHYL-2-{[4-({[(2'-OXOSPIRO[CYCLOPENTANE-1,3'-INDOL]-1'(2'H)-YL)CARBONYL]AMINO}METHYL)PIPERIDIN-1-YL]METHYL}BUTANOIC ACID

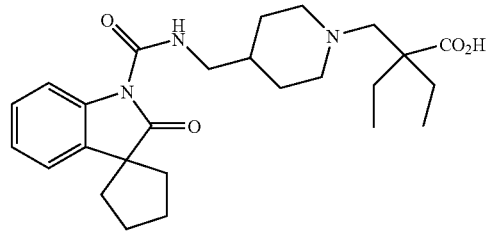

Step 1. Methyl 2-[(4-{[(tert-butoxycarbonyl)amino]methyl}piperidin-1-yl)methyl]-2-ethylbutanoate The title compound was prepared with the similar method shown in the step 1 of Example 5 by using methyl 2-ethyl-2-formylbutanoate (Okano, K.; Morimoto, T.; Sekiya, M. *Journal of the Chemical Society, Chemical Communications*, 1985, 3, 119)

MS (ESI) m/z: 357 (M+H)$^+$.

$^1$H-NMR (CDCl$_3$) δ: 4.62-4.48 (1H, br), 3.65 (3H, s), 3.01-2.93 (2H, m), 2.73-2.65 (2H, m), 2.46 (2H, s), 2.13-2.02 (2H, m), 1.73-1.50 (6H, m), 1.44 (9H, s), 1.28-1.10 (3H, m), 0.76 (6H, t, J=7.5 Hz).

Step 2. Methyl 2-{[4-(aminomethyl)piperidin-1-yl]methyl}-2-ethylbutanoate

The title compound was prepared according to the procedure described in step 3 of Example 4 from methyl 2-[(4-{[(tert-butoxycarbonyl)amino]methyl}piperidin-1-yl)methyl]-2-ethylbutanoate (step 1 of Example 6).

MS (ESI) m/z: 459 (M+H)+.
$^1$H-NMR (CDCl$_3$) δ: 8.92-8.86 (1H, m), 8.28-8.23 (1H, m), 7.20-7.12 (3H, m), 4.77-4.61 (1H, m), 3.65 (3H, s), 3.27 (2H, t, J=6.4 Hz), 2.75-2.66 (2H, m), 2.47 (2H, s), 2.16-2.05 (2H, m), 1.72-1.49 (10H, m), 1.38-1.21 (5H, m), 0.76 (6H, d, J=7.5 Hz).

Step 3. Methyl 2-ethyl-2-{[4-({[(2'-oxospiro[cyclopentane-1,3'-indol]-1'(2'H)-yl)carbonyl]amino}methyl)piperidin-1-yl]methyl}butanoate The title compound was prepared according to the procedure described in step 6 of Example 1 from methyl 2-{[4-(aminomethyl)piperidin-1-yl]methyl}-2-ethyl butanoate (step 2 of Example 6).
MS (ESI) m/z: 470 (M+H)+.
$^1$H-NMR (CDCl$_3$) δ: 8.72 (1H, br s), 8.23 (1H, d, J=8.1 Hz), 7.30-7.13 (3H, m), 3.65 (3H, s), 3.24 (2H, t, J=5.4 Hz), 2.75-2.69 (2H, m), 2.47 (2H, m), 2.30-1.50 (20H, m), 1.35-1.20 (2H, m), 0.76 (3H, t, J=6.0 Hz).

Step 4. 2-Ethyl-2-{[4-({[(2'-oxospiro[cyclopentane-1,3'-indol]-1' (2'H)-yl)carbonyl]amino}methyl)piperidin-1-yl]methyl}butanoic Acid The title compound was prepared according to the procedure described in step 4 of Example 2 from methyl 2-ethyl-2-{[4-({[(2'-oxospiro[cyclopentane-1,3'-indol]-1'(2'H)-yl)carbonyl]amino}methyl) piperidin-1-yl]methyl}butanoate (step 3 of Example 6).
MS (ESI) m/z: 456 (M+H)+.
IR (KBr) ν: 3323, 2937, 1732, 1596, 1539, 1463, 1348, 1147, 746 cm$^{-1}$
$^1$H-NMR (CDCl$_3$) d: 8.80 (1H, br s), 8.22 (1H, d, J=8.1 Hz), 7.35-7.15 (3H, m), 3.31 (2H, t, J=6.0 Hz), 3.18-3.05 (2H, m), 2.61 (2H, s), 2.57-2.40 (2H, m), 2.30-1.25 (17H, m), 0.88 (6H, t, J=9.0 Hz). Signal due to CO$_2$H was not observed.
Anal. Calcd. for C$_{26}$H$_{37}$N$_3$O$_4$·0.4H$_2$O: C, 67.48; H, 8.23; N, 9.08. Found: C, 67.87; H, 8.13; N, 8.95.

Example 7

1-{[4-({[(6'-FLUORO-2'-OXOSPIRO[CYCLOPENTANE-1,3'-INDOL]-1'(2'H)-YL)CARBONYL]AMINO}METHYL)PIPERIDIN-1-YL]METHYL}CYCLOBUTANECARBOXYLIC ACID

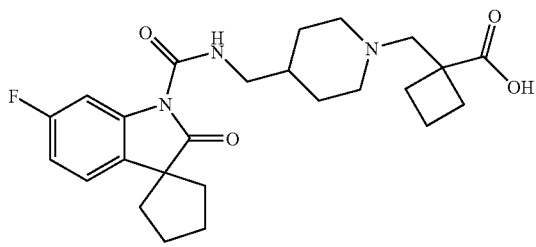

Step 1. Ethyl 1-[(4-{[(tert-butoxycarbonyl)amino]methyl}piperidin-1-yl)methyl]cyclobutanecarboxylate The title compound was prepared according to the procedure described in step 3 of Example 8 from [cyclobutylidene(ethoxy)methoxy](trimethyl)silane (Kuo. Y.-N. et al., *J. Chem. Soc. D.,* 1971, 136).

MS (ESI) m/z: 355 (M+H)+.
$^1$H-NMR (CDCl$_3$) δ: 4.55 (1H, br), 4.17 (2H, q, J=7.1 Hz), 2.96 (2H, t, J=6.3 Hz), 2.76 (2H, d, J=11.4 Hz), 2.48-2.33 (2H, m), 2.05-1.80 (6H, m), 1.43 (9H, s), 1.25 (3H, q, J=7.1 Hz), 1.40-1.05 (7H, m).

Step 2. 1-[(4-{[(tert-Butoxycarbonyl)amino]methyl}piperidin-1-yl)methyl]cyclobutanecarboxylic Acid A mixture of ethyl 1-[(4-{[(tert-butoxycarbonyl)amino]methyl}piperidin-1-yl)methyl]cyclobutanecarboxylate (4.2 g, 11.9 mmol, step 1 of Example 7), 2N NaOH (18 mL) and ethanol (12 mL) was heated at 50° C. for 4 h. The resulting solution was cooled in ice bath and 2N HCl (ca 19 mL) was added until pH of the mixture was ca 5-6. The whole was extracted with CH$_2$Cl$_2$/i-propanol (3:1, 30 mL×3). Combined organic layers were dried (Na$_2$SO$_4$) and filtered. The filtrate was concentrated to give 3.8 g (98%) of the titled compound as yellow solid.
$^1$H NMR (CDCl$_3$) δ: 4.08 (1H, m), 3.20-3.10 (2H, m), 3.08-2.99 (2H, m), 2.91 (2H, s), 2.60-2.38 (4H, m), 2.35-2.16 (2H, m), 2.05-1.76 (6H, m), 1.65 (1H, m), 1.44 (9H, s)

Step 3. 1-{[4-(Aminomethyl)piperidin-1-yl]methyl}cyclobutanecarboxylic acid 4-methylbenzenesulfonate In a 500 mL, 3-necked round bottom flask under N$_2$, a mixture of 1-[(4-{[(tert-butoxycarbonyl)amino]methyl}piperidin-1-yl)methyl]cyclobutane carboxylic acid (30 g, 92 mmol, step 2 of Example 7) in tetrahydrofuran (150 mL) was stirred at room temperature for 10 min. To this suspension, a solution of p-toluensulfonic acid monohydrate (52.4 g, 276 mmol) in tetrahydrofuran (150 mL) was added at room temperature. After stirring at that temp for 10 min, the resulting solution was heated under reflux condition for 3 h. After cooling down to room temperature, triethylamine (28.1 mL, 202 mmol) was added very slowly during the period of 1 h with seeding. The white precipitate was formed during the addition of triethylamine. The resulting white suspension was stirred at room temperature for 6 h and it was filtered and the obtained solid was washed with tetrahydrofuran (100 mL×2), dried at 50° C. for 5 h to give 35 g (96%) of the titled compound as white powder.
m.p.: 210° C.
$^1$H-NMR (D$_2$O) δ: 7.40 (2H, d, J=7.2 Hz), 7.07 (2H, d, J=7.2 Hz), 3.28-3.00 (4H, m), 2.80-2.57 (4H, m), 2.09 (3H, s), 2.18-1.97 (2H, m), 1.85-1.58 (8H, m), 1.36-1.12 (2H, m)

Step 4. 1-{[4-({[(6'-Fluoro-2'-oxospiro[cyclopentane-1,3'-indol]-1'(2'H)-yl)carbonyl]amino}methyl) piperidin-1-yl]methyl}cyclobutanecarboxylic Acid The title compound was prepared according to the procedure described in step 6 of Example 1 from 6'-fluorospiro[cyclopentane-1,3'-indol]-2'(1'H)-one (Joensson, N et al., *Acta Chem. Scand. Ser. B,* 1974, 28, 225) and 1-{[4-(aminomethyl)piperidine-1-yl]methyl}cyclobutanecarboxylic acid 4-methylbenzene sulfonate (step 3 of Example 7).
MS (ESI) m/z: 458 (M+H)+.
m.p.: 150.3° C.
IR (KBr) ν: 3305, 2935, 1735, 1602, 1492, 1440, 1357, 1296, 1228, 1157, 1095, 869 cm$^{-1}$
$^1$H-NMR (CDCl$_3$) δ: 8.73 (1H, br s), 8.01 (1H, dd, J=5.4, 8.1 Hz), 6.92-6.83 (1H, m), 3.30 (2H, t, J=5.4 Hz), 3.15-3.03

(2H, m), 2.78 (3H, s), 2.64-2.50 (2H, m), 2.45-1.70 (16H, m), 1.55-1.36 (2H, m). A signal due to CO$_2$H was not observed.
Anal. Calcd. for C$_{25}$H$_{32}$FN$_3$O$_4$.0.4H$_2$O: C, 64.61; H, 7.11; N, 9.01. Found: C, 64.31; H, 7.11; N, 9.05.

Example 8

4-{[4-({[(6'-FLUORO-2'-OXOSPIRO[CYCLOPEN-TANE-1,3'-INDOL]-1'(2'H)-YL)CARBONYL]AMINO}METHYL)PIPERIDIN-1-YL]METHYL}TETRAHYDRO-2H-PYRAN-4-CARBOXYLIC ACID

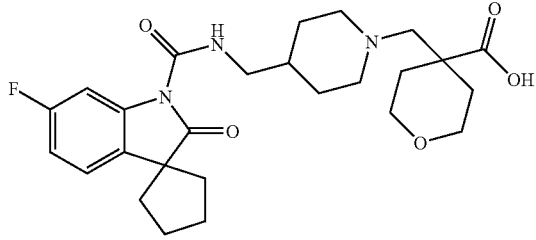

Step 1. tert-Butyl {[1-(ethoxymethyl)piperidin-4-yl]methyl}carbamate

To a stirred solution of tert-butyl(piperidin-4-ylmethyl)carbamate (7.0 g, 33 mmol) in ethanol (19 mL), paraformaldehyde (1.2 g, 39 mmol) and K$_2$CO$_3$ (5.4 g, 39 mmol) were added at ambient temperature. The mixture was stirred at ambident temperature for 4 h. The mixture was filtered and the filter cake was washed with ethanol (50 mL). The volatile components were removed by evaporation to give 8.9 g (quant.) of the title compound as a white powder.
$^1$H-NMR (CDCl$_3$) δ: 4.60 (1H, br s), 4.07 (2H, s), 3.49 (2H, q, J=7.1 Hz), 3.08-2.83 (4H, m), 2.50-2.36 (2H, m), 1.75-1.60 (2H, m), 1.44 (9H, s), 1.52-1.35 (1H, m), 1.19 (3H, t, J=7.1 Hz), 1.31-1.12 (2H, m).

Step 2. [Methoxy(tetrahydro-4H-pyran-4-ylidene)methoxy](trimethyl)silane

To a stirred solution of diisopropylamine (1.6 g, 0.016 mol) in tetrahydrofuran (4 mL) was added dropwise n-butyllithium (1.59 M in hexane, 9.2 mL, 0.014 mol) at 0° C. under nitrogen, and stirred for 20 min. Then, the reaction mixture was cooled to −40° C., methyl tetrahydro-2H-pyran-4-carboxylate (1.9 g, 0.013 mol) and trimethylsilyl chloride (2.0 mL, 0.015 mol) in tetrahydrofuran (1 mL) was added, and the resulting mixture was gradually warmed to room temperature over 3 h. The volatile components were removed by evaporation and the residue was filtered through a pad of Celite washing with hexane. The filtrate was dried in vacuo to give 2.9 g (quant.) of the title compound as a clear yellow oil.
$^1$H-NMR (CDCl$_3$) δ: 3.64-3.59 (4H, m), 3.52 (3H, s), 2.24 (2H, t, J=5.2 Hz), 2.15 (2H, t, J=5.3 Hz), 0.22 (9H, s).

Step 3. Methyl 4-[(4-{[(tert-butoxycarbonyl)amino]methyl}piperidin-1-yl)methyl]tetrahydro-2H-pyran-4-carboxylate To a stirred solution of tert-butyl {[1-(ethoxymethyl)piperidin-4-yl]methyl}carbamate (4 g, 14 mmol, step 1 of Example 8) and [methoxy(tetrahydro-4H-pyran-4-ylidene)methoxy](trimethyl)silane (2.9 g, 13 mmol, step 2 of Example 8) in CH$_2$Cl$_2$ (30 mL) was added dropwise trimethylsilyl trifluoromethanesulfonate (0.24 mL, 1.3 mmol) at 0° C., and the resulting mixture was stirred at room temperature for 12 h. The reaction mixture was quenched with saturated aqueous sodium bicarbonate (150 mL), extracted with CH$_2$Cl$_2$ (30 mL×2), and the combined organic layer was dried over sodium sulfate and filtered. Removal of the solvent gave a residue, which was chromatographed on a column of silica gel eluting with ethyl acetate/hexane (1:1) to give 6.3 g (64%) of the title compound as clear colorless oil.
MS (ESI) m/z: 371 (M+H)$^+$.
$^1$H-NMR (CDCl$_3$) δ: 4.57 (1H, br s), 3.84-3.78 (2H, m), 3.70 (3H, s), 3.49-3.41 (2H, m), 2.99-2.95 (2H, m), 2.73-2.68 (2H, m), 2.47 (2H, s), 2.19-2.11 (2H, m), 2.06-2.01 (2H, m), 1.61-1.51 (5H, m), 1.44 (9H, s), 1.24-1.11 (2H, m).

Step 4. 4-[(4-{[(tert-butoxycarbonyl)amino]methyl}piperidin-1-yl)methyl]tetrahydro-2H-pyran-4-carboxylic Acid To a solution of methyl 4-[(4-{[(tert-butoxycarbonyl)amino]methyl}piperidine-1-yl)methyl]tetrahydro-2H-pyran-4-carboxylate (6.47 g, 17.5 mmol, step 3 of Example 8) in methanol (32 mL), 5 N NaOH aq (10 mL) was added at room temperature (exothermic). The resulting solution was stirred at 60° C. for 7 h, then cooled to 5~10° C. in ice-cold bath. To this solution, 5 N HCl aq (10 added and the resulting solution (pH value was ca. 6) was concentrated. To the residue, 2-propanol (80 mL) was added. This solution was concentrated. To the residue, 2-propanol (80 mL) was added and it was concentrated again. The residue was diluted with ethanol (80 mL) and the mixture was stirred at room temperature for 2 h. It was filtered through a Celite pad (5.0 g) to remove NaCl. The Celite pad was washed with ethanol (20 mL) and the combined filtrate was concentrated. To the residue, CH$_3$CN (40 mL) was added and it was concentrated. During this procedure, the formation of white precipitate was noticed. To the residue, CH$_3$CN (40 mL) was added and the resulting suspension was stirred at room temperature for 2 h. This mixture was filtered and obtained solid was washed with CH$_3$CN (10 mL), then dried under reduced pressure to give 4.1 g (65%) of the titled compound as white powder.
m.p.: 129° C.
$^1$H NMR (CDCl$_3$) δ: 4.66 (1H, m), 3.93-3.82 (3H, m), 3.15-2.99 (4H, m), 2.58 (2H, s), 2.58-2.45 (2H, m), 1.98-1.76 (4H, m), 1.55-1.35 (6H, m), 1.44 (9H, s).

Step 5. 4-{[4-(aminomethyl)piperidin-1-yl]methyl}tetrahydro-2H-pyran-4-carboxylic acid 4-methylbenzenesulfonate In a 300 mL, 3-necked round bottom flask under N$_2$, 4-[(4-{[(tert-butoxycarbonyl)amino]methyl}piperidin-1-yl)methyl]tetrahydro-2H-pyran-4-carboxylic acid (10 g, 28 mmol, step 4 of Example 8) was placed and a solution of p-toluenesulfonic acid monohydrate (16 g, 84 mmol) in i-propanol (150 mL) was poured at room temperature. The resulting mixture was stirred at 60° C. for 7 h under N$_2$ and triethylamine (8.6 mL, 62 mmol) was added dropwise slowly during the period of 2 hr with seeding. The white precipitate was formed during the addition of triethylamine. The resulting white suspension was stirred at 60° C. for 3 h, at 50° C. for 5 h and at room temperature for 10 h. The suspension was filtered and the obtained solid was washed with i-propanol (100 mL), dried at 50° C. for 5 h to give 10.5 g (87%) of the titled compound as white powder.

m.p.: 247° C.

$^1$H-NMR (D$_2$O) δ: 7.54 (2H, d, J=7.4 Hz), 7.22 (2H, J=7.4 Hz), 3.80-3.65 (2H, m), 3.55-3.40 (4H, m), 3.20-2.75 (6H, m), 2.24 (3H, s), 1.90-1.80 (6H, m), 1.55-1.35 (4H, m)

Step 6. 4-{[4-({[(6'-Fluoro-2'-oxospiro[cyclopentane-1,3'-indol]-1'(2'H)-yl)carbonyl]amino}methyl) piperidin-1-yl]methyl}tetrahydro-2H-pyran-4-carboxylic Acid The title compound was prepared according to the procedure described in step 6 of Example 1 from 6'-fluorospiro [cyclopentane-1,3'-indol]-2'(1'H)-one (Joensson, N et al., *Acta Chem. Scand. Ser. B*, 1974, 28, 225) and 4-{[4-(aminomethyl)piperidine-1-yl]methyl}tetrahydro-2H-pyran-4-carboxylic acid 4-methyl benzenesulfonate (step 5 of Example 8).

MS (ESI) m/z: 488 (M+H)$^+$.

m.p.: 161.3° C.

IR (KBr) ν: 3315, 2943, 2869, 1733, 1604, 1541, 1473, 1359, 1298, 1228, 1157, 1099, 867 cm$^{-1}$ $^1$H-NMR (CDCl$_3$) δ: 7.16-7.11 (1H, m), 6.90-6.84 (1H, m), 3.90-3.75 (4H, m), 3.31 (2H, t, J=6.0 Hz), 3.18-3.06 (2H, m), 2.65-2.45 (4H, m), 2.25-1.75 (13H, m), 1.58-1.40 (4H, m). Signal due to CO$_2$H was not observed.

Anal. Calcd. for C$_{26}$H$_{34}$FN$_3$O$_5$.0.4H$_2$O: C, 63.12; H, 7.09; N, 8.49. Found: C, 62.83; H, 7.09; N, 8.45.

Example 9

1-{[4-({[(3,3-DIMETHYL-2-OXO-2,3-DIHYDRO-1H-INDOL-1-YL)CARBONYL]AMINO}METHYL)PIPERIDIN-1-YL] METHYL}CYCLOBUTANECARBOXYLIC ACID

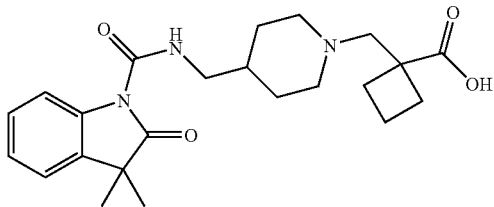

The title compound was prepared according to the procedure described in step 6 of Example 1 from 3,3-dimethyl-1, 3-dihydro-2H-indol-2-one (Robertson, David W et al., *J. Med. Chem.*, 1986, 29, 1832) and 1-{[4-(aminomethyl)piperidin-1-yl]methyl}cyclobutanecarboxylic acid 4-methylbenzenesulfonate (step 3 of Example 7).

MS (ESI) m/z: 414 (M+H)$^+$.

m.p.: 170.9° C.

IR (KBr) ν: 3440, 3296, 2933, 1735, 1705, 1608, 1541, 1382, 1346, 1271, 1159, 966, 773 cm$^{-1}$ $^1$H-NMR (CDCl$_3$) δ: 8.78 (1H, br s), 8.23 (1H, d, J=8.1 Hz), 7.35-7.18 (2H, m), 3.31 (2H, t, J=5.4 Hz), 3.12-3.01 (2H, m), 2.78 (2H, s), 2.61-2.48 (2H, m), 2.45-2.25 (3H, m), 2.00-1.75 (6H, m), 1.44 (3H, s), 1.55-1.40 (6H, m). A signal due to CO$_2$H was not observed.

Anal. Calcd. for C$_{23}$H$_{31}$N$_3$O$_4$.0.4H$_2$O: C, 65.66; H, 7.62; N, 9.99. Found: C, 65.82; H, 7.64; N, 9.89.

Example 10

3-[4-({[(3,3-DIMETHYL-2-OXO-2,3-DIHYDRO-1H-INDOL-1-YL)CARBONYL] AMINO}METHYL)PIPERIDIN-1-YL]PROPANOIC ACID

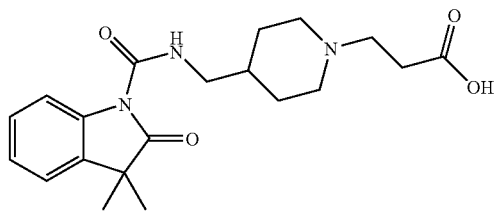

Step 1. Ethyl 3-(4-{[(tert-butoxycarbonyl)amino] methyl}piperidin-1-yl)propanoate A mixture of tert-butyl(piperidin-4-ylmethyl)carbamate (3.0 g, 14 mmol) and ethyl acrylate (1.7 g, 17 mmol) in ethanol (30 mL) was refluxed for 1 h. After cooled to room temperature, the solution was concentrated to give clear colorless oil. The residue was chromatographed on a silica gel column eluting with CH$_2$Cl$_2$/methanol (14:1) to give 4.0 g (91%) of the title compound as clear colorless oil.

MS (ESI) m/z: 315 (M+H)$^+$.

$^1$H-NMR (CDCl$_3$) δ: 4.61 (1H, br s), 4.13 (2H, q, J=8.1 Hz), 3.01 (2H, t, J=5.4 Hz), 2.98-2.80 (2H, m), 2.05-1.90 (2H, m), 1.70-1.60 (2H, m), 1.44 (9H, s), 1.25 (3H, t, J=8.1H), 1.55-1.20 (4H, m).

Step 2. Ethyl 3-[4-({[(3,3-dimethyl-2-oxo-2,3-dihydro-1H-indol-1-yl)carbonyl]amino}methyl)piperidin-1-yl]propanoate To a stirred solution of ethyl 3-(4-{[(tert-butoxycarbonyl) amino]methyl}piperidin-1-yl)propanoate (500 mg, 1.6 mmol, step 1 of Example 10) in CH$_2$Cl$_2$ (5 mL), trifluoroacetic acid (1.2 mL, 16 mmol) was added and stirred overnight at room temperature. The mixture was concentrated, and the residual oil was dissolved in CH$_2$Cl$_2$ (60 mL) and solid K$_2$CO$_3$ (5 g) was added, and stirred for 10 min. The mixture was filtered, and the filtrate was concentrated to give ethyl 3-[4-(aminomethyl)piperidin-1-yl]propanoate as a pale yellow oil. Following coupling reaction was carried out according to the procedure described in step 6 of Example 1 from 3,3-dimethyl-1,3-dihydro-2H-indol-2-one (Robertson, David W et al., *J. Med. Chem.*, 1986, 29, 1832) and ethyl 3-[4-(aminomethyl)piperidin-1-yl]propanoate.

MS (ESI) m/z: 428 (M+H)$^+$.

$^1$H-NMR (CDCl$_3$) δ: 8.73 (1H, br s), 8.25 (1H, d, J=8.1 Hz), 7.34-7.10 (2H, m), 4.13 (2H, q, J=8.1 Hz), 3.29 (2H, t, J=5.4 Hz), 2.98-2.85 (2H, m), 2.69 (2H, t, J=8.1 Hz), 2.49 (2H, t, J=8.1 Hz), 2.05-1.95 (2H, m), 1.81-1.70 (2H, m), 1.50-1.20 (13H, m).

Step 3. 3-[4-({[(3,3-Dimethyl-2-oxo-2,3-dihydro-1H-indol-1-yl)carbonyl]amino}methyl)piperidin-1-yl]propanoic Acid The title compound was prepared according to the procedure described in step 4 of Example 2 from ethyl 3-[4-({[(3, 3-dimethyl-2-oxo-2,3-dihydro-1H-indol-1-yl) carbonyl]amino}methyl)piperidin-1-yl]propanoate (step 2 of Example 10).

MS (ESI) m/z: 374 (M+H)$^+$.

IR (KBr) ν: 3315, 1733, 1606, 1541, 1460, 1379, 1344, 1269, 1163, 958, 769 cm$^{-1}$ $^1$H-NMR (CDCl$_3$) δ: 8.79 (1H, br s), 8.23 (1H, d, J=8.1 Hz), 7.40-7.15 (3H, m), 3.40-3.24 (2H, m), 3.20-3.18 (2H, m), 2.85-2.73 (2H, m), 2.39-2.21 (2H, m), 2.00-1.75 (3H, m), 1.55-1.30 (10H, m). Signal due to CO$_2$H was not observed.

Anal. Calcd. for C$_{20}$H$_{27}$N$_3$O$_4$.1.0H$_2$O.0.5MeOH.0.2CH$_2$Cl$_2$: C, 58.57; H, 7.46; N, 9.90. Found C, 58.94; H, 7.16; N, 9.81.

Example 11

3-[4-({[(3,3-DIMETHYL-2-OXO-2,3-DIHYDRO-1H-INDOL-1-YL)CARBONYL]AMINO}METHYL)PIPERIDIN-1-YL]-2,2-DIMETHYLPROPANOIC ACID

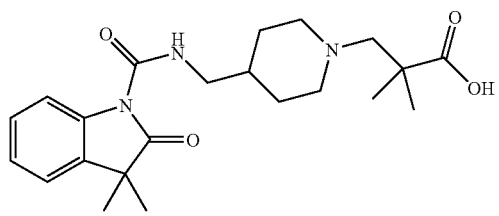

Step 1. tert-Butyl 4-({[(3,3-dimethyl-2-oxo-2,3-dihydro-1H-indol-1-yl)carbonyl]amino}methyl)piperidone-1-carboxylate The title compound was prepared according to the procedure described in step 6 of Example 1 from 3,3-dimethyl-1,3-dihydro-2H-indol-2-one (Robertson, David W et al., *J. Med. Chem.*, 1986, 29, 1832) and tert-butyl 4-(aminomethyl)piperidine-1-carboxylate.

MS (ESI) m/z: 402 (M+H)$^+$.

$^1$H-NMR (CDCl$_3$) δ: 8.76 (1H, br s), 8.24 (1H, d, J=8.1 Hz), 7.34-7.15 (3H, m), 4.25-4.03 (2H, m), 3.36-3.23 (2H, m), 2.79-2.60 (2H, m), 1.85-1.69 (2H, m), 1.55-1.36 (16H, m), 1.30-1.10 (2H, m).

Step 2. 3,3-Dimethyl-2-oxo-N-(piperidin-4-ylmethyl)indoline-1-carboxamide

The title compound was prepared according to the procedure described in step 2 of Example 2 from tert-butyl 4-({[(3,3-dimethyl-2-oxo-2,3-dihydro-1H-indol-1-yl)carbonyl]amino}methyl) piperidine-1-carboxylate (step 1 of Example 11).

MS (ESI) m/z: 302 (M+H)$^+$.

$^1$H-NMR (CDCl$_3$) δ: 8.74 (1H, br s), 8.25 (2H, d, J=8.1 Hz), 7.34-7.15 (3H, m), 3.29 (2H, t, J=5.4 Hz), 3.15-3.05 (2H, m), 2.67-2.55 (2H, m), 1.80-1.74 (2H, m), 1.43 (6H, s), 1.28-1.18 (2H, m). A signal due to NH (piperidine) was not observed.

Step 3. Methyl 3-[4-({[(3,3-dimethyl-2-oxo-2,3-dihydro-1H-indol-1-yl)carbonyl]amino}methyl)piperidin-1-yl]-2,2-dimethylpropanoate The title compound was prepared according to the procedure described in step 3 of Example 2 from 3,3-dimethyl-2-oxo-N-(piperidin-4-ylmethyl)indoline-1-carboxamide (step 2 of Example 11).

MS (ESI) m/z: 416 (M+H)$^+$.

$^1$H-NMR (CDCl$_3$) δ: 8.70 (1H, br s), 8.25 (1H, d, J=6.0 Hz), 7.33-7.15 (3H, m), 3.65 (3H, s), 3.25 (2H, t, J=6.0 Hz), 2.84-2.72 (2H, m), 2.46 (2H, s), 2.23-2.10 (3H, m), 1.73-1.54 (2H, m), 1.43 (6H, m), 1.38-1.24 (2H, m), 1.15 (6H, s).

Step 4. 3-[4-({[(3,3-Dimethyl-2-oxo-2,3-dihydro-1H-indol-1-yl)carbonyl]amino}methyl)piperidin-1-yl]-2,2-dimethylpropanoic Acid The title compound was prepared according to the procedure described in step 4 of Example 2 from methyl 3-[4-({[(3,3-dimethyl-2-oxo-2,3-dihydro-1H-indol-1-yl)carbonyl]amino}methyl) piperidin-1-yl]-2,2-dimethylpropanoate (step 3 of Example 11).

MS (ESI) m/z: 402 (M+H)$^+$.

m.p.: 164.5° C.

IR (KBr) ν: 3402, 3317, 2943, 2858, 1616, 1596, 1541, 1498, 1307, 1263, 1105, 985 cm$^{-1}$ $^1$H-NMR (CDCl$_3$) δ: 8.78 (1H, br s), 8.24 (1H, d, J=8.1 Hz), 7.34-7.18 (3H, m), 3.32 (2H, t, J=6.0 Hz), 3.24-3.06 (2H, m), 2.60-2.38 (4H, m), 1.97-1.65 (3H, m), 1.60-1.28 (8H, m), 1.24 (6H, s). A signal due to CO$_2$H was not observed.

Anal. Calcd. for C$_{22}$H$_{31}$N$_3$O$_4$: C, 65.81; H, 7.78; N, 10.47. Found: C, 65.56; H, 7.83; N, 10.36.

Example 12

3-[4-({[(3,3-DIMETHYL-2-OXO-2,3-DIHYDRO-1H-INDOL-1-YL)CARBONYL]AMINO}METHYL)-4-HYDROXYPIPERIDIN-1-YL]-2,2-DIMETHYLPROPANOIC ACID

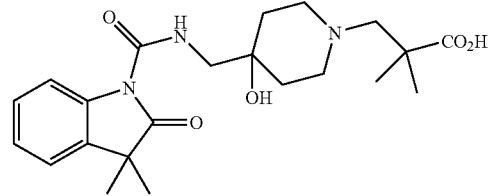

Step 1. N-[(1-benzyl-4-hydroxypiperidin-4-yl)methyl]-3,3-dimethyl-2-oxoindoline-1-carboxamide The title compound was prepared according to the procedure described in step 6 of Example 1 from 3,3-dimethyl-1,3-dihydro-2H-indol-2-one (Robertson, David W et al., *J. Med. Chem.*, 1986, 29, 1832) and 4-(aminomethyl)-1-benzylpiperidin-4-ol (Somanathan, R. et al., *Synth. Commun.*, 1994, 24, 1483)

MS (ESI) m/z: 408 (M+H)$^+$.

$^1$H-NMR (CDCl$_3$) δ: 8.93 (1H, br s), 8.23 (1H, d, J=8.1 Hz), 7.35-7.16 (8H, m), 5.30 (2H, s), 3.54 (2H, s), 3.45 (2H, d, J=5.4 Hz), 2.70-2.56 (2H, m), 2.46-2.33 (2H, m), 2.27 (1H, s), 1.80-1.67 (2H, m), 1.43 (6H, m).

Step 2. N-[(4-Hydroxypiperidin-4-yl)methyl]-3,3-dimethyl-2-oxoindoline-1-carboxamide A mixture of N-[(1-benzyl-4-hydroxypiperidin-4-yl)methyl]-3,3-dimethyl-2-oxoindoline-1-carboxamide (280 mg, 0.68 mmol, step 1 of Example 12) and palladium hydroxide (80 mg, 20 wt. % Pd on carbon,) in 10% HCl in methanol was stirred under $H_2$ atmosphere for 20 h. The mixture was filtered through a pad of Celite, washed with methanol and the filtrate was concentrated to give pale yellow oil. The residue was chromatographed on silica gel column eluting with $CH_2Cl_2$/methanol/$NH_4OH$ (10:1:0.2) to give 73 mg (34%) of the title compound as clear yellow oil.

MS (ESI) m/z: 318 (M+H)$^+$.

$^1$H-NMR (CDCl$_3$) δ: 8.95 (1H, br s), 8.25-8.16 (1H, m), 7.35-7.12 (3H, m), 3.51-3.40 (4H, m), 3.05-2.80 (4H, m), 1.75-1.55 (2H, m), 1.44 (6H, s).

Step 3. Methyl 3-[4-({[(3,3-dimethyl-2-oxo-2,3-dihydro-1H-indol-1-yl)carbonyl]amino}methyl)-4-hydroxypiperidin-1-yl]-2,2-dimethylpropanoate The title compound was prepared according to the procedure described in step 3 of Example 2 from N-[(4-hydroxypiperidin-4-yl)methyl]-3,3-dimethyl-2-oxoindoline-1-carboxamide (step 2 of Example 12).

Rf: 0.25 (aminopropyl-silica gel; hexane/ethyl acetate (2/1))

MS (ESI) m/z: 432 (M+H)$^+$.

Step 4. 3-[4-({[(3,3-Dimethyl-2-oxo-2,3-dihydro-1H-indol-1-yl)carbonyl]amino}methyl)-4-hydroxypiperidin-1-yl]-2,2-dimethylpropanoic Acid The title compound was prepared according to the procedure described in step 4 of Example 2 from methyl 3-[4-({[(3,3-dimethyl-2-oxo-2,3-dihydro-1H-indol-1-yl)carbonyl]amino}methyl)piperidin-1-yl]-2,2-dimethylpropanoate (step 3 of Example 12).

MS (ESI) m/z: 418 (M+H)$^+$.

$^1$H-NMR (CDCl$_3$) δ: 9.01 (1H, br s), 8.20 (1H, d, J=8.1 Hz), 7.33-7.15 (3H, m), 3.50-3.45 (2H, m), 3.00-2.85 (4H, m), 2.65-2.55 (2H, m), 1.81-1.45 (4H, m), 1.45 (6H, s), 1.25 (6H, s). Signals due to O$\underline{H}$ and CO$_2\underline{H}$ were not observed.

HRMS (FAB) (M+H)$^+$ calcd for $C_{22}H_{32}O_5N_3$ 418.2342, found 418.2356

Example 13

1-{[4-({[(2'-OXOSPIRO[CYCLOPENTANE-1,3'-INDOL]-1'(2'H)-YL)CARBONYL]AMINO}METHYL)PIPERIDIN-1-YL]METHYL}CYCLOHEXANECARBOXYLIC ACID

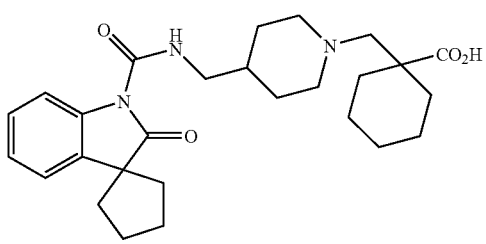

Step 1. Methyl 1-[(4-{[(tert-butoxycarbonyl)amino]methyl}piperidin-1-yl)methyl]cyclohexanecarboxylate The title compound was prepared with the similar method shown in the step 3 of Example 8 by using [cyclohexylidene(methoxy)methoxy](trimethyl)silane (Hannaby, Malcolm et al., *J. Chem. Soc. Perkin Trans.* 1, 1989, 303)

MS (ESI) m/z: 369 (M+H)$^+$.

$^1$H-NMR (CDCl$_3$) δ: 4.56 (1H, br s), 3.66 (3H, s), 2.97 (2H, t, J=6.1 Hz), 2.71 (2H, br d, J=11.7 Hz), 2.43 (2H, s), 2.11 (2H, br t, J=11.5 Hz), 2.03 (2H, br d, J=11.4 Hz), 1.65-1.10 (22H, m).

Step 2. Methyl 1-{[4-({[(2'-oxospiro[cyclopentane-1,3'-indol]-1'(2'H)-yl)carbonyl]amino}methyl)piperidin-1-yl]methyl}cyclohexanecarboxylate The title compound was prepared with the similar method shown in the step 2 of Example 10 from methyl 1-[(4-{[(tert-butoxycarbonyl)amino]methyl}piperidin-1-yl)methyl]cyclohexanecarboxylate (step 1 of Example 13).

MS (ESI) m/z: 482 (M+H)$^+$.

$^1$H-NMR (CDCl$_3$) δ: 8.71 (1H, br s), 8.23 (1H, d, J=9.0 Hz), 7.34-7.15 (3H, m), 3.66 (3H, s), 3.24 (2H, t, J=6.0 Hz), 2.80-2.68 (2H, m), 2.44 (2H, s), 2.25-1.15 (25H, m).

Step 3. 1-{[4-({[(2'-Oxospiro[cyclopentane-1,3'-indol]-1'(2'H)-yl)carbonyl]amino}methyl)piperidin-1-yl]methyl}cyclohexanecarboxylic Acid The title compound was prepared according to the procedure described in step 4 of Example 2 from methyl 1-{[4-({[(2'-oxospiro[cyclopentane-1,3'-indol]-1'(2'H)-yl)carbonyl]amino}methyl)piperidin-1-yl]methyl}cyclohexanecarboxylate (step 2 of Example 13).

MS (ESI) m/z: 468 (M+H)$^+$.

m.p.: 160.4° C.

IR (KBr) ν: 3300, 2923, 2862, 1728, 1600, 1552, 1469, 1346, 1265, 1222, 1143, 752 cm$^{-1}$ $^1$H-NMR (CDCl$_3$) δ: 8.80 (1H, br s), 8.21 (1H, d, J=9.0 Hz), 7.32-7.13 (3H, m), 3.30 (2H, t, J=6.0 Hz), 3.16-3.03 (2H, m), 2.60 (2H, s), 2.55-2.40 (2H, m), 2.27-1.26 (23H, m). A signal due to CO$_2\underline{H}$ was not observed.

Anal. Calcd. for $C_{27}H_{37}N_3O_4 \cdot 0.8H_2O$: C, 67.28; H, 8.07; N, 8.72. Found: C, 67.46; H, 8.05; N, 8.66.

Example 14

2'-OXO-N-[(1-{[1-(1H-TETRAZOL-5-YL)CYCLOPENTYL]METHYL}PIPERIDIN-4-YL)METHYL]SPIRO[CYCLOPENTANE-1,3'-INDOLE]-1'(2'H)-CARBOXAMIDE

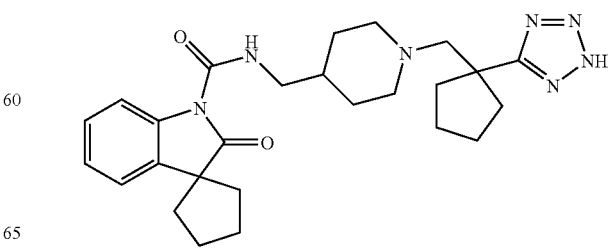

Step 1. α-Cyclopentyltetrazole-5-acetic Acid Ethyl Ester

To a stirred solution of 1-cyano-1-cyclopentanecarboxylic acid ethyl ester (6.19 g, 37.0 mmol, *Bioorg. Med. Chem. Lett.* 1999, 9, 369-374) in 1,4-dioxane (100 mL) was added $(CH_3CH_2CH_2CH_2)_3SnN_3$ (12.3 g, 37.0 mmol) at ambient temperature. The resulting mixture was refluxed for 15 h and concentrated under reduced pressure. To the resulting residue was added 4 M HCl in 1,4-dioxane (50 mL) and concentrated under reduced pressure. The resulting oil was washed twice with hexane to give crude product of the title compound as a yellow oil, which was used for next step without further purification.

Step 2. 2-Benzyl-α-cyclopentyl-2H-tetrazole-5-acetic Acid, Ethyl Ester

To a stirred mixture of α-cyclopentyltetrazole-5-acetic acid, ethyl ester (step 1 of Example 14) and $K_2CO_3$ (12.3 g, 89.0 mmol) in acetone (200 mL) was added benzyl bromide (4.84 mL, 40.7 mmol) at ambient temperature. The resulting mixture was stirred at 50° C. for 14 h and concentrated under reduced pressure. The resulting residue was chromatographed on a column of silica gel eluting with hexane/ethyl acetate (10:1) to give 2.95 g (27% in 2 steps) of the title compound.

MS (ESI) m/z: 301 (M+H)$^+$.

$^1$H NMR (CDCl$_3$) δ 7.45-7.23 (5H, m), 5.73 (2H, s), 4.11 (2H, q, J=7.1 Hz), 2.55-2.35 (4H, m), 1.88-1.56 (4H, m), 1.12 (3H, t, J=7.1 Hz).

Step 3. 2-Benzyl-α-cyclopentyl-2H-tetrazole-5-acetaldehyde

To a stirred mixture of 2-benzyl-α-cyclopentyl-2H-tetrazole-5-acetic acid, ethyl ester (2.92 g, 9.72 mmol, step 2 of Example 14) in CH$_2$Cl$_2$ (50 mL) at −78° C. was added diisobutylaluminium hydride (1.0 M in toluene, 22.5 mL, 22.5 mmol). The resulting mixture was stirred at −78° C. for 5 h. To the mixture were added 2 M aqueous HCl (50 mL) and saturated aqueous NH$_4$Cl (10 mL). The organic layer was separated, dried over magnesium sulfate, and concentrated under reduced pressure. The resulting residue was chromatographed on a column of silica gel eluting with Hexane/ethyl acetate (10:1) to give 862 mg (35%) of the title compound.

MS (ESI) m/z: 257 (M+H)$^+$.

$^1$H NMR (CDCl$_3$) δ 9.71 (1H, s), 7.50-7.30 (5H, m), 5.74 (2H, s), 2.45-2.18 (4H, m), 1.85-1.66 (4H, m).

Step 4. tert-Butyl[{1-(2-(2-benzyltetrazole)-2-cyclopentylmethyl)piperidin-4-yl}methyl]carbamate To a stirred solution of 2-benzyl-α-cyclopentyl-2H-tetrazole-5-acetaldehyde (850 mg, 3.32 mmol, step 3 of Example 14) and tert-butyl(piperidin-4-ylmethyl)carbamate (7.11 g, 33.2 mmol) in tetrahydrofuran (500 mL) were added NaBH(O(CO)CH$_3$)$_3$ (3.52 g, 16.6 mmol) and acetic acid (1.03 g, 16.9 mmol). The resulting mixture was stirred at 60° C. for 13 h and concentrated under reduced pressure. To the stirred residue were added saturated aqueous NaHCO$_3$ and CH$_2$Cl$_2$. The organic layer was separated, dried over magnesium sulfate, and concentrated under reduced pressure. The resulting residue was chromatographed on a column of silica gel eluting with hexane/ethyl acetate (1:1) to give 1.19 g (79%) of the title compound.

MS (ESI) m/z: 455 (M+H)$^+$.

$^1$H NMR (CDCl$_3$) δ 7.43-7.23 (5H, m), 5.72 (2H, s), 4.67 (1H, br t), 2.88 (2H, m), 2.66 (2H, br s), 2.48 (2H, m), 2.24 (2H, m), 1.93 (2H, m), 1.83 (2H, m), 1.78-1.48 (4H, m), 1.43 (9H, s), 1.37 (2H, m), 1.23 (1H, m), 0.94 (2H, m).

Step 5. ({1-[1-(2-Benzyl-2H-tetrazol-5-yl)cyclopentyl]piperidin-4-yl}methyl)amine A mixture of tert-butyl[{1-(2-(2-benzyltetrazole)-2-cyclopentylethyl)piperidin-4-yl}methyl]carbamate (150 mg, 0.34 mmol, step 4 of Example 14) and 10% HCl in methanol (10 mL) was stirred for 3 h at 60° C., and the mixture was concentrated to give yellow oil. The residue was chromatographed on a column of silica gel eluting with CH$_2$Cl$_2$/methanol/NH$_4$OH (12:1:0.1) to give 115 mg (quant.) of the title compound as clear yellow solid.

$^1$H NMR (CDCl$_3$) δ 7.50-7.25 (5H, m), 5.73 (2H, s), 2.67 (2H, s), 2.60-2.40 (4H, m), 2.35-2.16 (2H, m), 2.05-1.78 (4H, m), 1.75-1.34 (6H, m), 1.20-0.85 (3H, m).

Step 6. N-[(1-{[1-(2-Benzyl-2H-tetrazol-5-yl)cyclopentyl]methyl}piperidin-4-yl)methyl]-2'-oxospiro[cyclopentane-1,3'-indole]-1'(2'H)-carboxamide The title compound was prepared according to the procedure described in step 6 of Example 1 from ({1-[1-(2-benzyl-2H-tetrazol-5-yl)cyclopentyl]piperidin-4-yl}methyl)amine (step 5 of Example 14).

MS (ESI) m/z: 568 (M+H)$^+$.

$^1$H NMR (CDCl$_3$) δ 8.66 (1H, br s), 8.23 (1H, d, J=9.0 Hz), 7.40-7.15 (3H, m), 5.73 (2H, s), 3.15 (2H, t, J=6.0 Hz), 2.67 (2H, s), 2.54-2.44 (2H, m), 2.26-2.11 (4H, m), 2.10-1.76 (10H, m), 1.70-0.90 (14H, m).

Step 7. 2'-Oxo-N-[(1-{[1-(2H-tetrazol-5-yl)cyclopentyl]methyl}piperidin-4-yl)methyl]spiro[cyclopentane-1,3'-indole]-1'(2'H)-carboxamide A mixture of N-[(1-{[1-(2-benzyl-2H-tetrazol-5-yl)cyclopentyl]methyl}piperidin-4-yl)methyl]-2'-oxospiro[cyclopentane-1,3'-indole]-1'(2'H)-carboxamide (120 mg, 0.21 mmol, step 6 of Example 14) and palladium hydroxide (20 mg, 20 wt. % palladium on carbon) in methanol (10 mL) was stirred for 8 h under H$_2$ atmosphere. The mixture was filtered through a pad of Celite, and washed with methanol and the filtrate was concentrated to give a clear colorless oil. The residue was chromatographed on a column of silica gel eluting with CH$_2$Cl$_2$/methanol (16:1) to give 80 mg (80%) of the title compound as a white solid. The solid was triturated with ethyl acetate/hexane and collected by filtration to give 72 mg (72%) of the title compound as a white solid.

MS (ESI) m/z: 478 (M+H)$^+$.

IR (KBr) v: 3417, 2958, 1732, 1703, 1548, 1465, 1282, 1161, 769 cm$^{-1}$ $^1$H NMR (CDCl$_3$) δ 8.81 (1H, br s), 8.22 (1H, d, J=9.0 Hz), 7.34-7.12 (3H, m), 3.40-3.27 (2H, m), 3.16-3.05 (2H, m), 2.45-2.31 (2H, m), 3.00-1.65 (21H, m), 1.58-1.41 (2H, m). A signal due to tetrazole-H was not observed.

Anal. Calcd. for C$_{26}$H$_{35}$N$_7$O$_2$.1.0H$_2$O: C, 63.01; H, 7.52; N, 19.78. Found: C, 62.90; H, 7.35; N, 19.40.

Example 15

1-{[4-({[(6-FLUORO-3,3-DIMETHYL-2-OXO-2,3-DIHYDRO-1H-INDOL-1-YL)CARBONYL]AMINO}METHYL)PIPERIDIN-1-YL]METHYL}CYCLOBUTANECARBOXYLIC ACID

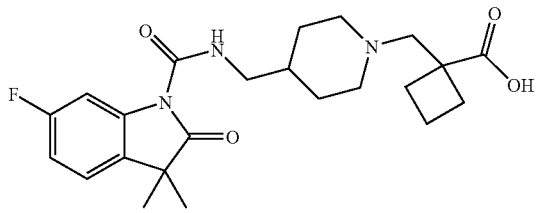

Step 1. Methyl 2-(4-fluoro-2-nitrophenyl)-2-methylpropanoate

A stirred mixture of methyl (4-fluoro-2-nitrophenyl)acetate (3.0 g, 0.014 mol, Quallich, George J et al., *Synthesis*, 1993, 351), methyl iodide (2 ml, 0.032 mol) and 18-crown-6 (925 mg, 3.5 mmol) in N,N-dimethylformamide (75 mL) was treated portion wise with NaH (1.28 g, 0.032 mol, 60% dispersion in mineral oil) at 0° C. Then the reaction mixture was stirred at room temperature for 2 h. It was quenched by addition of water. The aqueous layer was extracted with diethylether (25 mL×3). The organic layer was washed with water and brine, dried over sodium sulfate and concentrated in vacuo. The residue was chromatographed on a column of silica gel eluting with ethyl acetate/hexane (1:20 to 1:4) to give 2.52 g (75%) of the title compound as oil.

$^1$H-NMR (CDCl$_3$) δ: 7.67 (1H, dd, J=8.3, 2.9 Hz), 7.59 (1H, dd, J=8.9, 5.4 Hz), 7.39-7.29 (1H, m), 3.66 (3H, s), 1.66 (6H, s).

Step 2. 6-Fluoro-3,3-dimethyl-1,3-dihydro-2H-indol-2-one

A mixture of methyl 2-(4-fluoro-2-nitrophenyl)-2-methylpropanoate (2.53 g, 0.010 mol, step 1 of Example 15) and iron powder (2.34 g, 0.042 mol) in acetic acid (30 mL) was stirred at 100° C. for 5.5 h. The reaction mixture was rinsed with methanol and it was filtered through a pad of Celite. The filtrate was concentrated. It was added water and the aqueous layer was extracted with ethyl acetate (20 mL×3). The organic layer was washed with brine, dried over sodium sulfate and concentrated. The residue was chromatographed on a column of silica gel eluting with ethyl acetate/hexane (1:6 to 1:4) to give 1.67 g (89%) of the title compound as a white solid.

MS (ESI) m/z: 180 (M+H)$^+$, 178 (M−H)$^−$.

$^1$H-NMR (CDCl$_3$) δ: 7.84 (1H, br s), 7.12 (1H, dd, J=8.1, 5.3 Hz), 6.73 (1H, ddd, J=9.2, 8.1, 2.4 Hz), 6.65 (1H, dd, J=8.8, 2.4 Hz), 1.39 (6H, s).

Step 3. 1-{[4-({[(6-Fluoro-3,3-dimethyl-2-oxo-2,3-dihydro-1H-indol-1-yl)carbonyl]amino}methyl)piperidin-1-yl]methyl}cyclobutanecarboxylic Acid The title compound was prepared according to the procedure described in step 6 of Example 1 from 6-fluoro-3,3-dimethyl-1,3-dihydro-2H-indol-2-one (step 2 of Example 15) and 1-{[4-(aminomethyl)piperidin-1-yl]methyl}cyclobutanecarboxylic acid 4-methylbenzenesulfonate (step 3 of Example 7).

MS (ESI) m/z: 432 (M+H)$^+$.
m.p.: 193° C.
IR (KBr) ν: 3300, 2934, 1740, 1605, 1547, 1477, 1385, 1352, 1304, 1236, 1151 cm$^{-1}$.

$^1$H-NMR (CDCl$_3$) δ: 8.71 (1H, t, J=5.9 Hz), 8.03 (1H, dd, J=10.2, 2.5 Hz), 7.15 (1H, dd, J=8.2, 5.4 Hz), 6.94-6.84 (1H, m), 3.31 (2H, t, J=5.9 Hz), 3.13-3.00 (2H, m), 2.78 (2H, s), 2.61-2.44 (2H, m), 2.44-2.24 (3H, m), 2.01-1.80 (5H, m), 1.82-1.65 (1H, m), 1.54-1.42 (2H, m), 1.42 (6H, s). A signal due to CO$_2$H was not observed.

Anal. Calcd. for C$_{23}$H$_{30}$N$_3$O$_4$F.0.7H$_2$O: C, 62.20; H, 7.13; N, 9.46. Found: C, 61.85; H, 7.14; N, 9.34.

Example 16

3-[4-({[(6-FLUORO-3,3-DIMETHYL-2-OXO-2,3-DIHYDRO-1H-INDOL-1-YL)CARBONYL]AMINO}METHYL)PIPERIDIN-1-YL]PROPANOIC ACID

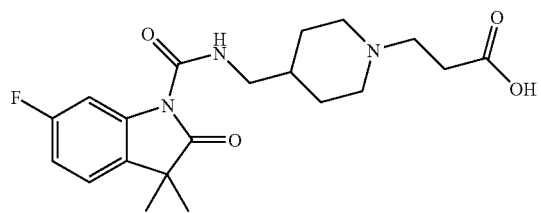

Step 1. Ethyl 3-[4-({[(6-fluoro-3,3-dimethyl-2-oxo-2,3-dihydro-1H-indol-1-yl)carbonyl]amino}methyl)piperidin-1-yl]propanoate The title compound was prepared according to the procedure described in step 6 of Example 1 from 6-fluoro-3,3-dimethyl-1,3-dihydro-2H-indol-2-one (step 2 in Example 15) and ethyl 3-[4-(aminomethyl) piperidin-1-yl]propanoate (step 2 in Example 10).

MS (ESI) m/z: 420 (M+H)$^+$.

$^1$H-NMR (CDCl$_3$) δ: 8.67 (1H, br s), 8.05 (1H, dd, J=10.2, 2.6 Hz), 7.14 (1H, dd, J=7.7, 5.4 Hz), 6.93-6.84 (1H, m), 4.14 (2H, dd, J=14.3, 7.2 Hz), 3.29 (2H, t, J=6.2 Hz), 2.96-2.86 (2H, m), 2.70 (2H, t, J=7.5 Hz), 2.50 (2H, t, J=7.5 Hz), 2.06-1.93 (2H, m), 1.82-1.65 (2H, m), 1.43-1.28 (2H, m), 1.42 (6H, s), 1.27 (3H, t, J=14.3 Hz). A signal due to CH was not observed.

Step 2. 3-[4-({[(6-Fluoro-3,3-dimethyl-2-oxo-2,3-dihydro-1H-indol-1-yl)carbonyl]amino}methyl)piperidin-1-yl]propanoic Acid The title compound was prepared according to the procedure described in step 4 of Example 2 from ethyl 3-[4-({[(6-fluoro-3,3-dimethyl-2-oxo-2,3-dihydro-1H-indol-1-yl)carbonyl]amino}methyl) piperidin-1-yl]propanoate (step 1 of Example 16).

MS (ESI) m/z: 392 (M+H)$^+$.
IR (KBr) ν: 3317, 2972, 2937, 1728, 1603, 1545, 1493, 1385, 1354, 1304, 1273, 1155, 1111, 1072 cm$^{-1}$.

$^1$H-NMR (CDCl$_3$) δ: 8.72 (1H, br s), 8.03 (1H, dd, J=10.5, 2.5 Hz), 7.15 (1H, dd, J=8.5, 5.4 Hz), 8.89 (1H, dt, J=8.5, 2.5 Hz), 3.23 (2H, t, J=6.3 Hz), 3.25-3.12 (2H, m), 2.79 (2H, t,

J=6.3 Hz), 2.53 (2H, t, J=6.3 Hz), 2.38-2.24 (2H, m), 1.99-1.86 (2H, m), 1.90-1.70 (1H, m), 1.56-1.35 (2H, m), 1.43 (6H, s). A signal due to CO$_2$H was not observed.

HRMS (ESI) m/z calcd for C$_{20}$H$_{27}$FN$_3$O$_4$ ([M+H]$^+$) 392.1986, found 392.1993.

Example 17

3-[4-({[(6-FLUORO-3,3-DIMETHYL-2-OXO-2,3-DIHYDRO-1H-INDOL-1-YL)CARBONYL]AMINO}METHYL)PIPERIDIN-1-YL]-2,2-DIMETHYLPROPANOIC ACID

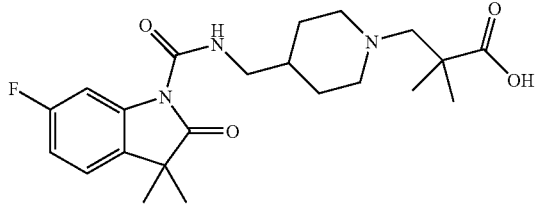

Step 1. tert-Butyl 4-({[(6-fluoro-3,3-dimethyl-2-oxo-2,3-dihydro-1H-indol-1-yl)carbonyl]amino}methyl)piperidine-1-carboxylate The title compound was prepared according to the procedure described in step 6 of Example 1 from 6-fluoro-3,3-dimethyl-1,3-dihydro-2H-indol-2-one (step 2 of Example 15) and tert-butyl 4-(aminomethyl)piperidine-1-carboxylate.

$^1$H-NMR (CDCl$_3$) δ: 8.69 (1H, t, J=5.5 Hz), 8.04 (1H, dd, J=10.2, 2.4 Hz), 7.15 (1H, dd, J=8.3, 5.5 Hz), 6.92-6.84 (1H, m), 4.24-4.03 (2H, m), 3.34-3.24 (2H, m), 2.78-2.60 (2H, m), 1.80-1.64 (3H, m), 1.46 (9H, s), 1.42 (6H, s), 1.29-1.10 (2H, m).

Step 2. 6-Fluoro-3,3-dimethyl-2-oxo-N-(piperidin-4-ylmethyl)indoline-1-carboxamide The title compound was prepared according to the procedure described in step 2 of Example 2 from tert-butyl 4-({[(6-fluoro-3,3-dimethyl-2-oxo-2,3-dihydro-1H-indol-1-yl)carbonyl]amino}methyl) piperidine-1-carboxylate (step 1 of Example 17).

MS (ESI) m/z: 320 (M+H)$^+$.

$^1$H-NMR (CDCl$_3$) δ: 8.68 (1H, br s), 8.05 (1H, dd, J=10.3, 2.4 Hz), 7.15 (1H, dd, J=(1H, m), 3.29 (2H, t, J=6.0 Hz), 3.25-3.08 (2H, m), 2.65 (2H, dt, J=12.2, 2.3 Hz), 1.89-1.65 (3H, m) 1.42 (6H, s), 1.40-1.15 (2H, m).

Step 3. Methyl 3-[4-({[(6-fluoro-3,3-dimethyl-2-oxo-2,3-dihydro-1H-indol-1-yl)carbonyl]amino}methyl)piperidin-1-yl]-2,2-dimethylpropanoate The title compound was prepared according to the procedure described in step 3 of Example 2 from 6-fluoro-3,3-dimethyl-2-oxo-N-(piperidin-4-ylmethyl)indoline-1-carboxamide (step 2 of Example 17).

MS (ESI) m/z: 434 (M+H)$^+$.

$^1$H-NMR (CDCl$_3$) δ: 8.63 (1H, br s), 8.05 (1H, dd, J=10.4, 2.5 Hz), 7.14 (1H, dd, J=8.3, 5.5 Hz), 6.92-6.83 (1H, m), 3.66 (3H, s), 3.25 (2H, t, J=6.3 Hz), 2.83-2.73 (2H, m), 2.47 (2H, s) 2.16 (2H, dt, J=11.6, 2.0 Hz), 1.71-1.56 (2H, m) 1.56-1.44 (1H, m), 1.42 (6H, s), 1.36-1.22 (2H, m), 1.15 (6H, s).

Step 4. 3-[4-({[(6-Fluoro-3,3-dimethyl-2-oxo-2,3-dihydro-1H-indol-1-yl)carbonyl]amino}methyl)piperidin-1-yl]-2,2-dimethylpropanoic Acid The title compound was prepared according to the procedure described in step 4 of Example 2 from methyl 3-[4-({[(6-fluoro-3,3-dimethyl-2-oxo-2,3-dihydro-1H-indol-1-yl)carbonyl]amino}methyl) piperidin-1-yl]-2,2-dimethylpropanoate (step 3 of Example 17).

m.p.: 134° C.

MS (ESI) m/z: 420 (M+H)$^+$.

IR (KBr) ν: 3319, 2974, 2930, 1736, 1605, 1545, 1497, 1439, 1350, 1302, 1275, 1231, 1153 cm$^{-1}$.

$^1$H-NMR (DMSO) δ: 8.55 (1H, t, J=6.1 Hz), 7.83 (1H, dd, J=10.6, 2.6 Hz), 7.48 (1H, dd, J=8.3, 5.8 Hz), 7.03 (1H, ddd, J=9.4, 8.3, 2.6 Hz), 3.18 (2H, t, J=6.1 Hz), 2.91-2.80 (2H, m), 2.45 (2H, s), 2.24-2.12 (2H, m), 1.67-1.56 (2H, m) 1.60-1.45 (1H, m), 1.36 (6H, s), 1.28-1.10 (2H, s), 1.06 (6H, s). A signal due to CO$_2$H was not observed.

Anal. Calcd. for C$_{22}$H$_{30}$FN$_3$O$_4$: C, 62.99; H, 7.21; N, 10.02. Found: C, 62.66; H, 7.27; N, 9.90.

Example 18

[4-({[(6-FLUORO-3,3-DIMETHYL-2-OXO-2,3-DIHYDRO-1H-INDOL-1-YL)CARBONYL]AMINO}METHYL)PIPERIDIN-1-YL]-ACETIC ACID

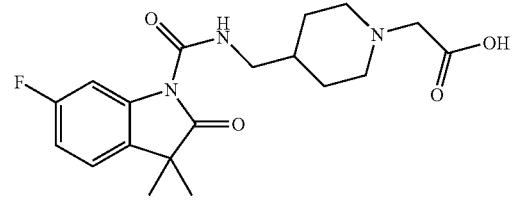

Step 1. tert-Butyl[4-({[(6-fluoro-3,3-dimethyl-2-oxo-2,3-dihydro-1H-indol-1-yl)carbonyl]amino}methyl)piperidin-1-yl]acetate A solution of 6-fluoro-3,3-dimethyl-2-oxo-N-(piperidin-4-ylmethyl)indoline-1-carboxamide (200 mg, 0.63 mmol, step 2 in Example 17) and triethylamine (114 μL, 0.82 mmol) in tetrahydrofuran (3 mL) was stirred at 0° C., it was slowly added tert-butyl bromoacetate (111 μL, 0.75 mmol). The reaction mixture was stirred at room temperature for 5 h and at 35° C. for 4 h. It was further added triethylamine (17 μL, 0.12 mmol) and tert-butyl bromoacetate (18 μL, 0.12 mmol). The solution was stirred at room temperature overnight. The resulting solution was added sat. sodium bicarbonate. It was extracted with ethyl acetate (10 mL×3). The organic phase was washed with brine, dried over sodium sulfate and concentrated. The residue was chromatographed on a column of aminopropyl-silica gel eluting with ethyl acetate/hexane (1:10 to 1:6) to give 203 mg (74%) of the titled compound.

MS (ESI) m/z: 434 (M+H)$^+$.

$^1$H-NMR (CDCl$_3$) δ: 8.67 (1H, t, J=6.1 Hz), 8.05 (1H, dd, J=10.4, 2.5 Hz), 7.14 (1H, dd, J=8.3, 5.6 Hz), 6.87 (1H, dt, J=8.7, 2.5 Hz), 3.30 (2H, t, J=6.1 Hz), 3.11 (2H, s), 3.02-2.92

(2H, m), 2.16 (2H, dt, J=11.6, 2.3 Hz), 1.80-1.69 (2H, m), 1.54-1.33 (3H, m), 1.46 (9H, s), 1.42 (6H, s).

Step 2. [4-({[(6-Fluoro-3,3-dimethyl-2-oxo-2,3-dihydro-1H-indol-1-yl)carbonyl]amino}methyl)piperidin-1-yl]acetic Acid A mixture of tert-butyl[4-({[(6-fluoro-3,3-dimethyl-2-oxo-2,3-dihydro-1H-indol-1-yl)carbonyl]amino}methyl)piperidin-1-yl]acetate (200 mg, 0.46 mmol, step 1 of Example 18) and trifluoroacetic acid (106 μL, 1.38 mmol) in $CH_2Cl_2$ (1 mL) was stirred at room temperature overnight. The resulting solution was neutralized by addition of sodium bicarbonate (116 mg) and it was concentrated. The desired product was dissolved with $CH_2Cl_2$/methanol=8/1 solution and filtrated. The filtrate was concentrated. The residue was chromatographed on preparative TLC eluting with methanol/dichloromethane (1:7) to give 115 mg (66%) as white gum.

MS (ESI) m/z: 378 $(M+H)^+$.

IR (KBr) ν: 3315, 2937, 2872, 1732, 1686, 1638, 1543, 1497, 1408, 1304, 1275, 1304, 1205, 1130 $cm^{-1}$.

$^1$H-NMR ($CDCl_3$) δ: 8.69 (1H, t, J=5.9 Hz), 7.96 (1H, dd, J=10.3, 2.4 Hz), 7.11 (1H, dd, J=8.5, 5.6 Hz), 6.83 (1H, dt, J=8.5, 2.4 Hz), 3.75-3.54 (3H, br), 3.37-3.23 (2H, br), 2.90-2.64 (2H, br), 2.55-1.53 (6H, br), 1.38 (6H, s). A signal due to $CO_2\underline{H}$ was not observed.

HRMS (ESI) m/z calcd for $C_{19}H_{25}FN_3O_4$ $([M+H]^+)$ 378.1829, found 378.1816.

Example 19

2-[4-({[(6-FLUORO-3,3-DIMETHYL-2-OXO-2,3-DIHYDRO-1H-INDOL-1-YL)CARBONYL]AMINO}METHYL)PIPERIDIN-1-YL]-2-METHYLPROPANOIC ACID

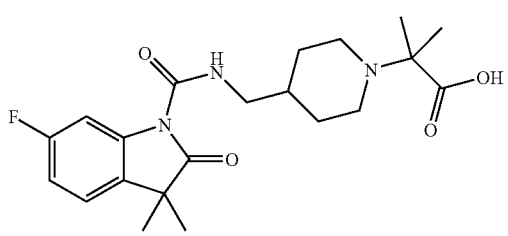

Step 1. tert-Butyl 2-methyl-2-(4-oxopiperidin-1-yl)propanoate

The title compound was prepared according to the procedure described in step 3 of Example 1 from tert-butyl 2-methylalaninate.

$^1$H-NMR ($CDCl_3$) δ: 2.95-2.85 (4H, m), 2.48-2.40 (4H, m), 1.47 (9H, s), 1.35 (6H, s).

Step 2. tert-Butyl 2-(4-cyanopiperidin-1-yl)-2-methylpropanoate

The title compound was prepared according to the procedure described in step 4 of Example 1 from tert-butyl 2-methyl-2-(4-oxopiperidin-1-yl)propanoate (step 1 of Example 19).

$^1$H-NMR ($CDCl_3$) δ: 2.93-2.76 (2H, m), 2.68-2.45 (3H, m), 2.00-1.75 (4H, m), 1.47 (9H, s), 1.27 (6H, s).

Step 3. tert-Butyl 2-[4-(aminomethyl)piperidin-1-yl]-2-methylpropanoate

The title compound was prepared according to the procedure described in step 5 of Example 1 from tert-butyl 2-(4-cyanopiperidin-1-yl)-2-methylpropanoate (step 2 of Example 19).

MS (ESI) m/z: 257 $(M+H)^+$.

$^1$H-NMR ($CDCl_3$) δ: 3.07-2.96 (2H, m), 2.56 (2H, d, J=5.9 Hz), 2.25-2.13 (2H, m), 1.80-1.65 (3H, m), 1.46 (9H, s), 1.27 (6H, s), 1.30-1.10 (2H, m). Signal due to $N\underline{H}_2$ were not observed.

Step 4. tert-Butyl 2-[4-({[(6-fluoro-3,3-dimethyl-2-oxo-2,3-dihydro-1H-indol-1-yl)carbonyl]amino}methyl)piperidin-1-yl]-2-methylpropanoate The title compound was prepared according to the procedure described in step 6 of Example 1 from 6-fluoro-3,3-dimethyl-1,3-dihydro-2H-indol-2-one (step 2 of Example 15) and tert-butyl 2-[4-(aminomethyl)piperidin-1-yl]-2-methylpropanoate (step 3 of Example 19).

MS (ESI) m/z: 462 $(M+H)^+$.

$^1$H-NMR ($CDCl_3$) δ: 8.65 (1H, br s), 8.05 (1H, dd, J=10.5, 2.5 Hz), 7.14 (1H, dd, J=8.3, 5.5 Hz), 6.88 (1H, dt, J=8.6, 2.5 Hz), 3.28 (2H, t, J=6.2 Hz), 3.10-2.98 (2H, m), 2.28-2.13 (2H, m), 1.83-1.64 (3H, m), 1.46 (9H, s), 1.42 (6H, s), 1.45-1.25 (2H, m), 1.27 (6H, s).

Step 5. 2-[4-({[(6-Fluoro-3,3-dimethyl-2-oxo-2,3-dihydro-1H-indol-1-yl)carbonyl]amino}methyl)piperidin-1-yl]-2-methylpropanoic Acid The title compound was prepared according to the procedure described in step 4 of Example 2 from tert-butyl 2-[4-({[(6-fluoro-3,3-dimethyl-2-oxo-2,3-dihydro-1H-indol-1-yl)carbonyl]amino}methyl) piperidin-1-yl]-2-methylpropanoate (step 4 of Example 19).

m.p.: 213° C.

IR (KBr) ν: 3271, 2934, 1736, 1632, 1560, 1495, 1441, 1346, 1302, 1231, 1151 $cm^{-1}$.

MS (ESI) m/z: 406 $(M+H)^+$.

$^1$H-NMR (DMSO) δ: 8.59 (1H, t, J=6.0 Hz), 7.83 (1H, dd, J=10.7, 2.5 Hz), 7.47 (1H, dd, J=8.3, 5.8 Hz), 7.04 (1H, ddd, J=9.4, 8.3, 2.5 Hz), 3.23-3.53 (4H, m), 2.70-2.56 (2H, m), 1.85-1.65 (3H, m), 1.63-1.40 (2H, m), 1.55-1.42 (1H, m), 1.37 (6H, s), 1.23 (6H, s). A signal due to $CO_2\underline{H}$ was not observed.

Anal. Calcd. for $C_{21}H_{28}FN_3O_4 \cdot 0.2H_2O$: C, 61.66; H, 7.00; N, 10.27. Found: C, 61.26; H, 6.90; N, 10.14.

Example 20

3-[4-FLUORO-4-({[(6-FLUORO-3,3-DIMETHYL-2-OXO-2,3-DIHYDRO-1H-INDOL-1-YL)CARBONYL]AMINO}METHYL)PIPERIDIN-1-YL]-2,2-DIMETHYLPROPANOIC ACID

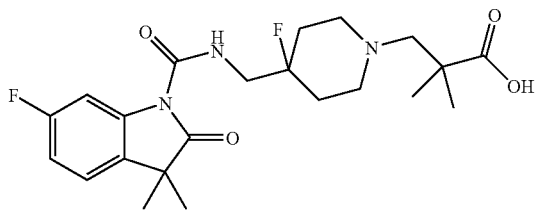

Step 1. N-benzoyl-4-tert-butoxycarbonylaminomethyl-4-fluoropiperidine

A mixture of N-benzoyl-4-aminomethyl-4-fluoropiperidine (*J. Med. Chem.* 1999, 42, 1648-1660.) (3.54 g, 15.0 mmol) and di-tert-butyl dicarbonate (4.91 g, 22.5 mmol) in methanol (80 mL) was stirred at room temperature for 15 h and concentrated in vacuo. The resulting residue was chromatographed on a column of silica gel eluting with hexane/ethyl acetate (1:1) to give 4.52 g (89%) of the title compound as colorless oil.
MS (ESI) m/z: 337 (M+H)$^+$.
$^1$H NMR (CDCl$_3$) δ 7.55-7.25 (5H, m), 5.16 (1H, br t, J=6.3 Hz), 4.51 (1H, m), 3.62 (1H, m), 3.55-3.00 (4H, m), 2.10-1.25 (4H, m), 1.43 (9H, s).

Step 2. 4-tert-Butoxycarbonylaminomethyl-4-fluoropiperidine

A mixture of N-benzoyl-4-tert-butoxycarbonylaminomethyl-4-fluoro piperidine (step 3 of Example 15) (4.42 g, 13.1 mmol), NaOH (2.62 g, 65.5 mmol), H$_2$O (9.00 mL) and ethanol (90.0 mL) was refluxed for 15 h and concentrated in vacuo. To the resulting residue were added water and chloroform. The organic layer was separated, dried over magnesium sulfate, and concentrated under reduced pressure. Recrystallization of the resulting solid with hexane-CH$_2$Cl$_2$ afforded colorless solid 1.77 g (58%) as the title compound.
MS (ESI) m/z: 233 (M+H)$^+$.
$^1$H NMR (CDCl$_3$) δ 4.93 (1H, m), 3.30 (2H, dd, J=21.5, 6.3 Hz), 2.91 (4H, m), 1.88-1.34 (4H, m), 1.45 (9 H, s). A signal due to NH and was not observed.

Step 3. Methyl 3-(4-{[(tert-butoxycarbonyl)amino]methyl}-4-fluoropiperidin-1-yl)-2,2-dimethylpropanoate The title compound was prepared according to the procedure described in step 3 of Example 2 from 4-tert-Butoxycarbonylaminomethyl-4-fluoropiperidine (step 2 of Example 20).

$^1$H-NMR (CDCl$_3$) δ: 4.78 (1H, br s), 3.66 (3H, s), 3.27 (2H, dd, J=22.1, 6.3 Hz), 2.50 (2H, s), 2.64-2.35 (4H, m), 1.77-1.50 (4H, m), 1.44 (9H, s), 1.15 (6H, s). A signal due to NH was not observed.

Step 4. Methyl 3-[4-(aminomethyl)-4-fluoropiperidin-1-yl]-2,2-dimethylpropanoate The title compound was prepared according to the procedure described in step 2 of Example 2 from methyl 3-(4-{[(tert-butoxycarbonyl)amino]methyl}-4-fluoro piperidin-1-yl)-2,2-dimethylpropanoate (step 3 of Example 20).
MS (ESI) m/z: 247 (M+H)$^+$.
$^1$H-NMR (CDCl$_3$) δ: 3.66 (3H, s), 2.74 (2H, d, J=20.4 Hz), 2.65-2.41 (4H, m), 2.51 (2H, s), 1.87-1.20 (4H, m), 1.16 (6H, s). A signal due to NH$_2$ was not observed.

Step 5. Methyl 3-[4-fluoro-4-({[(6-fluoro-3,3-dimethyl-2-oxo-2,3-dihydro-1H-indol-1-yl)carbonyl]amino}methyl)piperidin-1-yl]-2,2-dimethylpropanoate The title compound was prepared according to the procedure described in step 6 of Example 1 from 6-fluoro-3,3-dimethyl-1,3-dihydro-2H-indol-2-one (step 2 Example 15) and methyl 3-[4-(aminomethyl)-4-fluoropiperidin-1-yl]-2,2-dimethyl propanoate (step 4 of Example 20).
MS (ESI) m/z: 452 (M+H)$^+$.
$^1$H-NMR (CDCl$_3$) δ: 8.81 (1H, t, J=5.3 Hz), 8.03 (1H, dd, J=10.6, 2.5 Hz), 7.15 (1H, dd, J=8.4, 5.6 Hz), 6.88 (1H, dt, J=8.4, 2.5 Hz), 3.66 (3H, s), 3.56 (2H, dd, J=21.1, 5.9 Hz), 2.68-2.45 (4H, m), 2.51 (2H, s), 1.89-1.58 (4H, m), 1.43 (6H, s) 1.15 (6H, s).

Step 6. 3-[4-Fluoro-4-({[(6-fluoro-3,3-dimethyl-2-oxo-2,3-dihydro-1H-indol-1-yl)carbonyl]amino}methyl)piperidin-1-yl]-2,2-dimethylpropanoic Acid The title compound was prepared according to the procedure described in step 4 of Example 2 from methyl 3-[4-fluoro-4-({[(6-fluoro-3,3-dimethyl-2-oxo-2,3-dihydro-1H-indol-1-yl)carbonyl]amino}methyl) piperidin-1-yl]-2,2-dimethylpropanoate (step 5 of Example 20).
m.p.: 176° C.
IR (KBr) ν: 3319, 2974, 2937, 1734, 1607, 1543, 1497, 1352, 1304, 1273, 1232, 1153, 1092 cm$^{-1}$.
MS (ESI) m/z: 438 (M+H)$^+$.
$^1$H-NMR (CDCl$_3$) δ: 8.87 (1H, t, J=6.3 Hz), 8.02 (1H, dd, J=10.2, 2.5 Hz), 7.16 (1H, dd, J=8.4, 5.6 Hz), 6.90 (1H, dt, J=8.4, 2.5 Hz), 3.63 (2H, dd, J=20.7, 6.3 Hz), 3.04-2.94 (2H, m), 2.86-2.72 (2H, m), 2.59 (2H, s), 2.05-1.74 (4H, m), 1.44 (6H, s), 1.24 (6H, s). A signal due to CO$_2$H was not observed.
Anal. Calcd. for C$_{22}$H$_{29}$F$_2$N$_3$O$_4$.0.1H$_2$O: C, 60.15; H, 6.70; N, 9.57. Found: C, 59.95; H, 6.67; N, 9.37.

Example 21

3-[4-({[(3,3-DIMETHYL-2-OXO-2,3-DIHYDRO-1H-INDOL-1-YL)CARBONYL]AMINO}METHYL)-4-FLUOROPIPERIDIN-1-YL]-2,2-DIMETHYLPROPANOIC ACID

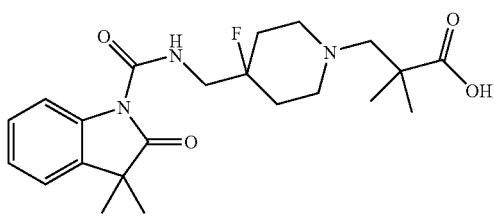

Step 1. Methyl 3-[4-({[(3,3-dimethyl-2-oxo-2,3-dihydro-1H-indol-1-yl)carbonyl]amino}methyl)-4-fluoropiperidin-1-yl]-2,2-dimethylpropanoate The title compound was prepared according to the procedure described in step 6 of Example 1 from 3,3-dimethyl-1,3-dihydro-2H-indol-2-one (Robertson, David W et al., *J. Med. Chem.*, 1986, 29, 1832) and methyl 3-[4-(aminomethyl)-4-fluoropiperidin-1-yl]-2,2-dimethylpropanoate (step 4 of Example 20).

MS (ESI) m/z: 434 (M+H)+.

$^1$H-NMR (CDCl$_3$) δ: 8.88 (1H, t, J=5.9 Hz), 8.24 (1H, d, J=7.9 Hz), 7.34-7.14 (3H, m), 3.66 (3H, s), 3.57 (2H, dd, J=21.1, 5.9 Hz), 2.67-2.45 (4H, m), 2.51 (2H, s), 1.90-1.53 (4H, m), 1.44 (6H, s) 1.15 (6H, s).

Step 2. 3-[4-({[(3,3-Dimethyl-2-oxo-2,3-dihydro-1H-indol-1-yl)carbonyl]amino}methyl)-4-fluoropiperidin-1-yl]-2,2-dimethylpropanoic Acid The title compound was prepared according to the procedure described in step 4 of Example 2 from methyl 3-[4-({[(3,3-dimethyl-2-oxo-2,3-dihydro-1H-indol-1-yl)carbonyl]amino}methyl)-4-fluoropiperidin-1-yl]-2,2-dimethylpropanoate (step 1 of Example 21).

m.p.: 156° C.

IR (KBr) ν: 3306, 2972, 1736, 1543, 1460, 1344, 1271, 1229, 1159, 770 cm$^{-1}$.

MS (ESI) m/z: 420 (M+H)+.

$^1$H-NMR (CDCl$_3$) δ: 8.94 (1H, t, J=4.9 Hz), 8.23 (1H, d, J=8.6 Hz), 7.36-7.15 (3H, m), 3.64 (2H, dd, J=21.1, 5.9 Hz), 3.04-2.92 (2H, m), 2.86-2.69 (2H, m), 2.59 (2H, s), 2.15-1.65 (4H, m), 1.45 (6H, s), 1.24 (6H, s). A signal due to CO$_2$H was not observed.

Anal. Calcd. for C$_{22}$H$_{30}$FN$_3$O$_4$.0.1H$_2$O: C, 62.72; H, 7.23; N, 9.97. Found: C, 62.32; H, 7.22; N, 9.74.

Example 22

1-{[4-({[(6-FLUORO-3,3-DIMETHYL-2-OXO-2,3-DIHYDRO-1H-INDOL-1-YL)CARBONYL]AMINO}METHYL)-4-HYDROXYPIPERIDIN-1-YL]METHYL}CYCLOBUTANECARBOXYLIC ACID

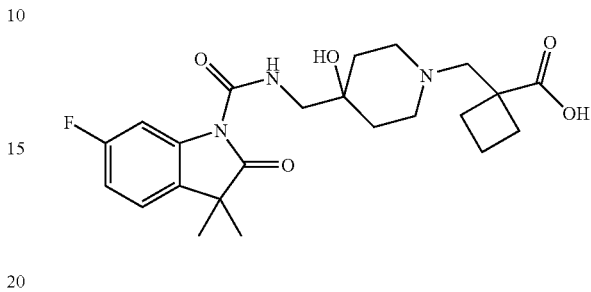

Step 1. tert-Butyl 4-cyano-4-hydroxypiperidine-1-carboxylate

To a suspension of tert-butyl 4-oxopiperidine-1-carboxylate (2.0 g, 10 mmol) in diethyl ether (40 mL), a solution of NaCN (0.54 g, 11 mmol) and NaHCO$_3$ (1.7 g, 20 mmol) in water (25 mL) was added slowly with vigorous stirring at room temperature. The mixture was stirred overnight, and extracted with Et$_2$O (30 mL×2). The organic phase was washed with water (50 mL), brine (50 mL) and dried over MgSO$_4$, filtered and evaporated gave 2.1 g of the title compound as clear colorless oil.

$^1$H-NMR (CDCl$_3$) δ: 3.81-3.72 (2H, m), 3.42-3.32 (2H, m), 2.18-2.00 (2H, m), 1.88-1.77 (2H, m), 1.46 (9H, s).

$^{13}$C-NMR (CDCl$_3$) δ: 154.67, 121.13, 80.57, 67.15, 36.57, 28.23.

Step 2. tert-Butyl 4-(aminomethyl)-4-hydroxypiperidine-1-carboxylate

To a suspension of lithium aluminum hydride (84 mg, 2.2 mmol) in THF (5 mL), a solution of tert-butyl 4-cyano-4-hydroxypiperidine-1-carboxylate (200 mg, 0.88 mmol, step 1 of Example 22) in THF (1 mL) was added dropwise at 0° C. The mixture was stirred for 1 h at that temperature and Na$_2$SO$_4$.10H$_2$O (400 mg) was added slowly, and the mixture was stirred for 5 h at room temperature. The mixture was filtered though a pad of Celite, washed with CH$_2$Cl$_2$ (20 mL×2), the filtrate was concentrated to give clear colorless oil. The residue was chromatographed on a column of silica gel eluting with CH$_2$Cl$_2$/MeOH/NH$_4$OH (14:1:0.1) to give 120 mg (59%) of the title compound as white solid.

$^1$H-NMR (CDCl$_3$) δ: 3.98-3.75 (2H, m), 3.17 (2H, t, J=10.8 Hz), 2.56 (2H, s), 1.46 (9H, s), 1.60-1.25 (4H, m). Signals due to O<u>H</u> and N<u>H</u>$_2$ were not observed.

Step 3. tert-Butyl 4-({[(6-fluoro-3,3-dimethyl-2-oxo-2,3-dihydro-1H-indol-1-yl)carbonyl]amino}methyl)-4-hydroxypiperidine-1-carboxylate The title compound was prepared according to the procedure described in step 6 of Example 1 from 6-fluoro-3,3-dimethyl-1,3-dihydro-2H-indol-2-one (step 2 Example 15) and tert-butyl 4-(aminomethyl)-4-hydroxypiperidine-1-carboxylate (step 2 of Example 22).

MS (ESI) m/z: 336 (M+H)+. –BOC

¹H-NMR (CDCl₃) δ: 8.91 (1H, t, J=6.1 Hz), 8.01 (1H, dd, J=10.2, 2.5 Hz), 7.16 (1H, dd, J=8.4, 5.6 Hz), 6.90 (1H, dt, J=8.4, 2.5 Hz), 3.95-3.74 (2H, m), 3.44 (2H, d, J=6.1 Hz), 3.28-3.12 (2H, m), 1.71-1.45 (4H, m), 1.46 (9H, s), 1.43 (6H, s). A signal due to OH was not observed.

Step 4. 6-Fluoro-N-[(4-hydroxypiperidin-4-yl)methyl]-3,3-dimethyl-2-oxoindoline-1-carboxamide The title compound was prepared according to the procedure described in step 2 of Example 2 from tert-butyl 4-({[(6-fluoro-3,3-dimethyl-2-oxo-2,3-dihydro-1H-indol-1-yl)carbonyl]amino}methyl)-4-hydroxypiperidine-1-carboxylate (step 3 of Example 22).

MS (ESI) m/z: 336 (M+H)+.

¹H-NMR (CDCl₃) δ: 8.88 (1H, t, J=5.8 Hz), 8.02 (1H, dd, J=10.5, 2.3 Hz), 7.15 (1H, dd, J=8.4, 5.6 Hz), 6.89 (1H, dt, J=8.4, 2.3 Hz), 3.45 (2H, d, J=5.8 Hz), 3.04-2.82 (4H, m), 1.69-1.57 (4H, m) 1.43 (6H, s). A signal due to OH was not observed.

Step 5. Methyl 1-{[4-({[(6-fluoro-3,3-dimethyl-2-oxo-2,3-dihydro-1H-indol-1-yl)carbonyl]amino}methyl)-4-hydroxypiperidin-1-yl]methyl}cyclobutanecarboxylate The title compound was prepared according to the procedure described in step 3 of Example 2 from 6-fluoro-N-[(4-hydroxypiperidin-4-yl)methyl]-3,3-dimethyl-2-oxoindoline-1-carboxamide and methyl 1-formylcyclobutanecarboxylate (step 4 of Example 22) and methyl 1-formylcyclobutanecarboxylate (Davis, Charles R. et al., *J. Org. Chem.*, 1993, 58, 6843).

MS (ESI) m/z: 462 (M+H)+.

¹H-NMR (CDCl₃) δ: 8.85 (1H, t, J=5.8 Hz), 8.02 (1H, dd, J=10.4, 2.6 Hz), 7.14 (1H, dd, J=8.6, 5.3 Hz), 6.88 (1H, dt, J=8.6, 2.6 Hz), 3.70 (3H, s), 3.40 (2H, d, J=5.8 Hz), 2.73 (2H, s), 2.61-2.30 (6H, m), 2.10-1.78 (6H, m), 1.65-1.56 (2H, m) 1.42 (6H, s). A signal due to OH was not observed.

Step 6. 1-{[4-({[(6-Fluoro-3,3-dimethyl-2-oxo-2,3-dihydro-1H-indol-1-yl)carbonyl]amino}methyl)-4-hydroxy piperidin-1-yl]methyl}cyclobutanecarboxylic Acid The title compound was prepared according to the procedure described in step 4 of Example 2 from methyl 1-{[4-({[(6-fluoro-3,3-dimethyl-2-oxo-2,3-dihydro-1H-indol-1-yl)carbonyl]amino}methyl)-4-hydroxypiperidin-1-yl]methyl}cyclobutanecarboxylate (step 5 of Example 22).

m.p.: 159° C.

IR (KBr) v: 3300, 2939, 1738, 1535, 1495, 1481, 1350, 1302, 1231, 1155 cm⁻¹.

MS (ESI) m/z: 448 (M+H)+.

¹H-NMR (CDCl₃) δ: 8.94 (1H, t, J=5.9 Hz), 7.99 (1H, dd, J=10.2, 2.3 Hz), 7.16 (1H, dd, J=8.5, 5.6 Hz), 6.90 (1H, dt, J=8.5, 2.3 Hz), 3.46 (2H, d, J=5.9 Hz), 2.95-2.74 (4H, br), 2.84 (2H, s), 2.61-2.48 (2H, m), 2.41-2.24 (1H, m), 2.04-1.86 (3H, m), 1.83-1.66 (4H, m), 1.43 (6H, s). Signals due to OH and CO₂H were not observed.

Anal. Calcd. for C₂₃H₃₀FN₃O₅ 1H₂O: C, 59.34; H, 6.93; N, 9.03. Found: C, 59.02; H, 6.57; N, 8.95.

Example 23

1-{[4-({[(3,3-DIMETHYL-2-OXO-2,3-DIHYDRO-1H-INDOL-1-YL)CARBONYL]AMINO}METHYL)PIPERIDIN-1-YL]METHYL}CYCLOBUTANECARBOXYLIC ACID HYDROGEN CHLORIDE SALT

1-{[4-({[(3,3-Dimethyl-2-oxo-2,3-dihydro-1h-indol-1-yl)carbonyl]amino}methyl)piperidin-1-yl]methyl}cyclobutanecarboxylic acid (41.0 g, 99.2 mmol, Example 9) was dissolved with tetrahydrofuran (820 mL). The mixture was filtered and washed with tetrahydrofuran (410 mL) and the resulting solution was heated to 45° C. Aqueous concentrated hydrogen chloride (12N, 8.27 mL, 99.2 mmol) was added to the solution at 45° C. for 20 min and stirred at this temperature for 1 h. The suspension was cooled to 20° C. for 1 min stirred at 2 h. After filtration, the resulting solid was washed with tetrahydrofuran (205 mL), and dried in vacuo at 40° C. The titled compound was obtained as white solid (38.6 g, 86.6%)

PXRD (2θ(+/−0.1): 9.2, 11.0, 16.5, 22.0)

Example 24

1-{[4-({[(3,3-DIMETHYL-2-OXO-2,3-DIHYDRO-1H-INDOL-1-YL)CARBONYL]AMINO}METHYL)PIPERIDIN-1-YL]METHYL}CYCLOBUTANECARBOXYLIC ACID HEMIFUMARATE SALT

1-{[4-({[(3,3-Dimethyl-2-oxo-2,3-dihydro-1h-indol-1-yl)carbonyl]amino}methyl)piperidin-1-yl]methyl}cyclobutanecarboxylic acid (2.09 g, 5.04 mmol, Example 9) was dissolved with THF (25 mL) at 60° C. Fumaric acid (293 mg, 2.52 mmol) was added to the solution. The mixture was concentrated until 12.5 mL. It was cooled to room temperature, and stirred for 1 h. After filtration, the obtained solid was washed with THF (3 mL), and dried in vacuo. The desired compound was obtained as a white solid (2.02 g, 85%).

¹H NMR (DMSO, 6) 8.59 (t, 1H, J=5.9 Hz), 8.04 (d, 1H, J=8.1 Hz), 7.44 (dd, 1H, J=1.5, 7.3 Hz), 7.30 (ddd, 1H, J=1.5, 8.1, 8.1 Hz), 7.19 (dd, 1H=8.1, 7.3 Hz), 6.62 (s, 1H), 3.19 (t, 2H, J=5.9 Hz), 2.89 (br-d, 2H, J=11.8 Hz), 2.75 (s, 2H), 2.35-2.20 (m, 2H), 2.20 (br-t, 2H, J=11.8 Hz), 2.00-1.75 (m, 4H), 1.75-1.50 (m, 3H), 1.37 (s, 6H), 1.30-1.10 (m, 2H).

mp 181° C.

PXRD (2θ(+/−0.1): 5.7, 10.8, 11.4, 12.4, 16.6)

Preparation:

3,3-DIMETHYL-1,3-DIHYDRO-2H-INDOL-2-ONE

Step 1.1-bromo-1-methyl-propananilide

Under nitrogen atmosphere, a solution of 2-bromoisobutyryl bromide (150 g, 652 mmol) in ethyl acetate (200 mL) was added to a well-stirring solution of aniline (66.8 g, 717 mmol) and Et₃N (72.6 g, 717 mmol) in ethyl acetate (400 mL) on ice bath, maintaining reaction temperature under 30° C. The mixture was stirred at room temperature for 2 h. The cold water (600 mL) was added and stirred at room temperature for 20 min. The mixture was separated and the aqueous layer was extracted with ethyl acetate (600 mL). The combined organic layer was washed with 2N HCl (180 mL), water (180 mL) and dried over sodium sulfate. After filtration, the filtrate was concentrated. The desired compound was obtained as a pale yellow solid (153 g, 97%).

Rf 0.77 (heptane/ethyl acetate=60/40)

$^1$H NMR (CDCl3, δ) 8.46 (br-s, 1H), 7.55 (d, 2H, J=8.1 Hz), 7.36 (dd, 2H, J=7.3, 8.1 Hz), 7.16 (t, 1H, J=7.3 Hz), 2.06 (s, 6H)

Step 2. 3,3-Dimethyl-1,3-dihydro-2h-indol-2-one

A mixture of AlCl$_3$ (16.5 g, 75.0 mmol) and 1-bromo-1-methyl-propananilide (10.0 g, 41.3 mmol, Step 1) was heated slowly to about 90° C. The mixture was maintained at 90-120° C. for 30 min. The mixture was cooled at 30-40° C. then toluene (100 mL) was added to the well-stirring mixture. The resulting slurry was added to well-stirring ice water (100 g). The mixture was separated and the aqueous layer was extracted with ethyl acetate (50 mL). The combined organic layer was washed with 1N HCl (30 mL), 10 wt % aqueous sodium carbonate (30 mL), dried over sodium sulfate, and filtered. The filtrate was evaporated affording a yellow solid. (6.94 g). The obtained solid was dissolved with ethyl acetate (14 mL) under reflux. The solution was cooled slowly to room temperature and it was stirred at room temperature for 1 h. Heptane (56 mL) was added slowly to the resulting slurry. The slurry was stirred at 20-30° C. for 1 h and cooled to 0-5° C. After stirring for 1 h, it was filtered off and the obtained solid was washed with a small amount of ethyl acetate/heptane (1/4). The desired compound was obtained as a white solid (5.4 g, 81%).

Product: Rf 0.37 (heptane/ethyl acetate=60/40)

$^1$H NMR (CDCl3, δ) 7.60 (br-s, 1H), 7.23-7.18 (m, 2H), 7.05 (t, 1H, J=7.3 Hz), 6.90 (dd, 1H, J=1.5, 7.3 Hz), 1.40 (s, 6H)

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:

1. The compound having the structure:

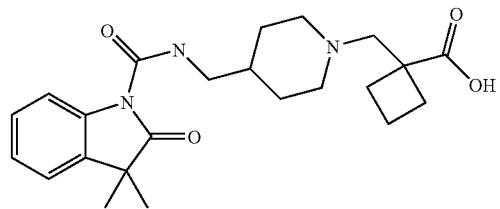

or a pharmaceutically acceptable salt thereof.

2. A method of treating gastroesophageal reflux disease (GERD) comprising administering to a mammal having GERD, including a human, an effective amount of the compound of claim 1 or a pharmaceutically acceptable salt thereof.

3. The method of claim 2, wherein the mammal is a human.

4. A pharmaceutical composition comprising the compound of claim 1 or a pharmaceutically acceptable salt thereof together with at least one pharmaceutically acceptable excipient.

5. A method of treating gastroesophageal reflux disease (GERD) comprising administering to a mammal having GERD, including a human, an effective amount of the composition of claim 4.

* * * * *